US008945063B2

(12) United States Patent
Wotton et al.

(10) Patent No.: US 8,945,063 B2
(45) Date of Patent: Feb. 3, 2015

(54) HAZARDOUS AGENT INJECTION SYSTEM

(71) Applicant: Antares Pharma, Inc., Ewing, NJ (US)

(72) Inventors: Paul K. Wotton, Newton, PA (US); Peter L. Sadowski, Woodbury, MN (US); John William Hayes, Chaska, MN (US)

(73) Assignee: Antares Pharma, Inc., Ewing, NJ (US)

( * ) Notice: Subject to any disclaimer, the term of this patent is extended or adjusted under 35 U.S.C. 154(b) by 0 days.

(21) Appl. No.: 14/158,289

(22) Filed: Jan. 17, 2014

(65) Prior Publication Data

US 2014/0135303 A1    May 15, 2014

Related U.S. Application Data

(63) Continuation of application No. 13/758,913, filed on Feb. 4, 2013, now abandoned, which is a continuation of application No. 13/607,659, filed on Sep. 7, 2012, now Pat. No. 8,480,631, which is a continuation of application No. 13/257,555, filed as application No. PCT/US2010/028011 on Mar. 19, 2010, now Pat. No. 8,579,865.

(60) Provisional application No. 61/162,114, filed on Mar. 20, 2009.

(51) Int. Cl.

| | |
|---|---|
| *A61M 5/00* | (2006.01) |
| *A61M 5/315* | (2006.01) |
| *A61K 9/00* | (2006.01) |
| *A61K 31/519* | (2006.01) |
| *A61M 5/20* | (2006.01) |
| *A61M 5/30* | (2006.01) |
| *A61M 5/178* | (2006.01) |

(Continued)

(52) U.S. Cl.
CPC ............ *A61K 9/0087* (2013.01); *A61K 9/0019* (2013.01); *A61K 31/519* (2013.01); *A61M 5/2033* (2013.01); *A61M 5/30* (2013.01); *A61M 5/3202* (2013.01); *A61M 5/326* (2013.01); *A61M 2005/2013* (2013.01); *A61M 2005/2073* (2013.01); *A61M 2005/3247* (2013.01); *A61M 5/178* (2013.01); *A61K 31/568* (2013.01)
USPC ........... 604/181; 604/187; 604/218; 604/228; 604/232

(58) Field of Classification Search
USPC .......... 604/134–136, 181, 187, 232, 218, 228
See application file for complete search history.

(56) References Cited

U.S. PATENT DOCUMENTS

| | | |
|---|---|---|
| 547,370 A | 10/1895 | Chalefou |
| 1,465,793 A | 8/1923 | Schilling |

(Continued)

FOREIGN PATENT DOCUMENTS

| | | |
|---|---|---|
| AR | 00081651 | 10/2012 |
| AU | 2008309660 | 4/2009 |

(Continued)

OTHER PUBLICATIONS

"Skin", American Medical Association (AMA) Current Procedural Terminology , 1998, http://www.ama-assn.org/ama/pub/category/print/7176.html, 1 page.

(Continued)

*Primary Examiner* — Emily Schmidt
*Assistant Examiner* — Lauren M Peng
(74) *Attorney, Agent, or Firm* — Morgan, Lewis & Bockius LLP

(57) ABSTRACT

Injection systems comprising a powered injector and one or more hazardous agents are disclosed.

20 Claims, 12 Drawing Sheets

(51) Int. Cl.
*A61K 31/568* (2006.01)
*A61M 5/32* (2006.01)

(56) References Cited

U.S. PATENT DOCUMENTS

| | | |
|---|---|---|
| 1,512,294 A | 10/1924 | Marcy |
| 1,687,323 A | 10/1928 | Cook |
| 2,354,649 A | 8/1944 | Bruckner |
| 2,607,344 A | 8/1952 | Brown |
| 2,645,223 A | 7/1953 | Lawshe |
| 2,648,334 A | 8/1953 | Brown |
| 2,687,730 A | 8/1954 | Hein |
| 2,688,967 A | 9/1954 | Huber |
| 2,699,166 A | 1/1955 | Bickinson |
| 2,717,601 A | 9/1955 | Brown |
| 2,728,341 A | 12/1955 | Roehr |
| 2,737,946 A | 3/1956 | Hein, Jr. |
| 2,813,528 A | 11/1957 | Blackman |
| 2,866,458 A | 12/1958 | Mesa et al. |
| 2,888,924 A | 6/1959 | Dunmire |
| 2,893,390 A | 7/1959 | Lockhart |
| 3,130,724 A | 4/1964 | Higgins |
| 3,166,069 A | 1/1965 | Enstrom |
| 3,375,825 A | 4/1968 | Keller |
| 3,382,865 A | 5/1968 | Worrall |
| 3,526,225 A | 9/1970 | Hayamamachi |
| 3,563,098 A | 2/1971 | Gley |
| 3,605,744 A | 9/1971 | Dwyer |
| 3,688,765 A | 9/1972 | Gasaway |
| 3,702,609 A | 11/1972 | Steiner |
| 3,712,301 A | 1/1973 | Sarnoff |
| 3,557,784 A | 7/1973 | Post et al. |
| 3,742,948 A | 7/1973 | Post et al. |
| 3,770,026 A | 11/1973 | Isenberg |
| 3,790,048 A | 2/1974 | Luciano et al. |
| 3,797,489 A | 3/1974 | Sarnoff |
| 3,797,491 A | 3/1974 | Hurschman |
| 3,811,441 A | 5/1974 | Sarnoff |
| 3,831,814 A | 8/1974 | Butler |
| 3,848,593 A | 11/1974 | Baldwin |
| 3,882,863 A | 5/1975 | Sarnoff et al. |
| 3,892,237 A | 7/1975 | Steiner |
| 3,895,633 A | 7/1975 | Bartner et al. |
| 3,946,732 A | 3/1976 | Hurscham |
| 4,031,893 A | 6/1977 | Kaplan et al. |
| 4,067,333 A | 1/1978 | Reinhardt et al. |
| 4,127,118 A | 11/1978 | Latorre |
| 4,171,698 A | 10/1979 | Genese |
| 4,222,392 A | 9/1980 | Brennan |
| 4,227,528 A | 10/1980 | Wardlaw |
| 4,258,713 A | 3/1981 | Wardlaw |
| 4,282,986 A | 8/1981 | Ekenstam et al. |
| 4,316,463 A | 2/1982 | Schmitz et al. |
| 4,316,643 A | 2/1982 | Burk et al. |
| 4,328,802 A | 5/1982 | Curley et al. |
| 4,333,456 A | 6/1982 | Webb |
| 4,333,458 A | 6/1982 | Margulies et al. |
| 4,338,980 A | 7/1982 | Schwebel et al. |
| 4,373,526 A | 2/1983 | Kling |
| 4,378,015 A | 3/1983 | Wardlaw |
| 4,411,661 A | 10/1983 | Kersten |
| 4,484,910 A | 11/1984 | Sarnoff et al. |
| 4,529,403 A | 7/1985 | Kamstra |
| 4,553,962 A | 11/1985 | Brunet |
| 4,558,690 A | 12/1985 | Joyce |
| 4,573,971 A | 3/1986 | Kamstra |
| 4,592,745 A | 6/1986 | Rex et al. |
| 4,624,660 A | 11/1986 | Mijers et al. |
| 4,634,027 A | 1/1987 | Kanarvogel |
| 4,661,098 A | 4/1987 | Bekkering et al. |
| 4,662,878 A | 5/1987 | Lindmayer |
| 4,664,653 A | 5/1987 | Sagstetter et al. |
| 4,664,655 A | 5/1987 | Orentreich et al. |
| 4,678,461 A | 7/1987 | Mesa |
| 4,719,825 A | 1/1988 | LaHaye et al. |
| 4,722,728 A | 2/1988 | Dixon |
| 4,774,772 A | 10/1988 | Vetter et al. |
| 4,790,824 A | 12/1988 | Morrow et al. |
| 4,818,517 A | 4/1989 | Kwee et al. |
| 4,820,286 A | 4/1989 | van der Wal |
| 4,822,340 A | 4/1989 | Kamstra |
| 4,830,217 A | 5/1989 | Dufresne et al. |
| 4,874,381 A | 10/1989 | Vetter |
| 4,883,472 A | 11/1989 | Michel |
| 4,913,699 A | 4/1990 | Parsons |
| 4,915,701 A | 4/1990 | Halkyard |
| 4,929,238 A | 5/1990 | Baum |
| 4,936,833 A | 6/1990 | Sams |
| 4,940,460 A | 7/1990 | Casey et al. |
| 4,966,581 A | 10/1990 | Landau |
| 4,968,302 A | 11/1990 | Schluter et al. |
| 4,973,318 A | 11/1990 | Holm et al. |
| 4,976,701 A | 12/1990 | Ejlersen et al. |
| 4,982,769 A | 1/1991 | Fournier et al. |
| 4,986,816 A | 1/1991 | Steiner et al. |
| 5,042,977 A | 8/1991 | Bechtold et al. |
| 5,062,830 A | 11/1991 | Dunlap |
| 5,064,413 A | 11/1991 | McKinnon et al. |
| 5,069,670 A | 12/1991 | Vetter et al. |
| 5,078,680 A | 1/1992 | Sarnoff |
| 5,080,648 A | 1/1992 | D'Antonio |
| 5,080,649 A | 1/1992 | Vetter |
| 5,085,641 A | 2/1992 | Sarnoff et al. |
| 5,085,642 A | 2/1992 | Sarnoff et al. |
| 5,092,842 A | 3/1992 | Bechtold et al. |
| 5,102,388 A | 4/1992 | Richmond |
| 5,102,393 A | 4/1992 | Sarnoff et al. |
| 5,104,380 A | 4/1992 | Holman et al. |
| 5,114,406 A | 5/1992 | Gabriel et al. |
| 5,137,516 A | 8/1992 | Rand et al. |
| 5,137,528 A | 8/1992 | Crose |
| 5,139,490 A | 8/1992 | Vetter et al. |
| 5,163,907 A | 11/1992 | Szuszkiewicz |
| 5,176,643 A | 1/1993 | Kramer et al. |
| 5,180,370 A | 1/1993 | Gillespie |
| 5,185,985 A | 2/1993 | Vetter et al. |
| 5,195,983 A | 3/1993 | Boese |
| 5,221,348 A | 6/1993 | Masano |
| 5,226,895 A | 7/1993 | Harris |
| 5,232,459 A | 8/1993 | Hjertman |
| 5,256,142 A | 10/1993 | Colavecchio |
| 5,263,934 A | 11/1993 | Haak |
| 5,271,744 A | 12/1993 | Kramer et al. |
| 5,279,543 A | 1/1994 | Glikfeld et al. |
| 5,279,576 A | 1/1994 | Loo et al. |
| 5,279,585 A | 1/1994 | Balkwill |
| 5,279,586 A | 1/1994 | Balkwill |
| 5,281,198 A | 1/1994 | Haber et al. |
| 5,290,228 A | 3/1994 | Uemura et al. |
| 5,295,965 A | 3/1994 | Wilmot |
| 5,300,030 A | 4/1994 | Crossman et al. |
| 5,304,128 A | 4/1994 | Haber et al. |
| 5,304,152 A | 4/1994 | Sams |
| 5,308,341 A | 5/1994 | Chanoch |
| 5,318,522 A | 6/1994 | D'Antonio |
| 5,320,603 A | 6/1994 | Vetter et al. |
| 5,330,431 A | 7/1994 | Herskowitz |
| 5,332,399 A | 7/1994 | Grabenkort et al. |
| 5,334,144 A | 8/1994 | Alchas et al. |
| 5,342,308 A | 8/1994 | Boschetti |
| 5,350,367 A | 9/1994 | Stiehl et al. |
| 5,354,286 A | 10/1994 | Mesa et al. |
| 5,358,489 A | 10/1994 | Wyrick |
| RE34,845 E | 1/1995 | Vetter et al. |
| 5,391,151 A | 2/1995 | Wilmot |
| 5,405,362 A | 4/1995 | Kramer et al. |
| 5,415,648 A | 5/1995 | Malay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,505,694 A | 4/1996 | Hubbard et al. |
| 5,514,097 A | 5/1996 | Knauer |
| 5,514,107 A | 5/1996 | Haber et al. |
| 5,540,664 A | 7/1996 | Wyrick |

(56) References Cited

U.S. PATENT DOCUMENTS

| | | |
|---|---|---|
| 5,542,760 A | 8/1996 | Chanoch et al. |
| 5,544,234 A | 8/1996 | Terajima et al. |
| 5,549,561 A | 8/1996 | Hjertman |
| 5,554,134 A | 9/1996 | Bonnichsen |
| 5,562,625 A | 10/1996 | Stefancin, Jr. |
| 5,567,160 A | 10/1996 | Massino |
| 5,569,190 A | 10/1996 | D'Antonio |
| 5,569,192 A | 10/1996 | van der Wal |
| 5,569,236 A | 10/1996 | Kriesel |
| 5,573,042 A | 11/1996 | De Haen |
| 5,593,388 A | 1/1997 | Phillips |
| 5,599,302 A | 2/1997 | Lilley et al. |
| 5,599,309 A | 2/1997 | Marshall et al. |
| 5,605,542 A | 2/1997 | Tanaka et al. |
| 5,637,094 A | 6/1997 | Stewart, Jr. et al. |
| 5,637,100 A | 6/1997 | Sudo |
| 5,649,912 A | 7/1997 | Peterson |
| 5,658,259 A | 8/1997 | Pearson et al. |
| 5,665,071 A | 9/1997 | Wyrick |
| 5,688,251 A | 11/1997 | Chanoch |
| 5,695,472 A | 12/1997 | Wyrick |
| 5,704,911 A | 1/1998 | Parsons |
| 5,725,508 A | 3/1998 | Chanoch et al. |
| 5,730,723 A | 3/1998 | Castellano et al. |
| 5,743,889 A | 4/1998 | Sams |
| 5,769,138 A | 6/1998 | Sadowski et al. |
| 5,785,691 A | 7/1998 | Vetter et al. |
| 5,788,670 A | 8/1998 | Reinhard et al. |
| 5,801,057 A | 9/1998 | Smart et al. |
| 5,807,309 A | 9/1998 | Lundquist et al. |
| 5,820,602 A | 10/1998 | Kovelman et al. |
| 5,820,622 A | 10/1998 | Gross et al. |
| 5,827,232 A | 10/1998 | Chanoch et al. |
| 5,836,911 A | 11/1998 | Marzynski et al. |
| 5,843,036 A | 12/1998 | Olive et al. |
| 5,846,233 A | 12/1998 | Lilley et al. |
| 5,851,197 A | 12/1998 | Marano et al. |
| 5,851,198 A | 12/1998 | Castellano et al. |
| 5,860,456 A | 1/1999 | Bydlon et al. |
| 5,865,795 A | 2/1999 | Schiff et al. |
| 5,865,799 A | 2/1999 | Tanaka et al. |
| 5,868,711 A | 2/1999 | Kramer et al. |
| 5,873,857 A | 2/1999 | Kriesel |
| 5,875,976 A | 3/1999 | Nelson et al. |
| 5,879,327 A | 3/1999 | DeFarges et al. |
| 5,891,085 A | 4/1999 | Lilley et al. |
| 5,891,086 A | 4/1999 | Weston |
| 5,893,842 A | 4/1999 | Imbert |
| 5,919,159 A | 7/1999 | Lilley et al. |
| 5,921,966 A | 7/1999 | Bendek et al. |
| 5,925,017 A | 7/1999 | Kriesel et al. |
| 5,928,205 A | 7/1999 | Marshall |
| 5,935,949 A | 8/1999 | White |
| 5,951,528 A | 9/1999 | Parkin |
| 5,957,897 A | 9/1999 | Jeffrey |
| 5,960,797 A | 10/1999 | Kramer et al. |
| 5,989,227 A | 11/1999 | Vetter et al. |
| 6,004,297 A | 12/1999 | Steenfeldt-Jensen et al. |
| 6,045,534 A | 4/2000 | Jacobsen et al. |
| 6,056,716 A | 5/2000 | D'Antonio et al. |
| 6,077,247 A | 6/2000 | Marshall et al. |
| 6,083,201 A | 7/2000 | Skinkle |
| 6,090,070 A | 7/2000 | Hager et al. |
| 6,099,504 A | 8/2000 | Gross et al. |
| 6,123,684 A | 9/2000 | Deboer et al. |
| 6,132,395 A | 10/2000 | Landau et al. |
| 6,159,181 A | 12/2000 | Crossman et al. |
| 6,171,276 B1 | 1/2001 | Lippe et al. |
| 6,203,529 B1 | 3/2001 | Gabriel et al. |
| 6,210,369 B1 | 4/2001 | Wilmot et al. |
| 6,221,046 B1 | 4/2001 | Burroughs et al. |
| 6,221,053 B1 | 4/2001 | Walters et al. |
| 6,223,408 B1 | 5/2001 | Vetter et al. |
| 6,231,540 B1 | 5/2001 | Smedegaard |
| 6,241,709 B1 | 6/2001 | Bechtold et al. |
| 6,258,078 B1 | 7/2001 | Thilly |
| 6,264,629 B1 | 7/2001 | Landau |
| 6,270,479 B1 | 8/2001 | Bergens et al. |
| 6,309,371 B1 | 10/2001 | Deboer et al. |
| 6,319,224 B1 | 11/2001 | Stout et al. |
| 6,371,939 B2 | 4/2002 | Bergens et al. |
| 6,383,168 B1 | 5/2002 | Landau et al. |
| 6,391,003 B1 | 5/2002 | Lesch, Jr. |
| 6,406,456 B1 | 6/2002 | Slate et al. |
| 6,428,528 B2 | 8/2002 | Sadowski et al. |
| 6,471,669 B2 | 10/2002 | Landau |
| 6,494,865 B1 | 12/2002 | Alchas |
| 6,517,517 B1 | 2/2003 | Farrugia et al. |
| 6,530,904 B1 | 3/2003 | Edwards et al. |
| 6,544,234 B1 | 4/2003 | Gabriel |
| 6,562,006 B1 | 5/2003 | Hjertman et al. |
| 6,565,553 B2 | 5/2003 | Sadowski et al. |
| 6,568,259 B2 | 5/2003 | Saheki et al. |
| 6,569,123 B2 | 5/2003 | Alchas et al. |
| 6,569,143 B2 | 5/2003 | Alchas et al. |
| 6,584,910 B1 | 7/2003 | Plass |
| 6,589,210 B1 | 7/2003 | Rolfe |
| 6,607,508 B2 | 8/2003 | Knauer |
| 6,620,137 B2 | 9/2003 | Kirchhofer et al. |
| 6,641,561 B1 | 11/2003 | Hill et al. |
| 6,645,170 B2 | 11/2003 | Landau |
| 6,656,150 B2 | 12/2003 | Hill et al. |
| 6,673,035 B1 | 1/2004 | Rice et al. |
| 6,682,504 B2 | 1/2004 | Nelson et al. |
| 6,689,092 B2 | 2/2004 | Zierenberg et al. |
| 6,706,000 B2 | 3/2004 | Perez et al. |
| 6,746,429 B2 | 6/2004 | Sadowski et al. |
| 6,767,336 B1 | 7/2004 | Kaplan |
| 6,805,686 B1 | 10/2004 | Fathallah et al. |
| 6,830,560 B1 | 12/2004 | Gross et al. |
| 6,899,698 B2 | 5/2005 | Sams |
| 6,932,793 B1 | 8/2005 | Marshall et al. |
| 6,932,794 B2 | 8/2005 | Giambattista et al. |
| 6,936,032 B1 | 8/2005 | Bush, Jr. et al. |
| 6,969,370 B2 | 11/2005 | Langley et al. |
| 6,969,372 B1 | 11/2005 | Halseth |
| 6,979,316 B1 | 12/2005 | Rubin et al. |
| 6,986,758 B2 | 1/2006 | Schiffmann |
| 6,997,901 B2 | 2/2006 | Popovsky |
| 7,018,364 B2 | 3/2006 | Giambattista et al. |
| 7,066,907 B2 | 6/2006 | Crossman et al. |
| 7,112,187 B2 | 9/2006 | Karlsson |
| 7,118,552 B2 | 10/2006 | Shaw et al. |
| 7,118,553 B2 | 10/2006 | Scherer |
| 7,169,132 B2 | 1/2007 | Bendek et al. |
| 7,195,616 B2 | 3/2007 | Diller et al. |
| 7,218,962 B2 | 5/2007 | Freyman |
| 7,220,247 B2 | 5/2007 | Shaw et al. |
| 7,247,149 B2 | 7/2007 | Beyerlein |
| 7,291,132 B2 | 11/2007 | DeRuntz et al. |
| 7,292,885 B2 | 11/2007 | Scott et al. |
| 7,297,136 B2 | 11/2007 | Wyrick |
| 7,341,575 B2 | 3/2008 | Rice et al. |
| 7,361,160 B2 | 4/2008 | Hommann et al. |
| 7,390,314 B2 | 6/2008 | Stutz, Jr. et al. |
| 7,390,319 B2 | 6/2008 | Friedman |
| 7,407,492 B2 | 8/2008 | Gurtner |
| 7,416,540 B2 | 8/2008 | Edwards et al. |
| 7,442,185 B2 | 10/2008 | Amark et al. |
| 7,449,012 B2 | 11/2008 | Young et al. |
| 7,488,308 B2 | 2/2009 | Lesch, Jr. |
| 7,488,313 B2 | 2/2009 | Segal et al. |
| 7,488,314 B2 | 2/2009 | Segal et al. |
| 7,500,964 B2 | 3/2009 | Shaw et al. |
| 7,517,342 B2 | 4/2009 | Scott et al. |
| 7,519,418 B2 | 4/2009 | Scott et al. |
| 7,544,188 B2 | 6/2009 | Edwards et al. |
| 7,547,293 B2 | 6/2009 | Williamson et al. |
| 7,569,035 B1 | 8/2009 | Wilmot et al. |
| 7,611,491 B2 | 11/2009 | Pickhard |
| 7,621,887 B2 | 11/2009 | Griffiths et al. |
| 7,621,891 B2 | 11/2009 | Wyrick |
| 7,635,348 B2 | 12/2009 | Raven et al. |
| 7,635,350 B2 | 12/2009 | Scherer |

(56) References Cited

U.S. PATENT DOCUMENTS

| | | |
|---|---|---|
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Serna et al. |
| 7,658,724 B2 | 2/2010 | Rubin et al. |
| 7,670,314 B2 | 3/2010 | Wall et al. |
| 7,704,237 B2 | 4/2010 | Fisher et al. |
| 7,717,877 B2 | 5/2010 | Lavi et al. |
| 7,722,595 B2 | 5/2010 | Pettis et al. |
| 7,731,686 B2 | 6/2010 | Edwards et al. |
| 7,731,690 B2 | 6/2010 | Edwards et al. |
| 7,736,333 B2 | 6/2010 | Gillespie, III |
| 7,744,582 B2 | 6/2010 | Sadowski et al. |
| 7,749,194 B2 | 7/2010 | Edwards et al. |
| 7,749,195 B2 | 7/2010 | Hommann |
| 7,762,996 B2 | 7/2010 | Palasis |
| 7,776,015 B2 | 8/2010 | Sadowski et al. |
| 7,794,432 B2 | 9/2010 | Young et al. |
| 7,811,254 B2 | 10/2010 | Wilmot et al. |
| 7,862,543 B2 | 1/2011 | Potter et al. |
| 7,896,841 B2 | 3/2011 | Wall et al. |
| 7,901,377 B1 | 3/2011 | Harrison et al. |
| 7,905,352 B2 | 3/2011 | Wyrick |
| 7,905,866 B2 | 3/2011 | Haider et al. |
| 7,918,823 B2 | 4/2011 | Edwards et al. |
| 7,927,303 B2 | 4/2011 | Wyrick |
| 7,931,618 B2 | 4/2011 | Wyrick |
| 7,947,017 B2 | 5/2011 | Edwards et al. |
| RE42,463 E | 6/2011 | Landau |
| 7,955,304 B2 | 6/2011 | Guillermo |
| 7,967,772 B2 | 6/2011 | McKenzie et al. |
| 7,988,675 B2 | 8/2011 | Gillespie, III et al. |
| 8,016,774 B2 | 9/2011 | Freeman et al. |
| 8,016,788 B2 | 9/2011 | Edwards et al. |
| 8,021,335 B2 | 9/2011 | Lesch, Jr. |
| 8,048,035 B2 | 11/2011 | Mesa et al. |
| 8,048,037 B2 | 11/2011 | Kohlbrenner et al. |
| 8,057,427 B2 | 11/2011 | Griffiths et al. |
| 8,066,659 B2 | 11/2011 | Joshi et al. |
| 8,083,711 B2 | 12/2011 | Enggaard |
| 8,100,865 B2 | 1/2012 | Spofforth |
| 8,105,272 B2 | 1/2012 | Williamson et al. |
| 8,105,281 B2 | 1/2012 | Edwards et al. |
| 8,110,209 B2 | 2/2012 | Prestrelski et al. |
| 8,123,719 B2 | 2/2012 | Edwards et al. |
| 8,123,724 B2 | 2/2012 | Gillespie, III |
| 8,162,873 B2 | 4/2012 | Muto et al. |
| 8,162,886 B2 | 4/2012 | Sadowski et al. |
| 8,167,840 B2 | 5/2012 | Matusch |
| 8,167,866 B2 | 5/2012 | Klein |
| 8,177,758 B2 | 5/2012 | Brooks, Jr. et al. |
| 8,187,224 B2 | 5/2012 | Wyrick |
| 8,216,180 B2 | 7/2012 | Tschirren et al. |
| 8,216,192 B2 | 7/2012 | Burroughs et al. |
| 8,226,618 B2 | 7/2012 | Geertsen |
| 8,226,631 B2 | 7/2012 | Boyd et al. |
| 8,233,135 B2 | 7/2012 | Jansen et al. |
| 8,235,952 B2 | 8/2012 | Wikner |
| 8,246,577 B2 | 8/2012 | Schrul et al. |
| 8,251,947 B2 | 8/2012 | Kramer et al. |
| 8,257,318 B2 | 9/2012 | Thogersen et al. |
| 8,257,319 B2 | 9/2012 | Plumptre |
| 8,267,899 B2 | 9/2012 | Moller |
| 8,267,900 B2 | 9/2012 | Harms et al. |
| 8,273,798 B2 | 9/2012 | Bausch et al. |
| 8,275,454 B2 | 9/2012 | Adachi et al. |
| 8,276,583 B2 | 10/2012 | Farieta et al. |
| 8,277,412 B2 | 10/2012 | Kronestedt |
| 8,277,413 B2 | 10/2012 | Kirchhofer |
| 8,298,175 B2 | 10/2012 | Hirschel et al. |
| 8,298,194 B2 | 10/2012 | Moller |
| 8,300,852 B2 | 10/2012 | Terada |
| RE43,834 E | 11/2012 | Steenfeldt-Jensen et al. |
| 8,308,232 B2 | 11/2012 | Zamperla et al. |
| 8,308,695 B2 | 11/2012 | Laiosa |
| 8,313,466 B2 | 11/2012 | Edwards et al. |
| 8,317,757 B2 | 11/2012 | Plumptre |
| 8,323,237 B2 | 12/2012 | Radmer et al. |
| 8,333,739 B2 | 12/2012 | Moller |
| 8,337,472 B2 | 12/2012 | Edginton et al. |
| 8,343,103 B2 | 1/2013 | Moser |
| 8,343,109 B2 | 1/2013 | Marshall et al. |
| 8,348,905 B2 | 1/2013 | Radmer et al. |
| 8,353,878 B2 | 1/2013 | Moller et al. |
| 8,357,120 B2 | 1/2013 | Moller et al. |
| 8,357,125 B2 | 1/2013 | Grunhut et al. |
| 8,361,036 B2 | 1/2013 | Moller et al. |
| 8,366,680 B2 | 2/2013 | Raab |
| 8,372,031 B2 | 2/2013 | Elmen et al. |
| 8,372,042 B2 | 2/2013 | Wieselblad |
| 8,376,993 B2 | 2/2013 | Cox et al. |
| 8,398,593 B2 | 3/2013 | Eich et al. |
| 8,409,149 B2 | 4/2013 | Hommann et al. |
| 8,435,215 B2 | 5/2013 | Arby et al. |
| 2001/0039394 A1 | 11/2001 | Weston |
| 2001/0049496 A1 | 12/2001 | Kirchhofer et al. |
| 2002/0007149 A1 | 1/2002 | Nelson et al. |
| 2002/0045866 A1 | 4/2002 | Sadowski et al. |
| 2002/0173752 A1 | 11/2002 | Polzin |
| 2002/0183690 A1 | 12/2002 | Arnisolle |
| 2002/0188251 A1 | 12/2002 | Staylor et al. |
| 2003/0040697 A1 | 2/2003 | Pass et al. |
| 2003/0083621 A1 | 5/2003 | Shaw et al. |
| 2003/0105430 A1 | 6/2003 | Lavi et al. |
| 2003/0130619 A1 | 7/2003 | Safabash et al. |
| 2003/0158523 A1 | 8/2003 | Hjertman et al. |
| 2003/0171717 A1 | 9/2003 | Farrugia et al. |
| 2003/0229330 A1 | 12/2003 | Hickle |
| 2003/0236502 A1 | 12/2003 | De La Serna et al. |
| 2004/0039336 A1 | 2/2004 | Amark et al. |
| 2004/0039337 A1 | 2/2004 | Letzing |
| 2004/0097783 A1 | 5/2004 | Peters et al. |
| 2004/0097883 A1 | 5/2004 | Roe |
| 2004/0143213 A1 | 7/2004 | Hunter et al. |
| 2004/0220524 A1 | 11/2004 | Sadowski et al. |
| 2004/0267207 A1 | 12/2004 | Veasey et al. |
| 2004/0267355 A1 | 12/2004 | Scott et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0080377 A1 | 4/2005 | Sadowski et al. |
| 2005/0101919 A1 | 5/2005 | Brunnberg |
| 2005/0165360 A1 | 7/2005 | Stamp |
| 2005/0165363 A1 | 7/2005 | Judson et al. |
| 2005/0209569 A1 | 9/2005 | Ishikawa et al. |
| 2005/0215955 A1 | 9/2005 | Slawson |
| 2005/0240145 A1 | 10/2005 | Scott et al. |
| 2005/0256499 A1 | 11/2005 | Pettis et al. |
| 2005/0261634 A1 | 11/2005 | Karlsson |
| 2005/0273054 A1 | 12/2005 | Asch |
| 2006/0025747 A1 | 2/2006 | Sullivan et al. |
| 2006/0106362 A1 | 5/2006 | Pass et al. |
| 2006/0129122 A1 | 6/2006 | Wyrick |
| 2006/0224124 A1 | 10/2006 | Scherer |
| 2006/0258988 A1 | 11/2006 | Keitel et al. |
| 2006/0258990 A1 | 11/2006 | Weber |
| 2007/0017533 A1 | 1/2007 | Wyrick |
| 2007/0025890 A1 | 2/2007 | Joshi et al. |
| 2007/0027430 A1 | 2/2007 | Hommann |
| 2007/0088288 A1 | 4/2007 | Barron et al. |
| 2007/0093775 A1 | 4/2007 | Daly |
| 2007/0100288 A1 | 5/2007 | Bozeman et al. |
| 2007/0123818 A1 | 5/2007 | Griffiths et al. |
| 2007/0123829 A1 | 5/2007 | Atterbury et al. |
| 2007/0129686 A1 | 6/2007 | Daily et al. |
| 2007/0129687 A1 | 6/2007 | Marshall et al. |
| 2007/0179145 A1* | 8/2007 | Karmali .............. 514/251 |
| 2007/0185432 A1 | 8/2007 | Etheredge et al. |
| 2007/0191784 A1 | 8/2007 | Jacobs et al. |
| 2007/0219498 A1 | 9/2007 | Malone et al. |
| 2008/0059133 A1 | 3/2008 | Edwards et al. |
| 2008/0154199 A1 | 6/2008 | Wyrick |
| 2008/0154200 A1 | 6/2008 | Lesch |
| 2008/0185069 A1 | 8/2008 | Clark |

(56) References Cited

U.S. PATENT DOCUMENTS

| | | |
|---|---|---|
| 2008/0262427 A1 | 10/2008 | Hommann |
| 2008/0262436 A1 | 10/2008 | Olson |
| 2008/0262445 A1 | 10/2008 | Hsu et al. |
| 2009/0124981 A1 | 5/2009 | Evans |
| 2009/0124997 A1 | 5/2009 | Pettis et al. |
| 2009/0204062 A1 | 8/2009 | Muto et al. |
| 2009/0254027 A1 | 10/2009 | Moller |
| 2009/0254035 A1 | 10/2009 | Kohlbrenner et al. |
| 2009/0292240 A1 | 11/2009 | Kramer et al. |
| 2009/0299278 A1 | 12/2009 | Lesch, Jr. et al. |
| 2009/0304812 A1 | 12/2009 | Staniforth et al. |
| 2009/0312705 A1 | 12/2009 | Grunhut |
| 2009/0318361 A1 | 12/2009 | Noera et al. |
| 2010/0016326 A1 | 1/2010 | Will |
| 2010/0036318 A1 | 2/2010 | Raday et al. |
| 2010/0049125 A1 | 2/2010 | James et al. |
| 2010/0069845 A1 | 3/2010 | Marshall et al. |
| 2010/0076378 A1 | 3/2010 | Runfola |
| 2010/0076400 A1 | 3/2010 | Wall |
| 2010/0087847 A1 | 4/2010 | Hong |
| 2010/0094214 A1 | 4/2010 | Abry et al. |
| 2010/0094324 A1 | 4/2010 | Huang et al. |
| 2010/0100039 A1 | 4/2010 | Wyrick |
| 2010/0114058 A1 | 5/2010 | Weitzel et al. |
| 2010/0121272 A1 | 5/2010 | Marshall et al. |
| 2010/0137798 A1 | 6/2010 | Streit et al. |
| 2010/0152699 A1 | 6/2010 | Ferrari et al. |
| 2010/0152702 A1 | 6/2010 | Vigil et al. |
| 2010/0160894 A1 | 6/2010 | Julian et al. |
| 2010/0168677 A1 | 7/2010 | Gabriel et al. |
| 2010/0174268 A1 | 7/2010 | Wilmot et al. |
| 2010/0191217 A1 | 7/2010 | Hommann et al. |
| 2010/0204678 A1 | 8/2010 | Imran |
| 2010/0217105 A1 | 8/2010 | Yodfat et al. |
| 2010/0228193 A1 | 9/2010 | Wyrick |
| 2010/0249746 A1 | 9/2010 | Klein |
| 2010/0256570 A1 | 10/2010 | Maritan |
| 2010/0262082 A1 | 10/2010 | Brooks et al. |
| 2010/0262083 A1 | 10/2010 | Grunhut et al. |
| 2010/0268170 A1 | 10/2010 | Carrel et al. |
| 2010/0274198 A1 | 10/2010 | Bechtold |
| 2010/0274273 A1 | 10/2010 | Schraga et al. |
| 2010/0288593 A1 | 11/2010 | Chiesa et al. |
| 2010/0292643 A1 | 11/2010 | Wilmot et al. |
| 2010/0292653 A1 | 11/2010 | Maritan |
| 2010/0298780 A1 | 11/2010 | Laiosa |
| 2010/0312196 A1 | 12/2010 | Hirschel et al. |
| 2010/0318035 A1 | 12/2010 | Edwards et al. |
| 2010/0318037 A1 | 12/2010 | Young et al. |
| 2010/0324480 A1 | 12/2010 | Chun |
| 2011/0021989 A1 | 1/2011 | Janek et al. |
| 2011/0034879 A1 | 2/2011 | Crow |
| 2011/0054414 A1 | 3/2011 | Shang et al. |
| 2011/0077599 A1 | 3/2011 | Wozencroft |
| 2011/0087192 A1 | 4/2011 | Uhland et al. |
| 2011/0098655 A1 | 4/2011 | Jennings et al. |
| 2011/0098656 A1 | 4/2011 | Burnell et al. |
| 2011/0125076 A1 | 5/2011 | Kraft et al. |
| 2011/0125100 A1 | 5/2011 | Schwirtz et al. |
| 2011/0137246 A1 | 6/2011 | Cali et al. |
| 2011/0137247 A1 | 6/2011 | Mesa et al. |
| 2011/0144594 A1 | 6/2011 | Sund et al. |
| 2011/0190725 A1 | 8/2011 | Pettis et al. |
| 2011/0196300 A1 | 8/2011 | Edwards et al. |
| 2011/0196311 A1 | 8/2011 | Bicknell et al. |
| 2011/0224620 A1 | 9/2011 | Johansen et al. |
| 2011/0238003 A1 | 9/2011 | Bruno-Raimondi et al. |
| 2011/0269750 A1 | 11/2011 | Kley et al. |
| 2011/0319864 A1 | 12/2011 | Beller et al. |
| 2012/0004608 A1 | 1/2012 | Lesch, Jr. |
| 2012/0016296 A1 | 1/2012 | Charles |
| 2012/0046609 A1 | 2/2012 | Mesa et al. |
| 2012/0053563 A1 | 3/2012 | Du |
| 2012/0059319 A1 | 3/2012 | Segal |
| 2012/0071829 A1 | 3/2012 | Edwards et al. |
| 2012/0095443 A1 | 4/2012 | Ferrari et al. |
| 2012/0101475 A1 | 4/2012 | Wilmot et al. |
| 2012/0116318 A1 | 5/2012 | Edwards et al. |
| 2012/0123350 A1 | 5/2012 | Giambattista et al. |
| 2012/0123385 A1 | 5/2012 | Edwards et al. |
| 2012/0130318 A1 | 5/2012 | Young |
| 2012/0130342 A1 | 5/2012 | Cleathero |
| 2012/0136303 A1 | 5/2012 | Cleathero |
| 2012/0136318 A1 | 5/2012 | Lanin et al. |
| 2012/0143144 A1 | 6/2012 | Young |
| 2012/0157931 A1 | 6/2012 | Nzike |
| 2012/0157965 A1 | 6/2012 | Wotton et al. |
| 2012/0172809 A1 | 7/2012 | Plumptre |
| 2012/0172811 A1 | 7/2012 | Enggaard et al. |
| 2012/0172812 A1 | 7/2012 | Plumptre et al. |
| 2012/0172813 A1 | 7/2012 | Plumptre et al. |
| 2012/0172814 A1 | 7/2012 | Plumptre et al. |
| 2012/0172815 A1 | 7/2012 | Holmqvist |
| 2012/0172816 A1 | 7/2012 | Boyd et al. |
| 2012/0172818 A1 | 7/2012 | Harms et al. |
| 2012/0172885 A1 | 7/2012 | Drapeau et al. |
| 2012/0179100 A1 | 7/2012 | Sadowski et al. |
| 2012/0179137 A1 | 7/2012 | Bartlett et al. |
| 2012/0184900 A1 | 7/2012 | Marshall et al. |
| 2012/0184917 A1 | 7/2012 | Bom et al. |
| 2012/0184918 A1 | 7/2012 | Bostrom |
| 2012/0186075 A1 | 7/2012 | Edginton |
| 2012/0191048 A1 | 7/2012 | Eaton |
| 2012/0191049 A1 | 7/2012 | Harms et al. |
| 2012/0197209 A1 | 8/2012 | Bicknell et al. |
| 2012/0197213 A1 | 8/2012 | Kohlbrenner et al. |
| 2012/0203184 A1 | 8/2012 | Selz et al. |
| 2012/0203185 A1 | 8/2012 | Kristensen et al. |
| 2012/0203186 A1 | 8/2012 | Vogt et al. |
| 2012/0209192 A1 | 8/2012 | Alexandersson |
| 2012/0209200 A1 | 8/2012 | Jones et al. |
| 2012/0209210 A1 | 8/2012 | Plumptre et al. |
| 2012/0209211 A1 | 8/2012 | Plumptre et al. |
| 2012/0209212 A1 | 8/2012 | Plumptre et al. |
| 2012/0215162 A1 | 8/2012 | Nielsen et al. |
| 2012/0215176 A1 | 8/2012 | Veasey et al. |
| 2012/0220929 A1 | 8/2012 | Nagel et al. |
| 2012/0220941 A1 | 8/2012 | Jones |
| 2012/0220953 A1 | 8/2012 | Holmqvist |
| 2012/0220954 A1 | 8/2012 | Cowe |
| 2012/0226226 A1 | 9/2012 | Edwards et al. |
| 2012/0230620 A1 | 9/2012 | Holdgate et al. |
| 2012/0232517 A1 | 9/2012 | Saiki |
| 2012/0245516 A1 | 9/2012 | Tschirren et al. |
| 2012/0245532 A1 | 9/2012 | Frantz et al. |
| 2012/0253274 A1 | 10/2012 | Karlsson et al. |
| 2012/0253287 A1 | 10/2012 | Giambattista et al. |
| 2012/0253288 A1 | 10/2012 | Dasbach et al. |
| 2012/0253289 A1 | 10/2012 | Cleathero |
| 2012/0253290 A1 | 10/2012 | Geertsen |
| 2012/0253314 A1 | 10/2012 | Harish et al. |
| 2012/0259285 A1 | 10/2012 | Schabbach et al. |
| 2012/0265153 A1 | 10/2012 | Jugl et al. |
| 2012/0267761 A1 | 10/2012 | Kim et al. |
| 2012/0271233 A1 | 10/2012 | Bruggemann et al. |
| 2012/0271243 A1 | 10/2012 | Plumptre et al. |
| 2012/0277724 A1 | 11/2012 | Larsen et al. |
| 2012/0283645 A1 | 11/2012 | Veasey et al. |
| 2012/0283648 A1 | 11/2012 | Veasey et al. |
| 2012/0283649 A1 | 11/2012 | Veasey et al. |
| 2012/0283650 A1 | 11/2012 | MacDonald et al. |
| 2012/0283651 A1 | 11/2012 | Veasey et al. |
| 2012/0283652 A1 | 11/2012 | MacDonald et al. |
| 2012/0283654 A1 | 11/2012 | MacDonald et al. |
| 2012/0283660 A1 | 11/2012 | Jones et al. |
| 2012/0283661 A1 | 11/2012 | Jugl et al. |
| 2012/0289907 A1 | 11/2012 | Veasey et al. |
| 2012/0289908 A1 | 11/2012 | Kouyoumjian et al. |
| 2012/0289909 A1 | 11/2012 | Raab et al. |
| 2012/0289929 A1 | 11/2012 | Boyd et al. |
| 2012/0291778 A1 | 11/2012 | Nagel et al. |
| 2012/0296276 A1 | 11/2012 | Nicholls et al. |
| 2012/0296287 A1 | 11/2012 | Veasey et al. |
| 2012/0302989 A1 | 11/2012 | Kramer et al. |

(56) References Cited

U.S. PATENT DOCUMENTS

| | | | |
|---|---|---|---|
| 2012/0302992 | A1 | 11/2012 | Brooks et al. |
| 2012/0310156 | A1 | 12/2012 | Karlsson et al. |
| 2012/0310206 | A1 | 12/2012 | Kouyoumjian et al. |
| 2012/0310208 | A1 | 12/2012 | Kirchhofer |
| 2012/0310289 | A1 | 12/2012 | Bottlang et al. |
| 2012/0316508 | A1 | 12/2012 | Kirchhofer |
| 2012/0323177 | A1 | 12/2012 | Adams et al. |
| 2012/0323186 | A1 | 12/2012 | Karlsen et al. |
| 2012/0325865 | A1 | 12/2012 | Forstreuter et al. |
| 2012/0330228 | A1 | 12/2012 | Day et al. |
| 2013/0006191 | A1 | 1/2013 | Jugl et al. |
| 2013/0006192 | A1 | 1/2013 | Teucher et al. |
| 2013/0006193 | A1 | 1/2013 | Veasey et al. |
| 2013/0006310 | A1 | 1/2013 | Bottlang et al. |
| 2013/0012871 | A1 | 1/2013 | Pommereu |
| 2013/0012884 | A1 | 1/2013 | Pommerau et al. |
| 2013/0012885 | A1 | 1/2013 | Bode et al. |
| 2013/0018310 | A1 | 1/2013 | Boyd et al. |
| 2013/0018313 | A1 | 1/2013 | Kramer et al. |
| 2013/0018317 | A1 | 1/2013 | Bobroff et al. |
| 2013/0018323 | A1 | 1/2013 | Boyd et al. |
| 2013/0018327 | A1 | 1/2013 | Dasbach et al. |
| 2013/0018328 | A1 | 1/2013 | Jugl et al. |
| 2013/0023830 | A1 | 1/2013 | Bode |
| 2013/0030367 | A1 | 1/2013 | Wotton et al. |
| 2013/0030378 | A1 | 1/2013 | Jugl et al. |
| 2013/0030383 | A1 | 1/2013 | Keitel |
| 2013/0030409 | A1 | 1/2013 | Macdonald et al. |
| 2013/0035641 | A1 | 2/2013 | Moller et al. |
| 2013/0035642 | A1 | 2/2013 | Daniel |
| 2013/0035644 | A1 | 2/2013 | Giambattista et al. |
| 2013/0035645 | A1 | 2/2013 | Bicknell et al. |
| 2013/0035647 | A1 | 2/2013 | Veasey et al. |
| 2013/0041321 | A1 | 2/2013 | Cross et al. |
| 2013/0041324 | A1 | 2/2013 | Daniel |
| 2013/0041325 | A1 | 2/2013 | Helmer et al. |
| 2013/0041327 | A1 | 2/2013 | Daniel |
| 2013/0041328 | A1 | 2/2013 | Daniel |
| 2013/0041347 | A1 | 2/2013 | Daniel |
| 2013/0060231 | A1 | 3/2013 | Adlon et al. |

FOREIGN PATENT DOCUMENTS

| | | |
|---|---|---|
| AU | 2009299888 | 4/2010 |
| AU | 2010239762 | 12/2011 |
| AU | 2010242096 | 12/2011 |
| AU | 2010254627 | 1/2012 |
| AU | 2010260569 | 2/2012 |
| AU | 2010303987 | 5/2012 |
| AU | 2010332857 | 7/2012 |
| AU | 2010332862 | 7/2012 |
| AU | 2010337136 | 7/2012 |
| AU | 2010338469 | 7/2012 |
| AU | 2011214922 | 8/2012 |
| AU | 2011221472 | 8/2012 |
| AU | 2011224884 | 10/2012 |
| AU | 2011231570 | 10/2012 |
| AU | 2011231697 | 10/2012 |
| AU | 2011233733 | 10/2012 |
| AU | 2011234479 | 10/2012 |
| AU | 2011238967 | 11/2012 |
| AU | 2011244232 | 11/2012 |
| AU | 2011244236 | 11/2012 |
| AU | 2011244237 | 11/2012 |
| AU | 2011249098 | 11/2012 |
| BR | 0208013 | 3/2004 |
| BR | PI712805 | 10/2012 |
| BR | PI0713802-4 | 11/2012 |
| CA | 2552177 | 7/1999 |
| CA | 02702412 | 12/2008 |
| CN | 101128231 | 2/2008 |
| CN | 101400394 | 4/2009 |
| CN | 101479000 | 7/2009 |
| CN | 101516421 | 8/2009 |
| CN | 101563124 | 10/2009 |
| CN | 101678172 | 3/2010 |
| CN | 101687078 | 3/2010 |
| CN | 101939036 | 1/2011 |
| CN | 102548599 | 7/2012 |
| CN | 102548601 | 7/2012 |
| CN | 102548602 | 7/2012 |
| CN | 102573955 | 7/2012 |
| CN | 102573958 | 7/2012 |
| CN | 102573960 | 7/2012 |
| CN | 102573963 | 7/2012 |
| CN | 102630172 | 8/2012 |
| CN | 102630173 | 8/2012 |
| CN | 102630174 | 8/2012 |
| CN | 102727965 | 10/2012 |
| CN | 102740907 | 10/2012 |
| CN | 102753222 | 10/2012 |
| CN | 102753223 | 10/2012 |
| CN | 102753224 | 10/2012 |
| CN | 102753227 | 10/2012 |
| CN | 102770170 | 11/2012 |
| CN | 102770173 | 11/2012 |
| CN | 102781499 | 11/2012 |
| CN | 102781500 | 11/2012 |
| CN | 102802699 | 11/2012 |
| CN | 102802702 | 11/2012 |
| CN | 102802703 | 11/2012 |
| DE | 102006041809 | 3/2008 |
| DK | 2229201 | 7/2012 |
| DK | 2274032 | 10/2012 |
| DK | 02346552 | 11/2012 |
| EP | 0072057 | 2/1983 |
| EP | 0103664 | 3/1984 |
| EP | 1752174 | 3/1986 |
| EP | 245895 | 11/1987 |
| EP | 361668 | 4/1990 |
| EP | 0518416 | 12/1992 |
| EP | 525525 | 2/1993 |
| EP | 1161961 | 12/2001 |
| EP | 1307012 | 5/2003 |
| EP | 1518575 | 3/2005 |
| EP | 1140260 | 8/2005 |
| EP | 2174682 | 4/2010 |
| EP | 2364742 | 9/2011 |
| EP | 2471564 | 7/2012 |
| EP | 02477681 | 7/2012 |
| EP | 02484395 | 8/2012 |
| EP | 2526987 | 11/2012 |
| ES | 02385630 | 7/2012 |
| ES | 2389866 | 11/2012 |
| FR | 2506161 | 11/1982 |
| FR | 2635009 | 2/1990 |
| GB | 6677523 | 8/1952 |
| GB | 1181037 | 2/1970 |
| GB | 1216813 | 12/1970 |
| GB | 2463034 | 3/2010 |
| IL | 171247 | 8/2012 |
| IL | 198750 | 10/2012 |
| JP | 10-507935 | 8/1998 |
| JP | 11-347121 | 12/1999 |
| JP | 2000-245839 | 9/2000 |
| JP | 2001-523485 | 11/2001 |
| JP | 5016490 | 5/2008 |
| JP | 5026411 | 11/2008 |
| JP | 5033792 | 11/2008 |
| JP | 2009-529395 | 8/2009 |
| JP | 5039135 | 11/2009 |
| JP | 5044625 | 12/2009 |
| JP | 2010-005414 | 1/2010 |
| JP | 2010-046507 | 3/2010 |
| JP | 2012176295 | 9/2012 |
| JP | 2012183322 | 9/2012 |
| JP | 2012520128 | 9/2012 |
| JP | 2012521821 | 9/2012 |
| JP | 2012521825 | 9/2012 |
| JP | 2012521826 | 9/2012 |
| JP | 2012521827 | 9/2012 |
| JP | 2012521828 | 9/2012 |
| JP | 2012521829 | 9/2012 |

(56) References Cited

FOREIGN PATENT DOCUMENTS

| | | |
|---|---|---|
| JP | 2012521830 | 9/2012 |
| JP | 2012521831 | 9/2012 |
| JP | 2012521834 | 9/2012 |
| JP | 2012522547 | 9/2012 |
| JP | 2012-525172 | 10/2012 |
| JP | 2012-525180 | 10/2012 |
| JP | 2012-525185 | 10/2012 |
| JP | 2012523876 | 10/2012 |
| JP | 2012525200 | 10/2012 |
| KR | 20120099022 | 9/2012 |
| KR | 20120099101 | 9/2012 |
| KR | 20120102597 | 9/2012 |
| KR | 20120106754 | 9/2012 |
| KR | 20120106756 | 9/2012 |
| NO | 332622 | 10/2003 |
| NZ | 00590352 | 10/2012 |
| RU | 2462275 | 3/2011 |
| RU | 2459247 | 8/2012 |
| RU | 2011104496 | 8/2012 |
| RU | 2460546 | 9/2012 |
| RU | 2011109925 | 10/2012 |
| WO | WO 88/08724 | 11/1988 |
| WO | WO 91/13299 | 9/1991 |
| WO | WO 91/13430 | 9/1991 |
| WO | WO 92/19296 | 11/1992 |
| WO | WO 94/09839 | 5/1994 |
| WO | WO 94/11041 | 5/1994 |
| WO | WO 95/29720 | 11/1995 |
| WO | WO 95/29730 | 11/1995 |
| WO | WO 96/21482 | 7/1996 |
| WO | WO 97/14455 | 4/1997 |
| WO | WO 97/21457 | 6/1997 |
| WO | WO 97/41907 | 11/1997 |
| WO | WO 97/48430 | 12/1997 |
| WO | WO 98/31369 | 7/1998 |
| WO | WO 98/32451 | 7/1998 |
| WO | WO 9831369 | 7/1998 |
| WO | WO 9832451 | 7/1998 |
| WO | WO 99/03521 | 1/1999 |
| WO | WO 99/10030 | 3/1999 |
| WO | WO 99/22790 | 5/1999 |
| WO | WO 9922789 | 5/1999 |
| WO | WO 00/24441 | 12/1999 |
| WO | WO 99/62525 | 12/1999 |
| WO | WO 9962525 | 12/1999 |
| WO | WO 0006228 | 2/2000 |
| WO | WO 00/29050 | 5/2000 |
| WO | WO 02/89805 | 5/2000 |
| WO | WO 01/93926 | 12/2001 |
| WO | WO 02/083216 | 10/2002 |
| WO | WO 0289805 | 11/2002 |
| WO | WO 03047663 | 6/2003 |
| WO | WO 03/070296 | 8/2003 |
| WO | WO 3068290 | 8/2003 |
| WO | WO 03070296 | 8/2003 |
| WO | WO 03/097133 | 11/2003 |
| WO | WO 03097133 | 11/2003 |
| WO | WO 2004/028598 | 4/2004 |
| WO | WO 2004/041331 | 5/2004 |
| WO | WO 2004/047892 | 6/2004 |
| WO | WO 2004/108194 | 12/2004 |
| WO | WO 2005/002653 | 1/2005 |
| WO | WO 2005/005929 | 1/2005 |
| WO | WO 2005/009515 | 2/2005 |
| WO | WO 2005/053778 | 6/2005 |
| WO | WO 2006/079064 | 7/2006 |
| WO | WO 2006/086899 | 8/2006 |
| WO | WO 2006/130098 | 12/2006 |
| WO | WO 2007/047200 | 4/2007 |
| WO | WO 2007/063342 | 6/2007 |
| WO | WO 2007/100899 | 9/2007 |
| WO | WO 2006/079064 | 11/2007 |
| WO | WO 2007/129106 | 11/2007 |
| WO | WO 2007/131013 | 11/2007 |
| WO | WO 2007/131025 | 11/2007 |
| WO | WO 2007131025 A1 * | 11/2007 |
| WO | WO 2007/143676 | 12/2007 |
| WO | WO 2008/005315 | 1/2008 |
| WO | WO 2008/009476 | 1/2008 |
| WO | WO 2008/089886 | 7/2008 |
| WO | WO 2008/100576 | 8/2008 |
| WO | WO 2008/112472 | 9/2008 |
| WO | WO 2007/104636 | 12/2008 |
| WO | WO 2009049885 | 4/2009 |
| WO | WO 2008/071804 | 8/2009 |
| WO | WO 20091114542 | 9/2009 |
| WO | WO 2009/132778 | 11/2009 |
| WO | WO 2010/003569 | 1/2010 |
| WO | WO 2010/043533 | 4/2010 |
| WO | WO 2010/097116 | 9/2010 |
| WO | WO 2010/108116 | 9/2010 |
| WO | WO 2011/023882 | 3/2011 |
| WO | WO 2011/035877 | 3/2011 |
| WO | WO 2011/036133 | 3/2011 |
| WO | WO 2011/036134 | 3/2011 |
| WO | WO 20111023736 | 3/2011 |
| WO | WO 2011/039163 | 4/2011 |
| WO | WO 2011/039201 | 4/2011 |
| WO | WO 2011/039202 | 4/2011 |
| WO | WO 2011/039207 | 4/2011 |
| WO | WO 2011/039208 | 4/2011 |
| WO | WO 2011/039209 | 4/2011 |
| WO | WO 2011/039211 | 4/2011 |
| WO | WO 2011/039216 | 4/2011 |
| WO | WO 2011/039217 | 4/2011 |
| WO | WO 2011/039218 | 4/2011 |
| WO | WO 2011/039219 | 4/2011 |
| WO | WO 2011/039228 | 4/2011 |
| WO | WO 2011/039231 | 4/2011 |
| WO | WO 2011/039232 | 4/2011 |
| WO | WO 2011/039233 | 4/2011 |
| WO | WO 2011/039236 | 4/2011 |
| WO | WO 2011/040861 | 4/2011 |
| WO | WO 2011/067615 | 6/2011 |
| WO | WO 2011/069936 | 6/2011 |
| WO | WO 2011/073302 | 6/2011 |
| WO | WO 2011/073307 | 6/2011 |
| WO | WO 20111076280 | 6/2011 |
| WO | WO 2011/080092 | 7/2011 |
| WO | WO 2011/081867 | 7/2011 |
| WO | WO 2011/081885 | 7/2011 |
| WO | WO 2011/089206 | 7/2011 |
| WO | WO 2011/089207 | 7/2011 |
| WO | WO 2011/101375 | 8/2011 |
| WO | WO 2011/111006 | 9/2011 |
| WO | WO 2012020084 | 2/2012 |
| WO | WO 2012022771 | 2/2012 |
| WO | WO 2012/090186 | 7/2012 |
| WO | WO 2011/042537 | 8/2012 |
| WO | WO 2011/042540 | 8/2012 |
| WO | WO 2011/043714 | 8/2012 |
| WO | WO 2012/122643 | 9/2012 |

OTHER PUBLICATIONS

Becks et al., "Comparison of Conventional Twice-Daily Subcutaneous Needle Injections to Multiple Jet Injections of Insulin in Insulin-Dependent Diabetes", Clinical and Investigative Medicine, 1981, p. 33B.
Binder, "Absorption of Injected Insulin", ACTA Pharmacological ET Toxicologica, 1969, 27(Supp 2), 3 pages.
Bonetti et al., "An Extended-Release formulation of Methotrexate for Subcutaneous Administration", Cancer Chemotherapy Pharmacology, 1994, 33, 303-306.
Braun et al., "Comparison of the Clinical Efficacy and Safety of Subcutaneous Versus Oral Administration of Methotrexate in Patients with Active Rheumatoid Arthritis", Arthritis and Rheumatism, Jan. 2008, 58(1), pp. 73-81.
Chen et al., "Blood Lipid Profiles and Peripheral Blood Mononuclear Cell Cholesterol Metabolism Gene Expression in Patients with and Without Methotrexate" BMC Medicine, 2011, 9(4), 9 pages.
Chiasson et al., "Continuous Subcutaneous Insulin Infusion (Mill-Hill Infuser) Versus Multiple Injections (Medi-Jector) in the Treat-

(56) References Cited

OTHER PUBLICATIONS ment of Insulin-Dependent Diabetes Mellitus and the Effects of Metabolic Control on Microangiopathy" Diabetes Care, Jul.-Aug. 1984, 7(4), pp. 331-337.
Cohn et al., "Clincal Experience with Jet Insulin Injection in Diabetes Mellitus Therapy: A Clue to the Pathogenesis of Lipodystrophy", Ala. J. Med. Sci., 1974, 11(3), pp. 265-272.
Cowie et al., "Physical and Metabolic Characteristics of Persons with Diabetes", National Institutes of Health/National Institute of Diabetes and Digestive and Kidney Diseases, 1995, 95(1468), pp. 117-120.
European Patent Application No. 03707823.5, Supplementary European Search Report, dated Mar. 30, 2005 with Communication dated Apr. 25, 2005 regarding Proceeding Further with the European Patent Application Pursuant to Article 96(1), and Rule 51(1) EPC, 3 pages.
European Patent Application No. 00976612.2, Communication Pursuant to Article 96(2) EPC, dated May 10, 2004, 5 pages.
Hingson et al., "A Survey of the Development of Jet Injection in Parenteral Therapy", Nov./Dec. 1952, 31(6), pp. 361-366.
Hoekstra et al., Bioavailability of Higher Dose Methotrexate Comparing Oral and Subcutaneous Administration in Patients with Rheumatoid Arthritis, The Journal of Rheumatology, 2004, 31(4), pp. 645-648.
International Patent Application No. PCT/US2012/46742, International Search Report and Written Opinion dated Nov. 16, 2012, 11 pages.
International Patent Application No. PCT/US20091052835, International Search Report dated Mar. 15, 2010, 5 pages.
International Patent Application No. PCT/US20131029085, International Search Report dated May 13, 2013, 2 pages.
International Patent Application No. PCT/US20101028011, International Search Report, dated Jun. 29, 2010, 5 pages.
International Patent Application No. PCT/US20091036682, International Search Report, dated Jul. 7, 2009, 5 pages.
International Patent Application No. PCT/US2007/068010, International Search Report, dated Sep. 24, 2007, 3 pages.
International Patent Application No. PCT/US03/03917, International Search Report, dated Nov. 26, 2003, 1 page.
Jansen et al., Methotrexaat Buiten de Kliniek, Pharmaceutisch Weekblad, Nov. 1999, 134(46), pp. 1592-1596.
Japanese Patent Application No. 2007-552367, Office Action dated Apr. 9, 2011.
Katoulis et al., Efficacy of a New Needleless Insulin Delivery System Monitoring of Blood Glucose Fluctuations and Free Insulin Levels, The International Journal of Artificial Organs, 1989, 12(5), 333-339.
Kurnik et al., "Bioavailability of Oral vs. Subcutaneous low-dose Methotrexate in Patients with Crohn's Disease", Aliment Pharmacol Ther., Apr. 2003, 18, pp. 57-63.
Malone et al., "Comparison of Insulin Levels After Injection by Jet Stream and Disposable Insulin Syringe", Diabetes Care, Nov.-Dec. 1986, 9(6), 637-640.
"The Historical Development of Jet Injection and Envisioned Uses in Mass Immunization and Mass Therapy Based Upon Two Decades' Experience", Military Medicine, Jun. 1963, 128, pp. 516-524.

Pehling et al, "Comparison of Plasma Insulin Profiles After Subcutaneous Administration of Insulin by Jet Spray and Conventional Needle Injection in Patients with Insulin-Dependent Diabetes Mellitus", Mayo Clin. Proc., Nov. 1984, 59, pp. 751-754.
Reiss et al., "Atheroprotective Effects of Methotrexate on Reverse Cholesterol Transport Proteins and Foam Cell Transformation in Human THP-1 Monocyte/Macrophages", Arthritis and Rheumatism, Dec. 2008, 58(12), pp. 3675-3683.
Taylor et al., "Plasma Free Insulin Profiles After Administration of Insulin by Jet and Conventional Syringe Injection", Diabetes Care, May-Jun. 1981, 4(3), 337-339.
Weller et al., "Jet Injection of Insulin vs the Syringe-and-Needle Method", JAMA, Mar. 1966, 195(10), pp. 844-847.
Westlake et al., "The Effect of Methotrexate on Cardiovascular Disease in Patients with Rheumatoid Arthritis: A Systematic Literature Review", Rheumatology, Nov. 2009, 49, pp. 295-307.
Worth, "Jet Injection of Insulin: Comparison with Conventional Injection by Syringe and Needle", British Medical Journal, Sep. 1980, 281, pp. 713-714.
International Patent Application No. PCT/US2013/029085, Written Opinion, dated May 13, 2013, 5 pages.
International Patent Application No. PCT/US2010/028011, Written Opinion, dated Jun. 29, 2010, 5 pages.
Zachheim et al., "Subcutaneous Administration of Methotrexate", Journal of the American Academy of Dermatology, 1992, 26(6), p. 1008.
Halle et al., "Twice-Daily Mixed Regular and NPH Insulin Injections with New Jet Injector Versus Conventional Syringes: Pharmacokinetics of Insulin Absorption", Diabetes Care, May-Jun. 1986 9(3), pp. 279-282.
International Patent Application No. PCT/US2012/046639, International Search Report and Written Opinion dated Apr. 22, 2013, 8 pages.
Glynn-Barnhart et al., "Pharmacotherapy: The Journal of Human Pharmacology and Drug Therapy", 1992, 12(5), abstract only, 2 pages.
Hamilton et al., "Why Intramuscular Methotrexate May be More Efficacious Than Oral Dosing in Patients with Rheumatoid Arthritis", British Journal of Rheumatology, 1997, 36(1), pp. 86-90.
Stamp et al., "Effects of Changing from Oral to Subcutaneous Methotrexate on Red Blood Cell Methotrexate Polyglutamate Concentrations and Disease Activity in Patients with Rheumatoid Arthritis", The Journal of Rheumatology, 2011, 38(12), 2540-2547.
Tukova et al., "Methotrexate Bioavailability after Oral and Subcutaneous Administration in Children with Juvenile Idiopathic Arthritis", Clinical and Experimental Rheumatology, 2009, 27, 1047-1053.
Wright et al., "Stability of Methotrexate Injection in Prefilled Plastic Disposable Syringes", International Journal of Pharmaceutics, Aug. 1988, 45(3), 237-244.
Greenspan et al., "Stable Testosterone Levels Achieved with Subcutaneous Testosterone Injections", The aging Male, Mar. 2006, 9(1), 70 pages.

\* cited by examiner

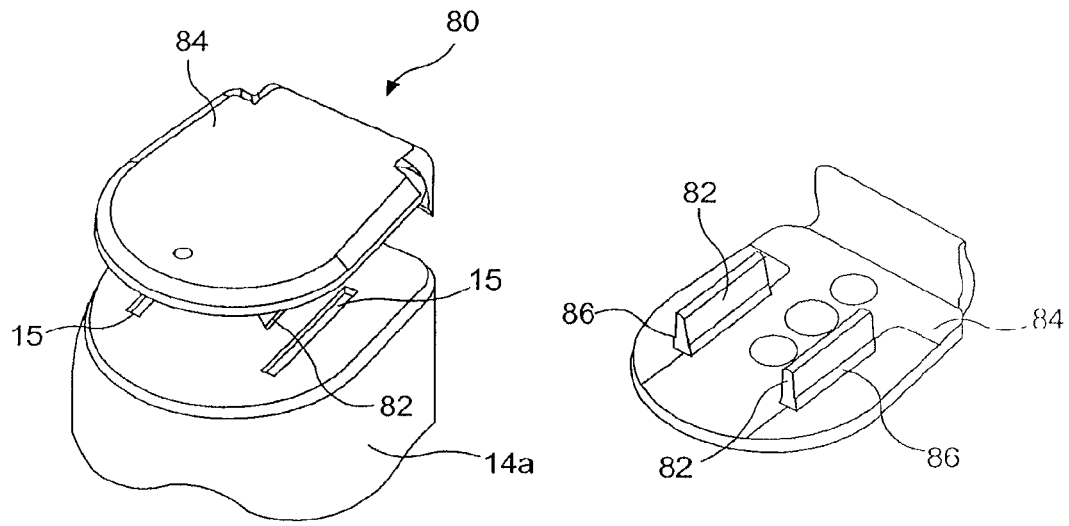
F I G. 4a
F I G. 4b
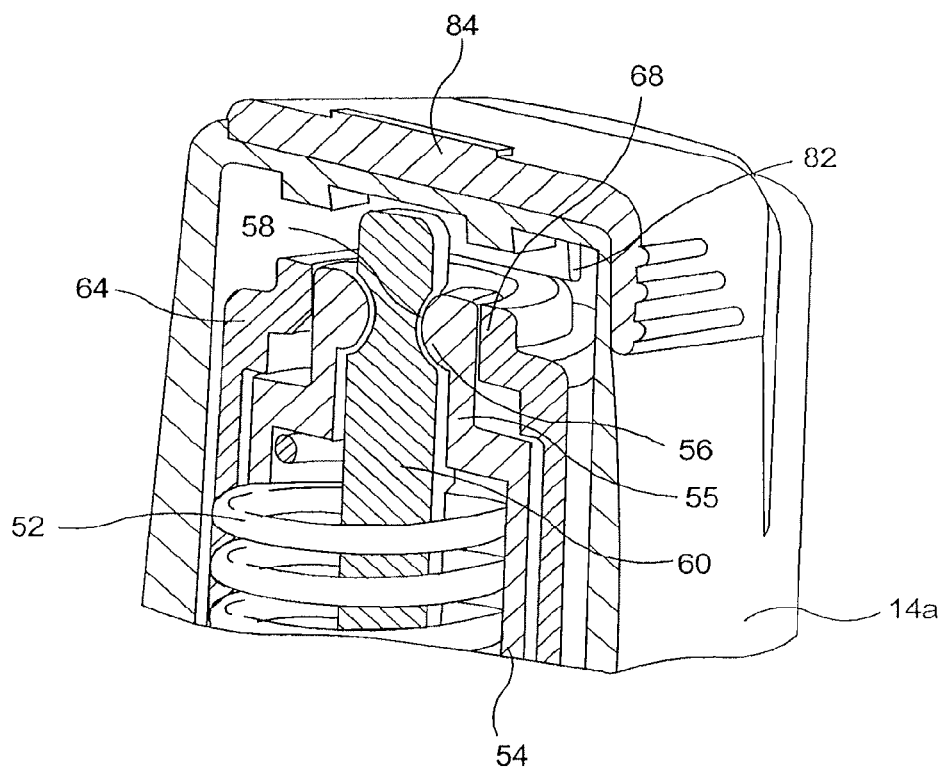
F I G. 5

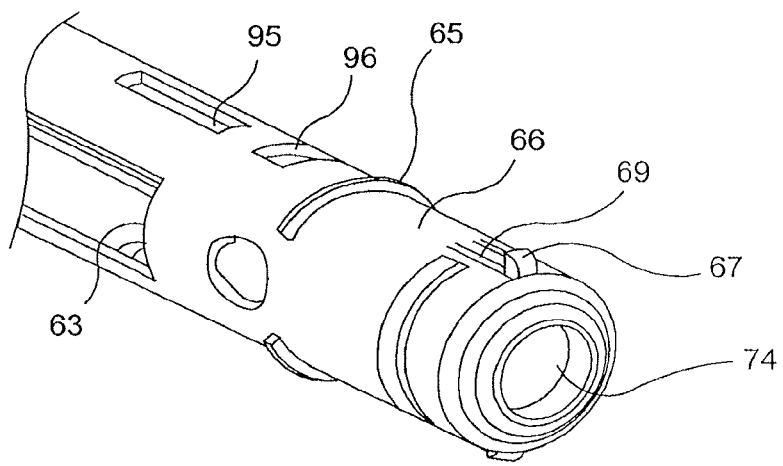
F I G. 8
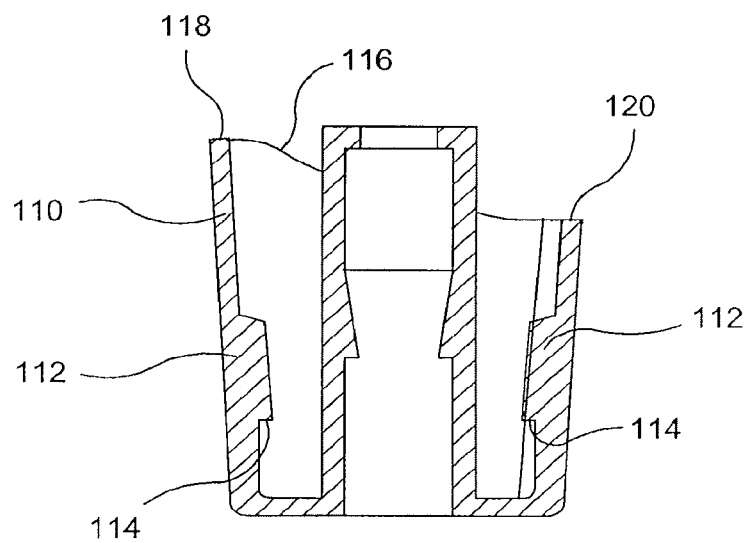
F I G. 9

HAZARDOUS AGENT INJECTION SYSTEM

CROSS REFERENCE TO RELATED APPLICATIONS

This application is a continuation of currently pending U.S. patent application Ser. No. 13/758,913, filed 4 Feb. 2013, which in turn is a continuation of U.S. patent application Ser. No. 13/607,659, filed 7 Sep. 2012, issued as U.S. Pat. No. 8,480,613 on Jul. 9, 2013, which in turn is a continuation of U.S. patent application Ser. No. 13/257,555, filed 6 Mar. 2012, issued as U.S. Pat. No. 8,579,865 on Nov. 12, 2013, which in turn is a U.S. National Stage Entry of the expired International Patent Application No. PCT/US2010/028011, filed 19 Mar. 2010, which in turn claims benefit of priority from expired U.S. Provisional Patent Application No. 61/162,114, filed 20 Mar. 2009, all which are incorporated by reference herein in their entirety.

FIELD

The disclosure relates to injection of hazardous agents.

BACKGROUND

Since the late 1980's hazardous agents, such as cytotoxic agents have been useful in managing and treating a number of diseases such as rheumatoid arthritis (and other autoimmune diseases), juvenile rheumatoid arthritis, psoriatic arthritis, systemic lupus erythematosus, steroid resistant polymyositis or dermatomyositis, Wegener's granulomatosis, polyarteritis nodosa, and some forms of vasculitis. Hazardous agents tend to exhibit side effects, however, that are harmful or toxic to the subject. Many of these side effects occur when hazardous agents are administered orally, but the oral form is generally the preferred method of delivery of these agents due to its ease of use.

In addition to increased toxicity, variable and reduced bioavailability has been observed for some hazardous agents, such as methotrexate, that are orally administered. These limitations are particularly demonstrated when the oral dosing is escalated beyond 15 mg per week. It has been suggested that with parenteral administration, such as by injection, more predictable, reproducible and complete bioavailability along with better therapeutic results could be achieved, particularly at higher dosages.

Only about 7% of the prescriptions for methotrexate written by rheumatologists are for an injectable formulation. Reasons for prescribing methotrexate injections are usually to improve bioavailability or to alleviate side effects. Physicians have expressed interest in increasing the number of prescriptions for cytotoxic agent injections, and particularly injections for home use and administration by a patient. This is generally not considered feasible because it is not possible to ensure that patients can reliably and repeatably draw an accurate dose from vials and correctly administer the product by subcutaneous (SC) injection, especially with agents used to treat patients suffering from certain debilitating diseases. Additionally, the toxicity of hazardous agents increases the risk that non-users of the injections will come into contact with the cytotoxic agents in a home setting. Insufficient data exists on the effect of low dose, chronic exposure to hazardous agents that are, or may be, candidates for home use or self-injection. In the absence of such information, practice guidelines direct one to assume a high degree risk for injectable hazardous agents such as methotrexate, with the recommendation of formal directives and risk assessments, including formal training and mitigation strategies, to minimize risk (see Oliver, S., and Livermore, P., *Administering subcutaneous methotrexate for inflammatory arthritis: RCN guidance for nurses*, 2004; Royal College of Nursing, Wyeth, Publication Code 002 269). Specific directives include: preparation of syringes in dedicated pharmacies with aseptic preparation areas; administration performed in specific locations and only by adequately trained personnel; spillage kits located proximal to use areas; accounting for all who may be at risk in the event of an accident; and audits to assess compliance and execution of risk mitigation strategies. Because of the need for such directives, and thus the large number of precautions that must be learned and followed in order to safely inject a hazardous agent, it is presently thought that it is not practical for hazardous agents, and particularly methotrexate, to be self-injected by a patient outside of a clinical setting or without the assistance of a health care provider.

SUMMARY

Thus, injector devices that allow for the safe self-administration of hazardous agents are useful. In some embodiments, hazardous agents can include, without limitation, toxic agents, cytotoxic agents, highly potent agents, agents that have profound physiological effects at low doses, analgesics, immunomodulating agents, IL-1 receptor antagonists, IL-2 alpha receptor antagonists, anti-rejection compounds, hormonal agents, prostaglandins, sedatives, anticholinergic agents, Parkinsons disease drugs, expensive agents, neuroleptic agents, tissue necrosis factor (TNF) blockers, and other dangerous agents. Such injector devices would eliminate the risk of inadvertent contact of such agents to the subject and would also protect to non-users from exposure or contact with the hazardous agent(s). Examples of cytotoxic agents include, without limitation, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, and derivatives thereof. Examples of highly potent agents include, without limitation, steroids such as dexamethasone, progesterone, somatostatin, and analogues thereof; biologically active peptides such as teriparatide; and anticholinergics such as scopolamine. Examples of agents that have profound physiological effects at low doses include, without limitation, antihypertensives and/or blood pressure down regulators. Examples of analgesics include, without limitation, fentanyl, fentanyl citrate, morphine, meperidine, and other opioids. Examples of immunomodulating agents include, without limitation, adalimumab (anti-tissue necrosis factor monoclonal antibody or anti-TNF). Examples of IL-1 receptor antagonists include, without limitation, anakinra. Examples of IL-2 alpha receptor antagonists include, without limitation, daclizumab and basiliximab. Examples of anti-rejection compounds include, without limitation, azathioprine, cyclosporine, and tacrolimus. Examples of hormonal agents include, without limitation, testosterone, estrogen, growth hormone, insulin, thyroid hormone, follicle stimulating hormone (FSH), epinephrine/adrenaline, progesterone, parathyroid hormone, gonadotrophin releasing hormone (GHRH), leutinizing hormone releasing hormone (LHRH), other hormones such as those where contact with the hormone by members of the opposite sex can lead to side effects, and derivatives thereof. Examples of prostaglandins include, without limitation, gamma-linolenic acid, docosahexanoic acid, arachidonic acid and eicosapentaenoic acid. Examples of sedatives include, without limitation, barbiturates such as amobarbital, pentobarbital, secobarbital, and phenobarbitol; benzodiazepines such as clonazepam, diazepam, estazolam, flunitrazepam, lorazepam, midazolam, nitrazepam, oxazepam, triazolam, temazepam, chlordiazepoxide, and alprazolam; herbal sedatives such as ashwagandha, duboisia hopwoodii, prosanthera striatiflora, kava (piper methysticum), mandrake, valerian, and marijuana; non-benzodiazepine sedatives (a.k.a. "Z-drugs") such as eszopiclone, zaleplon, zolpidem, zopiclone; antihistamines such as diphenhydramine, dimenhydrinate, doxylamine, and promethazine; and other sedatives such as chloral hydrate. Examples of anticholinergic agents include, without limitation, dicyclomine, atropine, ipratropium bromide, oxitropium bromide, and tiotropium. Examples of Parkinson's disease drugs include, without limitation, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, and lisuride. Examples of expensive agents include, without limitation, human growth hormone and erythropoietin. Examples of neuroleptic agents includes, without limitation, antipsychotics; butyrophenones such as haloperidol and droperidol; phenothiazines such as chlorpromazine, fluphenazine, perphenazine, prochlorperazine, thioridazine, trifluoperazine, mesoridazine, periciazine, promazine, triflupromazine, levomepromazine, promethazine, and pimozide; thioxanthenes such as chlorprothixene, clopenthixol, flupenthixol, thiothixene, and zuclopenthixol; atypical antipsychotics such as clozapine, olanzapine, risperidone, quetiapine, ziprasidone, amisulpride, asenapine, paliperidone, iloperidone, zotepine, and sertindole; and third generation antipsychotics such as aripiprazole and bifeprunox. Examples of TNF blockers includes, without limitation, etanercept.

In some embodiments, the hazardous agent can be selected from botulinum toxin, injectable gold, 6-mercaptopurine, 6-thioinosinie acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, dexamethasone, progesterone, somatostatin, analogues of dexamethasone, analogues of progesterone, analogues of somatostatin, teriparatide, scopolamine, antihypertensives, blood pressure down regulators, fentanyl, fentanyl citrate, morphine, meperidine, other opioids, adalimumab (anti-tissue necrosis factor monoclonal antibody or anti-TNF), anakinra, daclizumab, basiliximab, azathioprine, cyclosporine, tacrolimus, testosterone, estrogen, growth hormone, insulin, thyroid hormone, follicle stimulating hormone (FSH), epinephrine/adrenaline, gamma-linolenic acid, docosahexanoic acid, arachidonic acid, eicosapentaenoic acid, amobarbital, pentobarbital, secobarbital, phenobarbitol, clonazepam, diazepam, estazolam, flunitrazepam, lorazepam, midazolam, nitrazepam, oxazepam, triazolam, temazepam, chlordiazepoxide, alprazolam, ashwagandha, duboisia hopwoodii, prosanthera striatiflora, kava (piper methysticum), mandrake, valerian, marijuana, eszopiclone, zaleplon, zolpidem, zopiclone, diphenhydramine, dimenhydrinate, doxylamine, promethazine, chloral hydrate, dicyclomine, atropine, ipratropium bromide, oxitropium bromide, tiotropium, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, lisuride, human growth hormone, erythropoietin, haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, aripiprazole, bifeprunox, etanercept, derivatives of any of the foregoing, and combinations of any of the foregoing.

The hazardous agent can include a pharmaceutically acceptable salt, solvate, hydrate, oxide or N-oxide thereof. In some embodiments, the hazardous agent is a hazardous agent or a pharmaceutically acceptable salt, solvate, hydrate, oxide or N-oxide thereof. In some embodiments the hazardous agent is a compound of formula (I):

or a pharmaceutically acceptable salt, solvate, hydrate, oxide or N-oxide thereof. In some embodiments, the hazardous agent is methotrexate.

In one aspect, the present disclosure relates to powered injectors for the safe self injection of one or more hazardous agents in less than about 5 seconds. In various aspects, the powered injectors may be utilized by patients to self-inject hazardous agents. In certain embodiments, the powered injectors are needle assisted. In certain embodiments, the powered injectors are needle-free. In certain embodiments, the powered injectors may utilize pressure sufficient to deliver a therapeutically effective amount of one or more hazardous agents completely and quickly, in less than about 5 seconds. In certain embodiments, the powered injectors may comprise a pre-filled syringe for containing the one or more hazardous agents. In certain embodiments, the powered injectors may comprise a syringe sleeve to contain the pre-filled syringe and to minimize syringe movement from injection force to decrease syringe shock. In certain embodiments, the powered injectors may comprise a needle exposure control element. In certain embodiments, the powered injectors may comprise a safe means to prevent hazards after injection that may arise from the hazardous agents directly and/or from body fluids contacted with hazardous agents. In certain embodiments, the powered injectors may comprise a safe means to prevent hazards after injection that may arise from residual hazardous agents present in injector components that contact the hazardous agents.

In another aspect, the present disclosure relates to methods for safely injecting one or more hazardous agents into a subject. In certain embodiments, the methods utilize a powered injection system having a pre-filled syringe containing at least one hazardous agent that allows the subject to safely self-administer the agent in less than about 5 seconds. In certain embodiments, the methods include using a spring-powered injection device comprising a needle with means to control needle exposure during the injection such that the exposure is sufficient to deliver one or more hazardous agents to the appropriate tissue site. In certain embodiments, the injector may have a spring sufficiently powerful to deliver one or more hazardous agents in less than about 2 seconds. In certain embodiments, the injector may have a syringe sleeve that minimizes syringe movement as a result of the injection spring action. In certain embodiments, the injector may have means for controlling needle exposure that locks following injection to prevent needle re-exposure. In certain embodiments, the injector may have a liquid tight cap that covers the means for controlling needle exposure, that allows for removal of the cap when preparing injector for injection, and that locks to the injector when re-attached following injection to provide a sealed container.

In several aspects, the present disclosure relates to an injection system. In various aspects, the injection system comprises a powered injector configured to inject one or more medicaments in less than about 5 seconds, and one or more medicaments. In various aspects, the powered injector comprises a container configured to contain a medicament, a delivery member associated with the container for injecting the medicament, a firing mechanism configured to expel the medicament from the fluid chamber through the delivery member for injecting the medicament, an energy source associated with the firing mechanism to power the firing mechanism for causing the injection, and a trigger mechanism associated with the firing mechanism to activate the firing mechanism. In some embodiments, the powered injector can be an autoinjector configured to inject one or more medicaments in less than about 5 seconds. In some embodiments, the powered injector can be a jet injector. In some embodiments, the jet injector can be needle-assisted. In some embodiments, the jet injector can be needle-free.

In another aspect, the present disclosure relates to an injection system, which can include a powered injector configured to inject one or more hazardous agents in less than about 5 seconds, and one or more hazardous agents. One embodiment of a powered injector has a container configured to contain a hazardous agent, a delivery member associated with the container for injecting the hazardous agent, a firing mechanism configured to expel the hazardous agent from the container through the delivery member for injecting the medicament, an energy source associated with the firing mechanism to power the firing mechanism for causing the injection, and a trigger mechanism associated with the firing mechanism to activate the firing mechanism. The powered injector can be a single-shot injector, and can be pre-filled with the hazardous agent, or alternatively can be fillable or take cartridges that can be loaded into the injector for firing. Other embodiments can have adjustable dosages.

In another embodiment, the present disclosure relates to an injection system which can include a jet injector and a compound of formula (I). One embodiment of a jet injector has a container configured to contain a hazardous agent comprising a compound of formula (I), a injection outlet member associated with the container and defining an injection outlet configured for injecting the hazardous agent, a firing mechanism configured to expel the hazardous agent from the fluid chamber through the injection outlet for injecting the hazardous agent, an energy source associated with the firing mechanism to power the firing mechanism jet injecting the hazardous agent from the injection outlet, and a trigger mechanism associated with the firing mechanism to activate the firing mechanism. The jet injector can be a single-shot injector, and can be pre-filled with the hazardous agent, or alternatively can be finable or take cartridges that can be loaded into the injector for firing. Other embodiments have adjustable dosages. In some embodiments, the hazardous agent is methotrexate or a pharmaceutically acceptable salt, solvate, hydrate, oxide or N-oxide thereof.

In another embodiment the present disclosure relates to an injection system for the treatment of inflammatory diseases. In one embodiment, the injection system includes a jet injector and a therapeutically effective amount of a medicament, wherein the therapeutically effective amount of medicament is sufficient to treat an inflammatory disease. In one embodiment, the jet injector has a container configured to contain the medicament; an injection outlet member associated with the container for injecting the medicament; a firing mechanism configured to expel the medicament from the fluid chamber through the outlet member for injecting the medicament; an energy source associated with the firing mechanism to power the firing mechanism jet injecting the medicament from the injection outlet; and a trigger mechanism associated with the firing mechanism to activate the firing mechanism. In some embodiments, the medicament is a hazardous agent. In some embodiments, the medicament is methotrexate or a pharmaceutically acceptable salt, solvate, hydrate, oxide or N-oxide thereof.

In another embodiment the present disclosure relates to kits. In one embodiment, the kits can comprise a jet injector configured to inject a therapeutically effective amount of one or more hazardous agents less than about 5 seconds, a therapeutically effective amount of a hazardous agent, and instructions for using the jet injector and the hazardous agent. In some embodiments, the jet injector comprises a container configured to contain the hazardous agent, an injection outlet member associated with the container for injecting the hazardous agent, a firing mechanism configured to expel the hazardous agent from the fluid chamber through the outlet member for injecting the hazardous agent, an energy source associated with the firing mechanism to power the firing mechanism jet injecting the hazardous agent from the injection outlet, and a trigger mechanism associated with the firing mechanism to activate the firing mechanism. In one embodiment, the kits comprise a jet injector, a therapeutically effective amount of methotrexate contained in the jet injector, and instructions for using the jet injector to inject the methotrexate into a subject.

BRIEF DESCRIPTION OF THE DRAWINGS

These and other objects, features and advantages of the disclosure will be apparent from a consideration of the following non-limiting detailed description considered in conjunction with the drawing figures, in which:

FIGS. 4A and 4B are perspective views of a safety member used in connection with the injection device of FIG. 1;

FIG. 5 is an additional cross-sectional view of the device of FIG. 1 in the safety state;

FIG. 8 is a perspective view of a needle guard according to an embodiment of the injector of FIG. 1;

FIG. 9 is a cross-sectional view of the cap shown in FIG. 1;

DETAILED DESCRIPTION

Definitions

Figure 1:
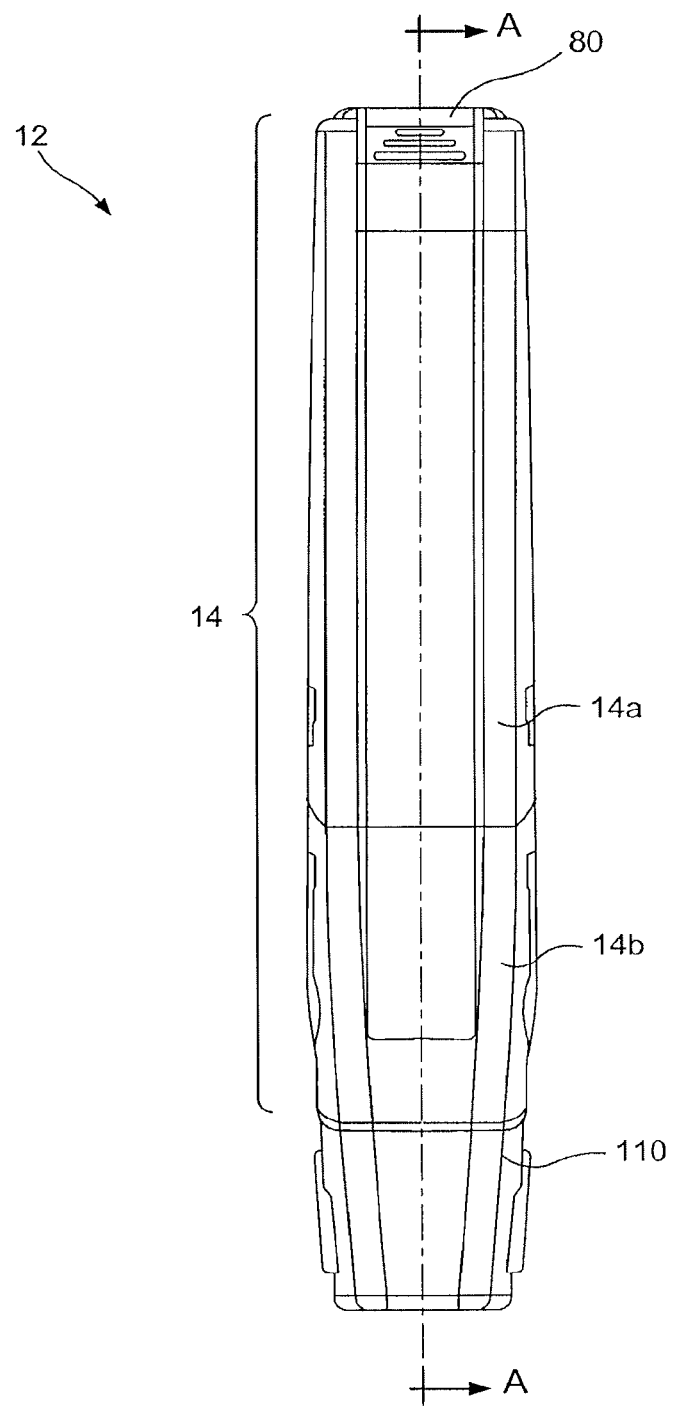
FIG. 1 is a side view of an injection device according to an embodiment of the present disclosure.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cylcohexylcarbonyl, cyclohexylmethylcarbonyl, benzoyl, benzylcarbonyl and the like.

"Acylamino" (or alternatively "acylamido") refers to a radical —NR'C(O)R, where R' and R are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino (i.e., acetamido), cyclohexylcarbonylamino, cyclohexylmethyl-carbonyl amino, benzoylamino (i.e., benzamido), benzylcarbonylamino and the like.

"Alkoxy" refers to a radical —OR where R represents an alkyl or cycloalkyl group as defined herein. Representative examples include, but are not limited to, methoxy, ethoxy, propoxy, butoxy, cyclohexyloxy and the like.

"Alkoxycarbonyl" refers to a radical —C(O)-alkoxy, where alkoxy is as defined herein.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms, in some embodiments, from 1 to 10 carbon atoms.

"Alkylamino" means a radical —NHR where R represents an alkyl or cycloalkyl group as defined herein. Representative examples include, but are not limited to, methyl amino, ethylamino, 1-methylethylamino, cyclohexyl amino and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylthio" refers to a radical —SR where R is an alkyl or cycloalkyl group as defined herein. Representative examples include, but are not limited to methylthio, ethylthio, propylthio, butylthio and the like.

"Amino" refers to the radical —NH2.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms, in some embodiments between 6 to 12 carbon atoms.

"Arylalkyl" refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$), in some embodiments, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Aryloxy" refers to a radical —OR where R represents an aryl group as defined herein.

"AUC" is the area under a curve representing the concentration of a compound, such as a hazardous agent as defined herein, or metabolite thereof in the blood or plasma of a patient as a function of time following administration of the compound to the patient. For example; the administered compound can be a hazardous agent as defined herein. The AUC may be determined by measuring the concentration of a compound or metabolite thereof in blood using methods such as liquid chromatography-tandem mass spectrometry (LC/MS/MS), at various time intervals, and calculating the area under the blood or plasma concentration-versus-time curve. The concentration versus time curve is also referred to as the pharmacokinetic profile. Suitable methods for calculating the AUC from a compound concentration-versus-time curve are well known in the art. For example, an AUC for the hazardous agent methotrexate may be determined by measuring the concentration of methotrexate in the blood of a patient following administration of methotrexate to the patient. $AUC_{0-24}$ is the area under the curve from administration (time 0) to 24 hours following administration. $AUC_{ss,24}$ is the area under the curve over a 24 hour period following a dosing regimen administered over a period of days (steady state).

"Bioavailability" refers to the amount of a compound, such as, for example, a hazardous agent, that reaches the systemic circulation of a patient following administration of the compound to the patient and can be determined by evaluating, for example, the blood or plasma concentration for the compound. For example, the administered compound can be a hazardous agent as defined herein.

"Compounds" of the present disclosure include compounds within the scope of formula (I). Compounds may be identified either by their chemical structure and/or chemical name. When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, unless specifically indicated, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. For example, resolution of the enantiomers or diastereomers may be accomplished by conventional methods such as crystallization in the presence of a resolving agent, or chromatography, using a chiral high-pressure liquid chromatography (HPLC) column.

The compounds as disclosed herein may also exist in several tautomeric forms including the enol form, the keto form, and mixtures thereof. Accordingly, the chemical structure depicted herein encompasses all possible tautomeric forms of the illustrated compounds. Compounds of the present disclosure also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms and as oxides or N-oxides. In general, compounds may be free acid, hydrated, solvated, oxides, or N-oxides. Compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing. Compounds also include solvates.

"Cycloalkyl" refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, the cycloalkyl group is $(C_3-C_{10})$ cycloalkyl, in some embodiments $(C_3-C_7)$ cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Dialkylamino" means a radical —NRR' where R and R' independently represent an alkyl or cycloalkyl group as defined herein. Representative examples include, but are not limited to, dimethylamino, methylethylamino, di-(1-methylethyl)amino, (cyclohexyl)(methyl)amino, (cyclohexyl)(ethyl)amino, (cyclohexyl)(propyl)amino and the like.

"Formula (I)" includes the methotrexate derivative (I), pharmaceutically acceptable salts thereof, pharmaceutically acceptable solvates of any of the foregoing, pharmaceutically acceptable hydrates of any of the foregoing, pharmaceutically acceptable oxides of any of the foregoing, and crystalline forms of any of the foregoing. Formula (I) is used interchangeably with a compound of formula (I). In certain embodiments, a compound of formula (I) can be a free acid. In certain embodiments, a compound of formula (I) can be a pharmaceutically acceptable salt.

"Halo" means fluoro, chloro, bromo, or iodo.

"Hazardous Agent(s)" means any one or more medications that are toxic agents, cytotoxic agents and/or other dangerous agents that may cause serious effects upon contact with a subject as well as highly potent agents, agents that have profound physiological effects at low doses, analgesics, immunomodulating agents, IL-1 receptor antagonists, IL-2 alpha receptor antagonists, anti-rejection compounds, hormonal agents, prostaglandins, sedatives, anticholinergic agents, Parkinsons disease drugs, expensive agents, neuroleptic agents, tissue necrosis factor (TNF) blockers, and other dangerous agents. In this disclosure, the term "hazardous agent(s)" is used interchangeably with "agent" and "medicament". Hazardous agents include, without limitation, antineoplastic cytotoxic medications, anesthetic agents, anti-viral agents, potent peptide compounds, toxic agents, cytotoxic agents, highly potent agents, agents that have profound physiological effects at low doses, analgesics, immunomodulating agents, IL-1 receptor antagonists, IL-2 alpha receptor antagonists, anti-rejection compounds, hormonal agents, prostaglandins, sedatives, anticholinergic agents, Parkinsons disease drugs, expensive agents, neuroleptic agents, tissue necrosis factor (TNF) blockers, and other dangerous agents. toxic agents, cytotoxic agents, highly potent agents, agents that have profound physiological effects at low doses and other dangerous agents.

Examples of highly potent agents include, without limitation, steroids such as dexamethasone, progesterone, somatostatin, and analogues thereof; biologically active peptides such as teriparatide; and anticholinergics such as scopolamine. Examples of agents that have profound physiological effects at low doses include, without limitation, antihypertensives and/or blood pressure down regulators. Examples of analgesics include, without limitation, Fentanyl, fentanyl citrate, morphine, meperidine, and other opioids. Examples of immunomodulating agents include, without limitation, adalimumab (anti-tissue necrosis factor monoclonal antibody or anti-TNF). Examples of IL-1 receptor antagonists include, without limitation, anakinra. Examples of IL-2 alpha receptor antagonists include, without limitation, daclizumab and basiliximab. Examples of anti-rejection compounds include, without limitation, azathioprine, cyclosporine, and tacrolimus. Examples of hormonal agents include, without limitation, testosterone, estrogen, growth hormone, insulin, thyroid hormone, follicle stimulating hormone (FSH), epinephrine/adrenaline, progesterone, parathyroid hormone, gonadotrophin releasing hormone (GHRH), leutinizing hormone releasing hormone (LHRH), other hormones such as those where contact with the hormone by members of the opposite sex can lead to side effects, and derivatives thereof. Examples of prostaglandins include, without limitation, gamma-linolenic acid, docosahexanoic acid, arachidonic acid and eicosapentaenoic acid. Examples of sedatives include, without limitation, barbiturates such as amobarbital, pentobarbital, secobarbital, and phenobarbitol; benzodiazepines such as clonazepam, diazepam, estazolam, flunitrazepam, lorazepam, midazolam, nitrazepam, oxazepam, triazolam, temazepam, chlordiazepoxide, and alprazolam; herbal sedatives such as ashwagandha, duboisia hopwoodii, prosanthera striatiflora, kava (piper methysticum), mandrake, valerian, and marijuana; non-benzodiazepine sedatives (a.k.a. "Z-drugs") such as eszopiclone, zaleplon, zolpidem, zopiclone; antihistamines such as diphenhydramine, dimenhydrinate, doxylamine, and promethazine; and other sedatives such as chloral hydrate. Examples of anticholinergic agents include, without limitation, dicyclomine, atropine, ipratropium bromide, oxitropium bromide, and tiotropium. Examples of Parkinson's disease drugs include, without limitation, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, and lisuride. Examples of expensive agents include, without limitation, human growth hormone and erythropoietin. Examples of neuroleptic agents includes, without limitation, antipsychotics; butyrophenones such as haloperidol and droperidol; phenothiazines such as chlorpromazine, fluphenazine, perphenazine, prochlorperazine, thioridazine, trifluoperazine, mesoridazine, periciazine, promazine, triflupromazine, levomepromazine, promethazine, and pimozide; thioxanthenes such as chlorprothixene, clopenthixol, flupenthixol, thiothixene, and zuclopenthixol; atypical antipsychotics such as clozapine, olanzapine, risperidone, quetiapine, ziprasidone, amisulpride, asenapine, paliperidone, iloperidone, zotepine, and sertindole; and third generation antipsychotics such as aripiprazole and bifeprunox. Examples of TNF blockers includes, without limitation, etanercept.

Hazardous agents include pharmaceutically acceptable salts, solvates, hydrates, oxides or N-oxides. In some embodiments the hazardous agent is a cytotoxic compound or a pharmaceutically acceptable salt, solvate, hydrate, oxide or N-oxide thereof. In some embodiments the hazardous agent is a compound of formula (I):

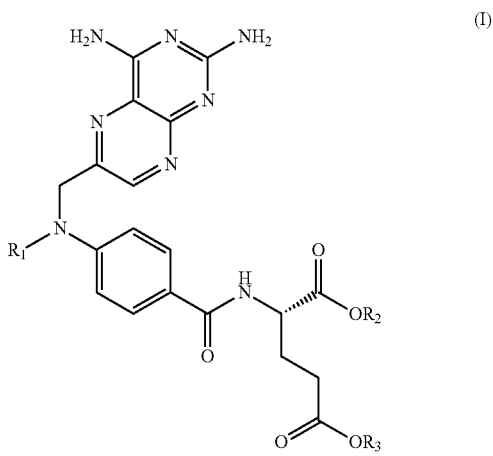

or a pharmaceutically acceptable salt, solvate, hydrate, oxide or N-oxide thereof. In some embodiments, the medicament is methotrexate.

In some embodiments, the hazardous agent can be selected from botulinum toxin, injectable gold, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, dexamethasone, progesterone, somatostatin, analogues of dexamethasone, analogues of progesterone, analogues of somatostatin, teriparatide, scopolamine, antihypertensives, blood pressure down regulators, fentanyl, fentanyl citrate, morphine, meperidine, other opioids, adalimumab (anti-tissue necrosis factor monoclonal antibody or anti-TNF), anakinra, daclizumab, basiliximab, azathioprine, cyclosporine, tacrolimus, testosterone, estrogen, growth hormone, insulin, thyroid hormone, follicle stimulating hormone (FSH), epinephrine/adrenaline, gamma-linolenic acid, docosahexanoic acid, arachidonic acid, eicosapentaenoic acid, amoharbital, pentobarbital, secobarbital, phenobarbitol, clonazepam, diazepam, estazolam, flunitrazepam, lorazepam, midazolam, nitrazepam, oxazepam, triazolam, temazepam, chlordiazepoxide, alprazolam, ashwagandha, duboisia hopwoodii, prosanthera striatiflora, kava (piper methysticum), mandrake, valerian, marijuana, eszopiclone, zaleplon, zolpidem, zopiclone, diphenhydramine, dimenhydrinate, doxylamine, promethazine, chloral hydrate, dicyclomine, atropine, ipratropium bromide, oxitropium bromide, tiotropium, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, lisuride, human growth hormone, erythropoietin, haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, aripiprazole, bifeprunox, etanercept, derivatives of any of the foregoing, and combinations of any of the foregoing.

Hazardous agents are capable of causing mortality and/or serious effects including cancer, infections, organ toxicity, fertility problems, genetic damage, and birth defects. Hazardous agents can also possess mechanisms of action that are acutely less serious, but still potentially deleterious to the patient, such as suppression of the immune system. The suppression occurs by down regulation of a population or activity of specific cells that participate in the immune response, which increases susceptibility to infection. However, even though suppression of the immune system is potentially deleterious, it can also act to reduce inflammation in a subject, thereby providing a benefit to patients with autoimmune diseases.

"Heteroalkyloxy" means an —O-heteroalkyl group where heteroalkyl is as defined herein.

"Heteroalkyl" refers to alkyl, alkanyl, alkenyl and alkynyl radical, respectively, in which one or more of the carbon atoms (and any associated hydrogen atoms) are each independently replaced with the same or different heteroatomic groups. Typical heteroatomic groups include, but are not limited to, -O- , —S—, -O-O-, —S—S—, -O-S—, —NR'—, =N—N=, —N=N—NR'—, —PH—, —P(O)$_2$—, —O—P(O)$_2$—, —S(O)—, —S(O)$_2$—, —SnH$_2$—, and the like, where R' is hydrogen, alkyl, cycloalkyl, or aryl.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, P-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is between 5-20 membered heteroaryl, in some embodiments between 5-10 membered heteroaryl. In some embodiments heteroaryl groups can be those derived from thiophene, pyrrole, benzothiophene, benzofuran, indole, pyridine, quinoline, imidazole, oxazole and pyrazine.

"Heteroarylalkyl" refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In some embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20 membered heteroaryl, in some embodiments, 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Heteroaryloxy" means an —O-heteroaryl group where heteroaryl is as defined herein.

"N-oxide" (also known as "amine oxide" and "amine-N-oxide") refers to a chemical compound that contains the functional group R$_3$N$^+$—O$^-$, where R is hydrogen, alkyl, aryl, arylalkyl, cycloalkyl, cycloheteroalkyl, heteroalkyl, heteroaryl, or heteroarylalkyl.

"Oxide" refers to a chemical compound containing at least one oxygen atom as well as at least one other element.

"Patient" and "Subject" both independently include mammals, such as for example, humans.

"Pharmaceutically acceptable" refers to approved or approvable by a regulatory agency of a federal or a state government, listed in the U.S. Pharmacopeia, or listed in other generally recognized pharmacopeia for use in mammals, including humans.

"Pharmaceutically acceptable salt" refers to a salt of a compound, such as a salt of a hazardous agent, that is pharmaceutically acceptable and that possesses the desired pharmacological activity of the parent compound. Such salts include: (1) acid addition salts that are formed with inorganic acids such as hydrochloric acid, hydrobromic acid, sulfuric acid, nitric acid, phosphoric acid, and the like; or that are formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesul ionic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound either is replaced by a metal ion, e.g., an alkali metal ion, an alkaline earth metal ion, or an aluminum ion; or coordinates with an organic base such as ethanolamine, diethanolamine, triethanolamine, N-methylglucamine, and the like. In certain embodiments, a salt of a hazardous agent is the hydrochloride salt, and in certain embodiments, the sodium salt.

"Pharmaceutically acceptable vehicle" or "pharmaceutically acceptable excipient" refers to a pharmaceutically acceptable diluent, a pharmaceutically acceptable adjuvant, a pharmaceutically acceptable excipient, a pharmaceutically acceptable carrier, or a combination of any of the foregoing with which a compound, such as, for example, a hazardous agent, may be administered to a patient, which does not destroy the pharmacological activity thereof, and which is nontoxic when administered in doses sufficient to provide a therapeutically effective amount of the compound.

"Pharmacokinetics" refers to the assessment of the fate of an administered medication in the body. Parameters useful in characterizing pharmacokinetics include a blood concentration-versus-time curve include the area under the curve (AUC), the time to peak concentration ($T_{max}$), and the maximum compound concentration $C_{max}$, where $C_{max}$ is the maximum concentration of a compound in the blood plasma of a patient following administration of a dose of the compound to the patient, and $T_{max}$ is the time to the maximum concentration ($C_{max}$) of a compound in the blood or plasma of a patient following administration of a close of the compound to the patient.

"Powered injectors" are injection devices that have an energy source that powers a mechanism to fire the injector. Powered injectors of the present disclosure are configured to deliver, or inject, one or more hazardous agents into a subject in less than about 5 seconds.

"Solvate" refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intramolecular forces such as, for example, electrostatic forces, van der Waals forces, or hydrogen bonds. The teini "hydrate" refers to a solvate in which the one or more solvent molecules is water.

"Therapeutically effective amount" refers to the amount of a hazardous agent that, when administered to a subject for treating a disease or disorder, or at least one of the clinical symptoms of a disease or disorder, is sufficient to affect such treatment of the disease, disorder, or symptom. The therapeutically effective amount may vary depending, for example, on the compound, the disease, disorder, and/or symptoms of the disease, severity of the disease or disorder, and/or symptoms of the disease or disorder, the age, weight, and/or health of the patient to be treated, and the judgment of the prescribing physician. A therapeutically effective amount may be ascertained by those skilled in the art or capable of determination by routine experimentation.

"Treating" or "treatment" of any disease refers to arresting or ameliorating a disease or disorder, or at least one of the clinical symptoms of a disease or disorder, reducing the risk of acquiring a disease or disorder or at least one of the clinical symptoms of a disease or disorder, reducing the development of a disease or disorder, or at least one of the clinical symptoms of the disease or disorder, or reducing the risk of developing a disease or disorder, or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or at least one or more symptoms thereof in a patient which may be exposed to or predisposed to a disease or disorder even though that patient does not yet experience or display symptoms of the disease.

Reference is now made in detail to certain embodiments of the disclosure including, without limitation, hazardous agents, injectors and methods. The disclosed embodiments are riot intended to be limiting of the claims. To the contrary, the claims are intended to cover all alternatives, modifications, and equivalents.

Injection of Hazardous Agents

In various aspects, the present disclosure relates to the injection of hazardous agents. In some embodiments, the hazardous agents are cytotoxic agents. Examples of cytotoxic agents that may be used according to the present disclosure include, without limitation, 6-mercaptopurine, 6-thioinosinic acid, azathioprine, chlorambucil, cyclophosphamide, cytophosphane, cytarabine, melphalan, methotrexate, uramustine, anti-tissue necrosis factor biologicals, anti-cytokine biologicals, cell receptor antagonists, cell receptor analogues, and derivatives of each of the foregoing. Some of these agents are labeled "cytotoxic" because they act by directly killing cells or by impeding cell metabolism. Cytotoxic agents acting in this manner elicit their greatest effect against rapidly dividing cells. In the case of rapidly dividing tumor cells, cytotoxic agents are particularly effective because they act to kill these cells. This activity can also suppress the cells involved in a hyperactive immune response, resulting in a reduction in disease activity, which enables cytotoxic agents to treat diseases such as rheumatoid arthritis (and other autoimmune diseases), lupus, vasculitis and related conditions. The base mechanism of action is the suppression of a hyperactive immune response, which results in anti-inflammatory effects. For example, when used at low doses to treat such diseases, the method of action of the cytotoxic agent methotrexate is anti-inflammatory, not cytotoxic.

In some embodiments, one or more hazardous agents and/or pharmaceutically acceptable salts, solvates, hydrates, oxides and N-oxides thereof, can be injected in less than about 5 seconds via the use of a powered injector. In some embodiments, the present disclosure relates to the injection of one or more hazardous agents and one or more pharmaceutically acceptable excipients. In some embodiments, the present disclosure relates to the injection of a pharmaceutically acceptable salt of one or more hazardous agents.

Injection of Methotrexate and its Derivatives

In some embodiments, the injected hazardous agent is methotrexate and/or one or more derivatives of methotrexate as given by formula (I), described further below. In one aspect, the present disclosure relates to the injection of methotrexate and/or derivatives of methotrexate via a powered injector in less than about 5 seconds. In some embodiments, methotrexate and/or derivatives of methotrexate and/or pharmaceutically acceptable salts, solvates, hydrates, oxides and N-oxides thereof, are injected. In some embodiments, the present disclosure relates to the injection of methotrexate and/or derivatives of methotrexate and one or more pharmaceutically acceptable excipients. In some embodiments, the present disclosure relates to the injection of a pharmaceutically acceptable salt of methotrexate and/or derivatives of methotrexate. In some embodiments, the present disclosure relates to the injection of pharmaceutical compositions comprising methotrexate and a pharmaceutically acceptable excipient.

Jet Injection of Hazardous Agents

In some embodiments, the present disclosure relates to the injection of hazardous agents via a jet injector. In some embodiments, the jet injector is a needle-assisted jet injector. In some embodiments, the jet injector is a needle-free jet injector. In some embodiments, hazardous agents and/or pharmaceutically acceptable salts, solvates, hydrates, oxides and N-oxides thereof, are injected. In some embodiments, pharmaceutical compositions comprising one or more hazardous agents and one or more pharmaceutically acceptable excipients are injected. In some embodiments, a pharmaceutically acceptable salt of a hazardous agent is injected. In some embodiments, the present disclosure relates to the injection of pharmaceutical compositions comprising methotrexate and a pharmaceutically acceptable excipient.

Compounds

In various aspects, the present disclosure relates to hazardous agents. In various embodiments, the present disclosure relates to compounds of formula (I):

$$\text{(I)}$$

and pharmaceutically acceptable salts, solvates, hydrates, oxides and N-oxides thereof.

In various aspects, $R_1$, $R_2$, and $R_3$ are independently selected from the group hydrogen, alkyl, alkoxy, acyl, acylamino, alkylamino, alklysulfinyl, alkylsulfonyl, alkylthio, alkoxycarbonyl, aryl, arylalkyl, aryloxy, cycloalkyl, cycloheteroalkyl, dialkylamino, halo, heteroalkyl, heteroaryl, heteroarylalkyl, heteroalkyloxy, and heteroaryloxy.

In certain embodiments, the compound of formula (I) is the cytotoxic agent methotrexate, wherein $R_1$ is methyl and $R_2$ and $R_3$ are both hydrogen. Chemically, methotrexate is known as L-(+)-N-[p-[[(2,4-Diamino-6-pteridinyl)methyl]methylamino]-benzoyl]glutamic acid or by its systematic (IUPAC) name (2S)-2-[(4-{[(2,4-diamino-7,8-dihydropteridin-6-yl)methyl](methyl)amino}phenyl)formamido]pentanedioic acid.

In certain embodiments, compounds of formula (I) may be prepared using the methods described by U.S. Pat. No. 4,374,987 to Singh et al. and/or U.S. Pat. No. 4,080,325 to Ellard.

The hazardous agents of the present disclosure can comprise a therapeutically effective amount of one or more of the hazardous agents disclosed herein, in some embodiments in purified form, together with a suitable amount of a pharmaceutically acceptable vehicle, so as to provide the form for proper self administration by a patient. In some embodiments, when self administered by a patient, the hazardous agents of the present disclosure and pharmaceutically acceptable vehicles are sterile. In some embodiments, water can be used as a vehicle when the hazardous agents of the present disclosure are self injected. In some embodiments, saline solutions and aqueous dextrose and glycerol solutions can also be employed as liquid vehicles for injectable solutions. Suitable pharmaceutical vehicles can also include excipients such as sodium phosphate, sodium citrate, sodium acetate trihydrate, citric acid, glacial acetic acid, mannitol, polysorbate 80, L-arginine hydrochloride, metacresol, phenol, zinc oxide, and water. In some embodiments, hazardous agents of the present disclosure can also contain minor amounts of wetting or emulsifying agents, pH buffering agents, and/or auxiliary, stabilizing, thickening, lubricating and/or coloring agents.

In some embodiments, pharmaceutical compositions provided by the present disclosure comprise the hazardous agents disclosed herein together with one or more pharmaceutically acceptable excipients.

The amount of the one or more pharmaceutically acceptable excipients in a pharmaceutical composition can be, for example: from about 0.005% w/v to about 10% w/v; and from about 2% w/v to about 6% w/v; where % w/v is based on the total weight of the excipient per unit volume.

In some embodiments, pharmaceutical compositions provided by the present disclosure comprise a pharmaceutically acceptable salt of the hazardous agents disclosed herein.

Pharmacokinetics

Typically, the bioavailability of a hazardous agent is close to 100% when it is injected or administered intravenously because the hazardous agent does not get destroyed in the gastrointestinal tract and cleared from the subject's body or, if the hazardous agent is injected into a tissue, it does not have any tissue architecture or constituents to traverse prior to being systemically available. By changing the way the hazardous agent is administered, the pharmacokinetics of that hazardous agent may also be altered in order to maintain the pharmacokinetics and/or bioavailability of the hazardous agent in a particular manner suitable for a patient, dose or other hazardous agent property.

In some embodiments, the bioavailability of a hazardous agent can be maintained, or approximated to a known or desired level, by selecting one or more factors in the configuration of a powered injector, and in some embodiments one or more factors in the configuration of a jet injector, to maintain bioequivalence for the hazardous agent. Bioequivalence can be measured using means known in the art to measure plasma levels to determine the rate and extent of absorption of the hazardous agent and determining the AUC for the hazardous agent to determine the extent of absorption. $C_{max}$ concentrations may also be used to determine the rate of hazardous agent absorption. Bioequivalence is established if a hazardous agent injected via an injector of the present disclosure reaches the site of absorption in similar times and is absorbed to the same extent as if the hazardous agent had been introduced to the subject via other known routes of administration. Typically, bioequivalence of a hazardous agent is reached if one or more confidence intervals of the measured pharmacokinetic parameters fall between about 80% and about 125% of a known or desired level of the hazardous agent (see: Approved Compound Products With Therapeutic Equivalence Evaluations, *US Food and Compound Administration Electronic Orange Book*, 27th ed. Washington, D.C.: US Department of Health & Human Services (2007); and 21 C.F.R. §320.33 (Apr. 1, 2005)).

The rate of injection, or the speed at which a hazardous agent is delivered to a subject, is a function of several features of the injector used, and can include, without limitation, the pressure utilized by the injector to make the injection, and/or the configuration and dimensions of the injection outlet of an injection outlet member in an injector, such as the needle used or the needle-free nozzle. In some embodiments, the speed of injection of an injector can be selected to maintain the pharmacokinetics and/or bioavailability of a hazardous agent at a level that is similar to other methods of parenteral delivery including, without limitation, traditional hypodermic-syringe injection, by altering the pressure used in the injector to jet inject the hazardous agent.

Changes in one or more factors in the configuration of an injector may be necessary because the interactions of the hazardous agent, once ejected from an injector of the present disclosure, can vary widely from subject to subject. It is believed that the deposition pattern of the hazardous agent resulting from injection is noteworthy as increased dispersion from a powered injector, as compared to bolus deposition from a manual syringe, may impact the hazardous agent's interaction with cells and either enhance or impede the migration of the hazardous agent to the systemic circulation. For example, for the hazardous agent methotrexate, cell transport mechanisms exist that result in methotrexate uptake by cells, including the reduced folate carrier and membrane transport proteins termed folate receptors. These mechanisms have variable rates of action and variable degrees of expression (see Kremer, J. M., Toward a better understanding of methotrexate, *Arthritis and Rheumatism* 2004; 50: 1370-1382). Since it is likely that methotrexate would encounter such cells after injection but before reaching the systemic circulation, the pharmacokinetics and/or bioavailability of methotrexate resulting from the injection can vary greatly from individual to individual, thereby necessitating a change in the manner in which methotrexate is administered from subject to subject. The amount of change to one or more factors in the configuration of an injector will therefore depend, at least in part, on the nature of the disease, the subject to be treated and the discretion of the prescribing physician, and may be determined by standard techniques known in the art.

By using a powered injector of the present disclosure, a hazardous agent may be injected into a subject more precisely and completely than if it were injected via a manual syringe, and in less than about 5 seconds. In a jet injector embodiment, the configuration of the jet injector, and the factors affecting the injection, can be selected to obtain a $C_{max}$ for a hazardous agent that is the same or substantially the same as that seen with other methods of parenteral delivery including, without limitation, a typical hand-powered hypodermic syringe. In another jet injector embodiment, the configuration of the injector, and the factors affecting the injection, can be selected to obtain a $T_{max}$ for a hazardous agent that is the same or substantially the same as that seen with other methods of parenteral delivery including, without limitation, a typical hand-powered hypodermic syringe. In a further jet injector embodiment, the configuration of the jet injector, and the factors affecting the injection, can be selected to obtain both a $C_{max}$ and a $T_{max}$ for a hazardous agent that is the same or substantially the same as that seen with other methods of parenteral delivery including, without limitation, a typical hand-powered hypodermic syringe.

The pharmacokinetics of the cytotoxic agent methotrexate will now be described as a specific example of the pharmacokinetics of the disclosed hazardous agents.

The pharmacokinetics of injected methotrexate are generally known (see, e.g., Aquerreta, I., et al., *Ped. Blood & Cancer* (2003); 42(1), 52-58; and Seideman, P., et al., *Br. J. Clin. Pharmacol.* (1993) April; 35(4): 409-412). Methotrexate is a weak dicarboxylic acid with an acid dissociation constant of about 4.8 to about 5.5, and thus exists mostly in its ionized state at physiologic pH. After intravenous administration, the initial average distribution volume of methotrexate is typically about 0.18 L/kg (or about 18% of the subject's body weight) and the average steady-state distribution volume typically ranges from about 0.4 L/kg to about 0.8 L/kg (or about 40% to about 80% of the subject's body weight). Methotrexate is generally completely absorbed from parenteral routes of injection. After intramuscular injection of methotrexate, peak serum concentrations ($C_{max}$) occur in about 30 to about 60 minutes ($T_{max}$) in most patients. However, individual plasma concentrations of injected methotrexate have been reported to vary widely between individual subjects. For example, in pediatric patients with juvenile rheumatoid arthritis, the average mean serum concentrations of methotrexate were about 0.59 µM (averaged over a range of about 0.03 µM to about 1.40 µM) at about 1 hour, an average of about 0.44 µM (averaged over a range of about 0.01 µM to about 1.00 µM) at about 2 hours, and an average of about 0.29 µM (averaged over a range of about 0.06 µM to about 0.58 µM) at about 3 hours. In pediatric patients receiving methotrexate injections for acute lymphocyctic leukemia (at doses of about 6.3 mg/m$^2$ to about 30 mg/m$^2$) or for juvenile rheumatoid arthritis (at doses of about 3.75 mg/m$^2$ to about 26.2 mg/m$^2$), the terminal half-life of methotrexate has been reported to range from about 0.7 hours to about 5.8 hours, or from about 0.9 hours to about 2.3 hours, respectively.

Toxicity at Higher Doses

As shown by several prior studies, it is presently unclear whether increasing a regular dose of methotrexate results in an increase in compound efficacy. What is clear, however, is that as the dose of methotrexate increases, toxicity-associated side effects also increase. For example, Furst et al. evaluated the effect of increasing oral doses of methotrexate from 5 mg/m$^2$ (7.5 mg to 10 mg) per week to 10 mg/m$^2$ (15 mg to 22 mg) per week in 46 patients (see Furst, D. E., et al., *J. Rheumatol.*, 1989; 16: 313-320). In this study, the authors noted that higher doses of methotrexate resulted in a dose-related efficacy response together with a trend toward increased toxicity. However, a separate study conducted by Lambert et al. did not find improved efficacy with increasing doses of methotrexate (see Lambert, C. M., et al., *Arthritis and Rheumatism*, 2004; 50: 364-371). In this study, the effect of escalating intramuscular methotrexate dosage from 15 mg per week to 45 mg per week in 64 patients was evaluated. The authors observed an improvement in disease activity scores (DAS) in some patients following a switch from oral to intramuscular administration at 15 mg per week (average DAS28 reduced from 5.6 to 5.2). Fifty-four patients who did not achieve a favorable DAS28 score (DAS28<3.2) also demonstrated no difference in disease improvement when compared to patients who were given placebo.

Visser and van der Heijde conducted a review of several studies focused on the efficacy of varying dosages and modes of administration of methotrexate in subjects with rheumatoid arthritis (see Visser, K., and van der Heijde, D., *Annal. Rheum. Diseases,* 2008; published online 25 Nov. 2008 as doi: 10.1136/ard.2008.092668). The authors concluded that starting subjects on methotrexate at 15 mg/week orally, then escalating the dose 5 mg/month until a peak concentration of 25-30 mg/week (or the highest tolerable dose per subject) is reached, followed by a subsequent switch to subcutaneous administration in the event of an insufficient response, seems to be the optimal means of dosing and routing for methotrexate in rheumatoid arthritis.

Varied Bioavailability with Oral Dosing

Several studies have also demonstrated that, when taken orally, the bioavailability of methotrexate is highly variable. There is evidence to suggest that oral bioavailability of methotrexate declines as the dose is increased. For example, Herman et al. characterized the bioavailability of intravenously and orally administered methotrexate at a dose of 10 mg/m$^2$ per week in 41 patients with rheumatoid arthritis (see Herman, R. A., et al., *J. Pharm. Sci.*, 1989; 78: 165-171). The authors found that absorption of methotrexate administered orally was only about 70%±27% of the total absorption observed following intravenous administration of the same amount. Additionally, Hamilton et al. compared the bioavailability of intramuscularly administered methotrexate versus oral administration at a starting dosage of 7.5 mg per week, with an average maintenance dosage of 17 mg per week, in 21 patients with rheumatoid arthritis (see Hamilton, R. A., and Kremer, J. M., *Br. J. Rheum.*, 1997; 36: 86-90). The authors found that the total absorption of methotrexate following oral administration fell about 13.5% during maintenance dosage relative to the total absorption seen at the starting dosage.

Kurnik et al. compared the bioavailability of an oral dose of methotrexate, ranging from 15 mg to 25 mg, to the same dose administered subcutaneously in patients with Crohn's disease (see Kurnik, D., et al., *Alimentary Pharm. Ther.,* 2003; 18: 57-63). The authors observed that oral bioavailability varied widely among the patients given oral doses, with an average bioavailability being approximately 73% of the total bioavailability of methotrexate seen in patients given methotrexate subcutaneously.

Hoekstra et al. evaluated the bioavailability of 25 mg and higher doses of methotrexate, given orally and subcutaneously, in patients with rheumatoid arthritis (see Hoekstra, M. et al., *J. Rheum.,* 2004; 31: 645-8). They reported that oral bioavailability was, on average, only 64% of that seen for methotrexate administered subcutaneously at a median dosage of 30 mg per week. The relative absorption varied from 21% to 96% in the tested patients.

Brooks et al. compared the pharmacokinetics and bioavailability of methotrexate administered intramuscularly versus administered subcutaneously at doses ranging from 12.5 mg to 25 mg per week (Brooks, P. J. et al., *Arthritis and Rheumatism,* 1990; 33: 91-94). The authors found similar peak serum concentrations and bioavailability for both routes, however $T_{max}$ was observed to be faster after subcutaneous administration in 4 out of 5 patients tested.

Oguey et al. evaluated the effect of food on the bioavailability of oral methotrexate at a dose of 15 mg in 10 rheumatoid arthritis patients (see Oguey, D., et al., *Arthritis and Rheumatism,* 1992; 35:611-614). They reported that oral bioavailability was unaffected by flood, at 67% and 63%, respectively, following fasting and fed conditions, however they also noted that the inter-patient variability was high, ranging from 28% to 94%.

Hoekstra et al. evaluated the effect of splitting oral doses of 25 mg to 35 mg methotrexate into 2 equal portions given 8 hours apart in 10 patients with rheumatoid arthritis (see Hoekstra, M., et al., *J. Rheum.,* 2006; 33: 481-485). They showed that bioavailability of a split dose increased to 90% of that achieved by parenteral administration, as compared to 76% bioavailability when the same amount was given as a single oral dose.

Oral Versus Subcutaneous Administration

Recently, Braun et al. reported the results of a 6-month, double-blind, controlled trial comparing the clinical efficacy and safety of orally administered methotrexate versus subcutaneously administered methotrexate in 375 patients with active rheumatoid arthritis, at a starting dose of 15 mg per week (see Braun, J. et al., *Arthritis and Rheumatism,* 2008; 58: 73-81). After 16 weeks, significantly more patients who started on subcutaneous methotrexate successfully achieved the American College of Rheumatology criteria for 20% improvement (ACR20) than those who started on oral methotrexate. Specifically, 85% of patients started on subcutaneous methotrexate achieved an ACR20 result versus 77% of those patients started on oral methotrexate.

A trend for greater ACR20 and greater American College of Rheumatology criteria for 70% improvement (ACR70) scores was also observed after 24 weeks. At 24 weeks, the percentage of patients with an ACR20 response was significantly higher in a subcutaneously-administered methotrexate group (78%) than in an orally-administered methotrexate group (70%). The percentage of patients achieving an ACR70 response at week 24 was also higher in patients receiving subcutaneous methotrexate than in those receiving oral methotrexate (41% versus 33%).

At 24 weeks, the number of swollen joints was lower in the group that received subcutaneous methotrexate than in the group that received oral methotrexate (2 versus 3), as was the number of tender joints (3.5 versus 6). The median Health Assessment Questionnaire (HAQ) score, a comprehensive measure of outcome in patients with a wide variety of rheumatic diseases, was lower in the group administered methotrexate subcutaneously as compared with the orally administered group at week 24 (0.4 versus 0.5). The median Disease Activity Score (DA S28), an index that measures the disease activity in patients with rheumatoid arthritis, was also lower in the group administered with methotrexate subcutaneously than in the orally administered group (3.3 versus 3.7) after 24 weeks.

At 16 weeks, only 52 patients (14% of the total tested) were classified as ACR20 non-responders. However, when these patients were switched from a 15 mg oral dose of methotrexate to a 15 mg dose administered subcutaneously, 30% of them demonstrated a positive ACR20 response, and 23% more of them demonstrated a positive ACR20 response when the dosage of subcutaneously-administered methotrexate was increased from 15 mg to 20 mg.

In a subgroup of patients with a time between diagnosis and study entry of ≥1 year who had received prior disease-modifying antirheumatic compounds or steroids (n=98), the difference in the percentage of ACR20 responders between the orally administered (63%) and subcutaneously-administered (89%) methotrexate groups was even greater than in the entire study population. Further, in this group of patients, the time to achieve an ACR20 response was approximately 2 weeks shorter with subcutaneous administration (4 weeks) of methotrexate than with oral administration (6 weeks).

The authors concluded that superior clinical efficacy was demonstrated when methotrexate was administered to subjects subcutaneously as compared to the same dose of methotrexate given orally. Additionally, subcutaneous administration was not accompanied by a significantly higher rate of adverse events.

Oral Versus Intramuscular Administration

Wegrzyn et al. compared the efficacy and tolerability of methotrexate administered orally versus intramuscularly in a survey of 143 patients with rheumatoid arthritis (see Wegrzyn, J. et al., *Annal. Rheum. Diseas.,* 2004; 63: 1232-1234). Patients in this study were initially given methotrexate intramuscularly, but were subsequently switched to oral administration following a supply shortage, approximately 3 months into the study. Subsequently, 47 patients were switched back to intramuscular administration of methotrexate and observed for 3 months.

After switching to orally administered methotrexate, 49% to 71% of patients reported worsening of symptoms (morning pain and joint pain) and 48% reported experiencing nausea. In the group who were switched back to intramuscularly administered methotrexate, 40% to 70% of patients reported improvement in symptoms (morning pain and joint pain). Somewhat fewer patients (40%) reported nausea. Liver transaminases increased in nearly 25% of patients after switching to oral methotrexate with subsequent decreases after switching back to intramuscular methotrexate.

Hoffmeister reported on 15 years of early experience with methotrexate in 78 rheumatoid arthritis patients. Patients in this study were given 10 mg to 15 mg of intramuscular methotrexate once a week (see Hoffmeister, R. T., *Amer. J. Med.,* 1983; 75(6A):69-73). Eighty-two percent were judged to have moderate or marked improvement following treatment. Patients who achieved the expected maximal effect were permitted to switch to oral methotrexate. Of the 48 patients who switched to oral methotrexate, 10 deteriorated following the switch and subsequently improved after switching back to intramuscular administration.

Taken in aggregate, the foregoing pharmacokinetic studies collectively suggest that parenteral methotrexate is better absorbed, more efficacious and better tolerated versus the same dose given orally.

In some embodiments, one or more of the hazardous agents disclosed herein can be injected into a tissue of a subject in less than about 5 seconds by a powered injector according to the present disclosure to a depth of from about 2 mm to about 10 mm, in some embodiments from about 3 mm to about 5 mm, and in some embodiments about 3.5 mm. In some embodiments, the hazardous agents disclosed herein can be injected into a tissue of a subject by a powered injector at a pressure range of about 200 p.s.i. to about 500 p.s.i., in some embodiments at a range of about 300 p.s.i., in some embodiments at about 400 p.s.i., and in some embodiments at about 500 p.s.i. In some embodiments, the powered injector is needle-assisted; in some embodiments the powered injector is needle-free; in some embodiments the powered injector is a needle-assisted jet injector; and in some embodiments the powered injector is a needle-free jet injector.

In some embodiments, a jet injector is configured to render the pharmacokinetics of a hazardous agent, for example methotrexate, unaffected or substantially unaffected compared to other methods of parenteral delivery including, without limitation, traditional, hand-powered, hypodermic-syringe injection. In some embodiments, a jet injector is configured, such as by selecting the factors that can affect the pharmacokinetics, to maintain the speed at which the hazardous agent is absorbed into the subject's bloodstream, and to cause the hazardous agent to be absorbed into the subject's bloodstream at the same rate or substantially the same rate as with traditional, hand-powered hypodermic syringe injection, for maintaining the pharmacokinetics and/or bioavailability for the hazardous agent.

In some embodiments, the depth of injection of a hazardous agent can be altered in order to deliver that hazardous agent to a subject in such a way so as to approximate the known and/or desired pharmacokinetics of that hazardous agent. In some embodiments, the depth of injection is increased in order to maintain the known and/or desired pharmacokinetics of a hazardous agent. In some embodiments, the depth of injection is decreased in order to maintain the known and/or desired pharmacokinetics of a hazardous agent. In some embodiments, the pressure utilized by a jet injector can be altered in order to deliver a hazardous agent from the jet injector into a subject in such a way so as to approximate the known and/or desired pharmacokinetics of that hazardous agent. In some embodiments, the pressure is increased in order to maintain the known and/or desired pharmacokinetics of a hazardous agent. In some embodiments, the pressure is decreased in order to maintain the known and/or desired pharmacokinetics of a hazardous agent. The injection characteristics that will serve to maintain the known and/or desired pharmacokinetics for a hazardous agent will depend, at least in part, on the nature of the disease to be treated, the individual subject, and the hazardous agent to be injected, and may be determined by standard techniques known in the art.

In some embodiments, the depth of injection is altered in order to deliver a dose of methotrexate from a jet injector to a subject such that the pharmacokinetics of methotrexate are the same, or substantially the same, as the pharmacokinetics of methotrexate administered via other methods of parenteral delivery including, for example, traditional, hand-powered, hypodermic-syringes. In some embodiments, the pressure of injection is altered in order to deliver a dose of methotrexate from a jet injector to a subject such that the pharmacokinetics of methotrexate are the same, or substantially the same, as the pharmacokinetics of methotrexate administered via other methods of parenteral delivery including, without limitation, traditional, hand-powered, hypodermic-syringes. In some embodiments, the depth of injection and the pressure of injection are altered in order to deliver a dose of methotrexate from a jet injector to a subject such that the pharmacokinetics of methotrexate are the same, or substantially the same, as the pharmacokinetics of methotrexate administered via other methods of parenteral delivery including, without limitation, traditional, hand-powered, hypodermic-syringes.

Therapeutic Uses

Hazardous agents of the present disclosure can be administered to a patient, which in some embodiments is a human, suffering from any disease or disorder for which the disclosed hazardous agents are known, believed to be, or hereafter determined to be therapeutically effective including, without limitation, cancer, rheumatoid arthritis, juvenile rheumatoid arthritis, psoriatic arthritis, systemic lupus erythematosus, steroid-resistant polymyositis or dermatomyositis, Wegener's granulomatosis, polyarteritis nodosa, and vasculitis. In certain embodiments, hazardous agents of the present disclosure may be used to treat rheumatoid arthritis.

The suitability of hazardous agents provided by the present disclosure in treating the above-listed diseases may be determined by methods described in the art.

Dosing

The amount of a hazardous agent that will be effective in the treatment of a particular disease disclosed herein will depend, at least in part, on the nature of the disease, and may be determined by standard techniques known in the art. In addition, in vitro or in vivo assays may be employed to help identify optimal dosing ranges. Dosing regimens and dosing intervals may also be determined by methods known to those skilled in the art. The amount of a hazardous agent administered may depend on, among other factors, the subject being treated, the weight of the subject, the severity of the disease, the route of administration, and the judgment of the prescribing physician.

For systemic administration, a therapeutically effective dose of a hazardous agent may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of a hazardous agent, such as that typically available in a pre-filled, single shot, preset-dosage injector, for example, can be selected to provide an equivalent molar quantity or mass equivalent dose of a specific hazardous agent. A dose can comprise multiple dosage forms. For example, therapeutically effective doses of methotrexate in patients can range from about 7.5 mg to about 150 mg per milliliter of injection. In certain embodiments, a therapeutically effective dose can comprise a concentration of methotrexate ranging from about 15 mg to about 75 mg per milliliter, in certain embodiments, from about 15 mg to about 50 mg per milliliter, and in certain embodiments, from about 15 mg to about 25 mg per milliliter. In some embodiments, a therapeutically effective dose of methotrexate is selected from about 5 mg/ml, about 10 mg/ml, about 15 mg/ml, about 20 mg/ml, about 25 mg/ml, about 30 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 60 mg/ml, about 61 mg/ml, about 62 mg/ml, about 63 mg/ml, about 64 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, and about 150 mg/ml. The dose of a hazardous agent and appropriate dosing intervals can be selected to maintain a sustained therapeutically effective concentration of a hazardous agent in the blood of a patient, and in certain embodiments, without exceeding a minimum adverse concentration.

In some embodiments, hazardous agents, inclusive of compounds of formula (I), can be administered via an injector in the management of severe, active rheumatoid arthritis in selected adults and active polyarticular-course juvenile rheumatoid arthritis in children who have insufficient response or cannot tolerate first line therapy, such as nonsteroidal anti-inflammatory compounds (NSAIDs). In some embodiments, dosage of hazardous agents in adult rheumatoid arthritis can be 7.5 mg given as a single dose or three divided doses of 2.5 mg at 12-hour intervals. In adult rheumatoid arthritis, dosage can be adjusted gradually to achieve optimal response. Hazardous agents, however, can be used at doses up to 25 mg per by the injectable routes disclosed herein.

In certain embodiments, hazardous agents provided by the present disclosure may be administered via injectors of the present disclosure once per day, twice per day, and in certain embodiments at intervals of more than once per day. Dosing may be provided alone or in combination with other hazardous agents and may continue as long as required for effective treatment of the disease. Dosing includes administering one or more of the hazardous agents disclosed herein to a subject, in a fed or fasted state.

A dose may be administered in a single injection or in multiple injections. When multiple injections are used the amount of a hazardous agent(s) contained within each of the multiple injections may be the same or different.

In certain embodiments, an administered dose is less than a toxic dose. Toxicity of the hazardous agents described herein is well known in the art and can also be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a hazardous agent may exhibit a high therapeutic index. The data obtained from the art and from these cell culture assays and animal studies may be used in formulating a dosage range that is not toxic for use in humans. A dose of a hazardous agent may be within a range of circulating concentrations in, for example, the blood, plasma, or central nervous system, that is therapeutically effective and that exhibits little or no toxicity.

During treatment a dose and dosing schedule may provide sufficient or steady state systemic concentration of one or more hazardous agents to treat a disease. In certain embodiments, an escalating dose may be administered.

It is believed that the hazardous agents of the present disclosure, when administered via a powered injector of the present disclosure, will enhance patient compliance by allowing for non-clinical administration of the hazardous agents via self-administration, as compared to requiring the patient to obtain injections from a medical professional, and as compared to oral dosage forms which may require administration up to several times per week, a regimen that is inconvenient for patients and difficult for patients to remember. Compliance may be further enhanced by the speed at which the powered injectors of the present disclosure deliver the hazardous agent(s) into an injection site which, is less than about 5 seconds. Additionally, it is believed that powered injectors of the present disclosure are capable of delivering a hazardous agent more precisely, in a controlled manner of delivery, thereby reducing the exposure of the hazardous agents outside of the injection site and, in some embodiments, eliminating that exposure completely. In some embodiments, the injector is pre-filled with one or more hazardous agents so that the user is not required to draw up the hazardous agent, as they would otherwise be required to do when using a hand-driven, or traditional, syringe. This facilitates operation and accurate dosing in the administration of hazardous agents, especially for those patients who have a disease or disorder that makes it difficult for them to draw up medicine and self-inject. It is therefore believed that administration of the hazardous agents of the present disclosure via powered injectors of the present disclosure will provide a safer means of delivery and will significantly reduce the risk of exposure to the hazardous agents to non-users of the powered injectors and reduce the risk of unnecessary toxicity to the patient utilizing the powered injectors.

Administration of hazardous agents as disclosed herein presents a new option for patients who could benefit from converting from oral dosage forms of a hazardous agent to injection dosage forms of such hazardous agents, but for whom their physicians believe that the current product options are not practical for self-injection. The foregoing includes, without limitation, compounds of formula (I). It is also believed that administration of hazardous agents via powered injectors of the present disclosure will increase simplicity and ease-of-use for patients who may have some degree of physical impairment as may be the case in, for example, rheumatoid arthritis. Additionally, it is believed that administration of hazardous agents via injectors of the present disclosure will decrease the overall health care costs for subjects by reducing the total number of visits to a health care provider to receive injections.

In some embodiments, hazardous agents can be self administered by a subject in less than about 5 seconds via a needle-assisted powered injector of the present disclosure. It is believed that the use of a powered injector will make self-administration by subjects easier, increase the consistency of delivery of the hazardous agents by the subject, reduce the risk of toxicity associated with the hazardous agents, and will therefore enable greater use of hazardous agents to treat maladies such as, for example, rheumatoid arthritis. Further, it is expected that such an injector will extend the clinical utility of hazardous agents for patients by increasing the consistency of delivering a complete dose to the patient, reducing the risk of loss of the hazardous agents outside of the injection site, and reducing the toxicity risk associated with injecting hazardous agents, thereby increasing overall patient compliance and prolonging the therapeutic dosing potential of hazardous agents prior to switching to biologics, which is the normal clinical practice.

Injectors

Typical hypodermic syringes utilize the force of one or more of a user's fingers pushing to deliver an injection. In some embodiments, powered injectors of the present disclosure are configured to help a subject repeatably and accurately administer one or more hazardous agents to a preset depth at each injection in less than about 5 seconds without the need to utilize such pushing force.

Known autoinjector embodiments of powered injectors use an energy source that produces moderate to low pressure in the medicament chamber so that a medicament contained in the medicament chamber is fired at a slow speed, similar to the pressure and speed from a finger-driven syringe. In contrast, autoinjector embodiments of the powered injectors of the present disclosure use an energy source that produces moderate to high pressure in the medicament chamber so that a medicament contained in the medicament chamber is fired at a fast speed and is completely injected into a subject in less than about 5 seconds. Other embodiments of the powered injectors are jet injectors, which can be needle-assisted or needle-free jet injectors. Jet injector embodiments can be configured to have an energy source selected to produce a high pressure in the medicament chamber to eject the medicament with sufficient pressure, force, and speed to exit the injector as a fluid jet. As described in greater detail below, whereas a medicament injected into a subject via an autoinjector or hypodermic syringe is delivered in a bolus near the needle tip, the medicament delivered from a jet injector is sprayed rapidly into the tissue, typically remotely from the needle tip, and typically does not deposit the medicament in a bolus local to a needle tip. Needle-free jet injectors use sufficient pressure and injection speed so that the fluid jet breaks through the outer layer of the skin, depositing the medicament thereunder. Needle-assisted jet injectors can use lower pressures than needle free-jet injectors because they employ a needle to break through the outer part of the skin, but have pressures and speeds that are sufficiently high so that the medicament exits the needle tip as a fluid jet.

Some embodiments of the injectors disclosed herein are single-shot injectors, configured to deliver in a single shot the entire volume of the agent(s) contained within a chamber of the injector or within a cartridge contained within the injector. In other embodiments, the injectors are configured to inject only a portion of the contents of the injector or a cartridge within the injector and can use dosage-setting mechanisms to enable the selection of the volume of injection to be delivered in one shot, or other mechanisms to provide an adjustable dosage. In each of the foregoing embodiments, the injector can be pre-filled, or configured to receive a cartridge that has the dosage of medicament. Alternative embodiments are configured to be finable as known in the art.

Injectors provided by the present disclosure may be utilized by patients to self-inject one or more hazardous agents. Various aspects of the present disclosure relate to self-injection of one or more hazardous agents by a subject without the aid of a health care provider. In certain embodiments, the injectors use a needle to inject hazardous agents into a target tissue of a subject, such as autoinjector or needle-assisted jet injector embodiments, while other embodiments are needle-free injectors and thus do not require a needle to inject hazardous agents into a target tissue of a subject. In certain embodiments, the injectors may utilize pressure sufficient to deliver one or more hazardous agents completely and quickly. In certain embodiments, the injectors may utilize sufficiently high pressure to deliver one or more hazardous agents completely and quickly in a fluid jet.

In some embodiments, powered injectors provided by the present disclosure do not require any priming or preparatory step in order to place them in condition to deliver an injection, thereby reducing or eliminating exposure of the hazardous agent to the air and/or premature expulsion of the hazardous agent from a needle of the injector prior to the delivery shot. Therefore, the risk of contact with the a hazardous agent contained in the injector, by the subject or by a non-user of the injectors, is reduced or eliminated.

Referring to FIGS. 1-5, an embodiment of an injector according to the present disclosure is presented. The embodiment shown in these figures is a needle injector, and depending on the spring used and delivery conduit, including the needle and injection outlet, can be configured as an autoinjector or a needle-assisted jet injector. The depicted injector 12 has an outer housing member 14 configured for allowing a user to handle the injector 12 and that substantially houses most of the components shown in FIG. 2. In some embodiments, outer housing 14 is formed from two mating portions 14a, 14b that can be configured to attach to one another by a snap or press fit or by using adhesives, welding or the like. Housing 14 includes a fluid chamber 22 therein that is configured for storing and dispensing one or more liquid medicaments, such as, for example, one or more hazardous agents. In the embodiment shown in FIG. 2, fluid chamber 22 is formed in a prefilled syringe 18 that fits within housing 14, but other types of fluid chambers can be used, including known types of cartridges that can be prefilled, refillable, or the like with the medicament(s). Additionally, fluid chamber 22 can be integrally formed within housing 14.

In the embodiment shown, a safety member 80 is located on the proximal end of outer housing 14 and is removably affixed thereto by a plurality of tabs that extend through matching openings formed in outer housing 14 to form a press-fit between safety member 80 and outer housing 14. Safety member 80 is configured to prevent or reduce the likelihood of unintended firing of the injection device during, for example, shipping or handling of injector 12. Safety member 80 can be removed by a user of injector 12 to allow for unrestricted use of injector 12. Alternative embodiments of the injectors can be constructed without safety member 80.

In a further embodiment, a sleeve 16 is housed within and mounted to the housing 14 and acts as a syringe support member. In some embodiments, the sleeve 16 is configured to hold and position a prefilled syringe 18, carpule or other container of the type known in the art, such as, for example, a BD Hypak™ prefilled syringe (Becton, Dickinson and Company). One example of a suitable prefilled syringe for use in the depicted embodiments is one which is available in various sizes and volumes and is sold prefilled with medicament, such as the Becton Dickinson Hypak™. In some embodiments, the glass of the syringe body can be adhered to the needle. Using a prefilled syringe facilitates handling of the medicament when the injector is assembled, and there is an extensive body of knowledge of how the medicaments keep and behave in a prefilled syringe. In some embodiments, sleeve 16 is substantially fixed to the housing 12, such as by snaps, an adhesive, a weld, or another known attachment. The pre tilled syringe 18 can have a container portion 20 that defines in its interior a fluid chamber 22, which is prefilled with an injectable medicament such as, for example, one or more hazardous agents. In other embodiments, the medicament container and chamber are provided by other structures, such as a chamber that can be integral with or held in the housing, needle hub 32, or other injection outlet portion of the injector, for example. At the distal end of the prefilled syringe 18 is an injection-assisting needle 24. Needle 24 has an injecting tip 26 configured as known in the art to penetrate the tissue of a patient which, in some embodiments, is the skin. A needle bore extends through the needle 24, as known in the art. The bore is in fluid communication with the medicament in the fluid chamber 22 and is open at the needle tip 26 to inject the medicament.

At a proximal end of the fluid chamber 22, opposite from the needle 24, is a plunger 28 that seals the medicament in the fluid chamber 22. In some embodiments, a syringe wall comprises a tubular portion which, in some embodiments, is closed at a distal end and open at a proximal end, to define the fluid chamber 22. Plunger 28 is slideably received in the tubular portion. The prefilled syringe 18 is configured such that when the plunger 28 is displaced in a distal direction, the volume of the fluid chamber 22 is decreased, forcing the medicament out of the chamber 22 and through the bore of needle 24. At the distal end of the fluid chamber 22 is a needle hub portion 32 to which the needle is mounted. A syringe flange 35 extends radially from the proximal end of the syringe wall. In injector embodiments that use cartridges, carpules or other containers that define a chamber to contain the medicament, the needle can be fluidly connected with the chamber in a different manner, such as by connecting directly to the cartridge, carpule, or other container, or by connecting to another portion of the injector, such as a housing thereof, by a separate needle hub.

Figures 2, 3:
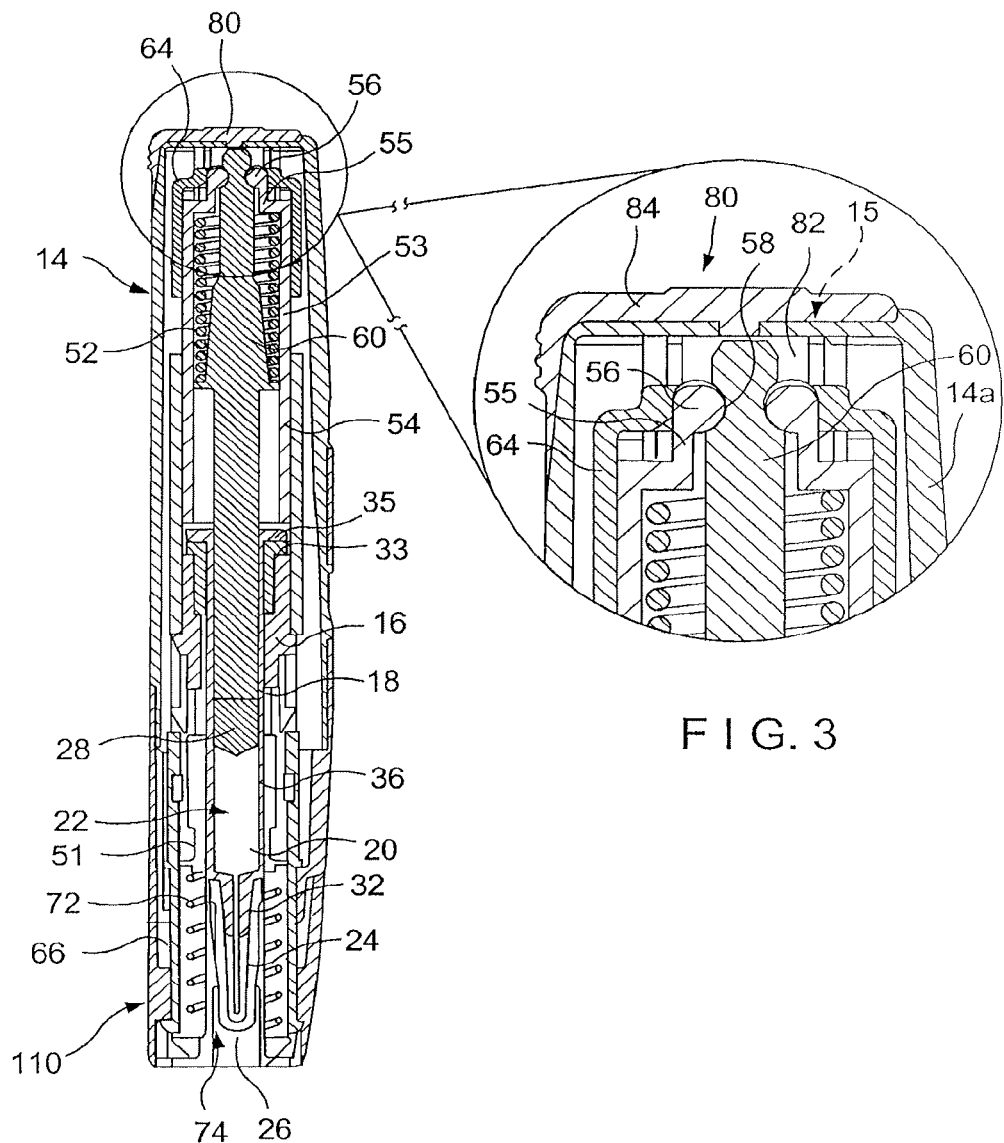
FIG. 2 is a cross-sectional view of the injection device of FIG. 1 in a safety state taken along line A-A.
FIG. 3 is an enlarged view of a portion of the cross-section shown in FIG. 2.

In the embodiment depicted in FIG. 2, the prefilled syringe 18 has a syringe body 36 wherein the flange 35, syringe wall, and hub portion 32 is of unitary construction. In some embodiments, the material comprising the syringe body 36 is glass, but other materials such as, for example, plastic or metal, can be used in other embodiments.

To radially position the distal end of the prefilled syringe 18, in some embodiments sleeve 16 has a narrowed bore portion 51 that can be configured to abut the outside of the syringe wall. This is especially beneficial when the needle is inserted into the patient's skin. The narrowed bore portion 51 can be made of a resilient material, such as an elastomer, or it can be made unitarily with the rest of sleeve 16, such as by a series of radially-aligned, resiliently-flexible fingers. Additionally, the proximal portion of the syringe 18 can be held in place by a shock-absorbing device 33, which, in some embodiments, locates the proximal side of the syringe body 36 radially, and absorbs shocks from the impact of a sudden firing of the ram 60, such as in jet-injector embodiments, which produce elevated pressures in the fluid chamber 22 or container 20.

A trigger mechanism can also be housed within housing 14. In some embodiments, the trigger mechanism includes an inner housing 54 that can be attached to the outer housing 14, such as by snaps, an adhesive, a weld, or other known attachment. Trigger protrusions 56 extend inwardly from the proximal end of the inner housing 54 and are resiliently biased outwardly. Trigger protrusions 56 are received in a recess 58 of ram 60 in blocking association therewith to prevent distal movement of the ram 60 prior to the firing of the device. The ram 60 is moved toward the distal end of the injector 10 by an energy source, which in some embodiments is a compression spring 52, although in other embodiments other suitable energy sources can be used such as elastomer or compressed-gas springs, or a gas generator. An example of a compression spring 52 suitable for use with injectors of the present disclosure is a coil spring. Alternative embodiments can also use other suitable trigger mechanisms as known in the art.

A latch housing 64 can be provided exterior to the inner housing 54 to retain the trigger protrusions 56 in the blocking association in the recess 58 to hold ram 60 in the proximal position until firing is actuated. Latch 64 is slideable inside outer housing 14 with respect to the inner housing 54, in some embodiments in an axial direction, and in some embodiments latch 64 surrounds the inner housing 54. In some embodiments latch 64 is free to move relative to outer housing 14 and is only secured in place, after the removal of safety member 80, by the pressure exerted thereon by trigger protrusions 56. In several aspects, nothing is present that biases latch housing 54 away from the proximal end of outer housing 14, including springs or the like. Alternative embodiments can use a medicament container that is shuttled forward when the device is activated to pierce the skin with the needle, and some embodiments use trigger mechanisms that are activated by a button on another part of the injector, such as at the proximal end or on a side of the housing as known in the art.

The housing 14 can have a needle guard 66 that is moveable with respect to the outer housing 14. In the embodiment of the needle guard 66 shown in FIG. 2, the needle guard 66 is in a protecting position, in which the needle 24 is disposed within the guard 66. A ridge 65 (FIG. 8) abuts an interior surface of outer housing 14 so as to maintain needle guard 66 within housing 14 when needle guard 66 is fully extended into the protecting position. The needle guard 66 can be retractable, in some embodiments into the outer housing 14, in a proximal direction to an injecting position, in which the needle tip 26 and an end portion of the needle 24 are exposed as shown in FIGS. 6B and 6C for insertion into a patient. In some embodiments, the proximal movement of the guard 66 is prevented at the injecting position.

The needle guard 66 can be associated with the latch 64 such that when the guard 66 is displaced proximally it slides the latch 64 in a proximal direction to release the trigger protrusions 56 from the recess 58. In some embodiments, the latch 64 has a latching portion 68 that abuts the inner housing 54 in an association to bias and maintain the trigger protrusions 58 positioned in the blocking association with the ram 60 prior to the firing of the injector 12. In some embodiments, when the latch 64 is slid proximately by the retracting of the guard 66 to the injecting position, the latching portion 68 slides beyond the portion of inner housing 54 that it contacts and flexes the trigger protrusions 56 away from the recess 58 of the ram 60, allowing the trigger protrusions 56 to move radially outwardly from the recess 58 and therefore from the blocking association. When this happens, spring 52 biases the ram 60 against plunger 28 to fire the injector 12.

In some embodiments, a cap 110 can be affixable on the distal end of the injector 12 so as to cover needle guard 66 and prevent accidental displacement thereof during shipping or during handling prior to injection. Cap 110 can affix to the distal end of outer housing 14 by press-fit, screw fit or the like. In certain embodiments, cap 110 can include a pair of projections 112 extending inwardly (FIG. 9), that form a distally-facing ridge 114. In such embodiments, needle guard 66 can be formed with a pair of radially-extending flanges 67 (FIG. 8) that are configured to abut the distal ridge 114 of projection 112 to secure cap 110 to injector 12. In some embodiments, the upper edge 116 (FIG. 9) of cap 110 can abut the distal end of outer housing 14 such that distal ridges 114 of projection 112 are held against flanges 67. This arrangement of the cap 110 prevents compression of the needle guard 66 proximally into the housing, as the cap 110 is juxtaposed between the guard 66 and housing, securing needle guard 66 in the protecting position to help prevent accidental firing of the injection mechanism.

In some embodiments, cap 110 can be removed from injector 12 by twisting cap 110 relative to housing 14 such that projections 112 are moved out of alignment with flanges 67, which allows the cap 110 to be moved distally away from needle guard 66. To prevent accidental removal of cap 110 from injector 12 due to inadvertent twisting of cap 110, in sonic embodiments the cap 110 engages the housing 14 and/or the needle guard 66 to require an initially elevated force, such as requiring the cap 110 to snap away from its closed position before completing the rotation to remove the cap 110. For example, upper edge 116 of cap 110 can be inclined, as shown in FIG. 9. The incline can include a curve, as shown, but generally the edge 116 can have one edge 118 that is higher than the other edge 120. In some embodiments, the distal end of outer housing 14 can have a profile that matches that of upper edge 118 of cap 110. This arrangement requires deflection of cap 110 to allow for twisting thereof and increases the force necessary to cause cap 110 to twist relative to needle guard 66. In an alternative embodiment, the cap 110 can have a threaded or cammed association with the flanges 67, or can have another arrangement therewith so that the cap 110 is removed by rotating.

Cap 110 can be attached to injector 12 during assembly thereof. This can be clone by properly aligning cap 110 and twisting it relative to needle guard 66 while applying a proximally-directed force thereto such that projections 112 move behind flanges 67. Alternatively, flanges 67 can be structured to be deflectable inwardly by disposing them on a corresponding tab 69 formed on needle guard 66. In such an embodiment, cap 110 can be assembled onto needle guard 66 prior to assembly of spring 72 thereinto, as spring 72 can interfere with the inward deflection of flanges 67. Alternatively, cap 110 can be resiliently deformable to allow cap 110 to be pressed onto needle guard 66 such that projections 112 pass over flanges 67.

In some embodiments, needle guard 66 can be resiliently biased distally towards the protecting position by compression coil spring 72. Also, the needle guard 66 can have an axial opening 74 to allow the needle 24 pass therethrough, and which may be sized according to the type of injector desired. In some embodiments, the construction of the injector 12 allows a user to push the distal end of the injector 12 against the patient's skin, pushing the needle 24 into the skin at an insertion location, substantially at the same speed as the injector 12 is pushed into the skin. Once the needle 24 is fully inserted to an insertion point at a desired penetration depth, the trigger mechanism fires causing the injector 12 to inject the medicament into an injection site.

In some embodiments, such as for subcutaneous injection using a needle-assisted jet injector, the needle guard 66 can be configured to allow insertion of the needle 24 to a penetration depth in the skin that is up to about 5 mm below the skin surface. In some embodiments, the penetration depth is less than about 4 mm, and in some embodiments less than about 3 mm. In some embodiments, the insertion depth is at least about 0.5 mm and in some embodiments at least about 1 mm. In another embodiment, the distance by which the needle tip 26 extends past the needle guard 66 or the distal surface of the needle guard 66 that contacts the skin is up to about 5 mm, in some embodiments up to about 4 mm, and in some embodiments up to about 3 mm. In some embodiments, extension distance is at least about 0.5 mm, in some embodiments at least about 1 mm, and in some embodiments at least about 2 mm. In some embodiments, needle tip 26 extends past the needle guard 66 by a distance of at least about 2.5 mm beyond the portion of the needle guard 66 that contacts the skin in the injecting position.

In another embodiment, such as for intramuscular injection using a needle-assisted jet injector, the injector 12 can be configured to allow the needle 24 to be inserted into the patient to a penetration depth in the skin, or alternatively beyond the distal surface of the needle guard 66, by a distance of up to about 15 mm. In some embodiments, this distance can be between about 10 mm and about 14 mm. In some embodiments, penetration depth of the needle tip 26 or distance beyond the needle guard 66 can be between about 12 mm and about 13.5 mm, and in some embodiments about 12.7 mm. Other exposed needle 24 lengths can be selected for jet injection to different depths below the skin, with an overall penetration length of between about 0.5 mm and about 20 mm. In these embodiments, the needle guard 66 can be configured for retracting from a protecting position, in some embodiments covering the entire needle, to an injecting position, in which the desired length of the tip 26 of the needle 24 is exposed.

Safety member 80 can be removably affixed to the distal end of outer housing 14 and can include a body portion 84 and a pair of resiliently-flexible legs 82 extending therefrom (FIGS. 4A and 4B). Legs 82 are configured to extend into corresponding holes or slots 15 formed in the proximal surface of outer housing 14 and can be shaped to provide a pressure fit within slots 15 to retain safety member 80 on housing 14. The legs 82 can be biased outwardly and can further include tabs 86 disposed on the outside surfaces thereof to engage the inside of outer housing 14 at the location of slots 15 to further the retention of safety member 80 onto outer housing 14. In some embodiments, legs 82 are shaped to allow a user to remove safety member 80 from outer housing 14, when injection is desired. In some embodiments, however, legs 82 prevent safety member 80 from becoming accidentally or unintentionally dislodged from its attachment to outer housing 14.

Legs 82 abut (FIG. 3) the proximal-most surface of latching portion 64 when properly attached to outer housing 14 to hinder or prevent jostling or other motion of latching portion 64 in the proximal direction, which would cause the injection mechanism to fire. In sonic embodiments, legs 82 are configured in relationship to the housing 14 and the trigger mechanism of the injector 12 such that the force necessary for latching portion 64 to move legs 82 out of slots 15 is sufficient to prevent latching portion 64 from being jostled out of position due to vibration during shipping or from acute shock during shipping or handling caused by dropping of injector 12. Alternative safety members can be used to prevent inadvertent firing of the injector 12.

In an embodiment in which the injector 12 is configured as a needle-assisted jet injector, the spring 72 and the prefilled syringe 18 can be configured to jet inject a medicament such as a hazardous agent. Thus, the spring 72 applies a force on the plunger 28 that can be sufficient to elevate the pressure within the fluid chamber 22 to a level high enough to eject the medicament from the needle 24 as a fluid jet. In several embodiments, jet injection is an injection of medicament from the needle tip 26 of the injector 12 with sufficient velocity and force to drive the medicament to locations remote from the needle tip 26.

Several jet injector embodiments, whether needle-assisted or needle-free, have an energy source selected to produce a high pressure in the medicament chamber 22 to eject the medicament therefrom with sufficient force and speed to exit the injector 12 as a fluid jet. It is believed that jet injectors deliver medicaments rapidly over a wider surface area under the subject's skin, by essentially "spraying" the medicaments into a subject subcutaneously, thereby rapidly exposing a greater surface area of the subject's target tissue to the medicaments.

When delivered by an autoinjector, a medicament typically leaves the autoinjector and is deposited locally, since it is not shot remotely from an injection outlet, and is thus delivered in a bolus near the needle tip of the autoinjector. This is because an autoinjector requires additional injection time to deliver an injection into resistive media, such as tissue, as opposed to delivery into air. In contrast, embodiments of a powered injector disclosed herein, and in particular embodiments of a disclosed jet injector, display no difference in injection time when injecting into resistive media versus air. Because the medicament delivered by a jet injector is essentially sprayed rapidly into the subject's tissue, remotely from the needle tip, the medicament does not leave the jet injector as a single drop or bolus and is this not delivered to a subject as a bolus local to a needle tip. Therefore, by using the jet injectors disclosed herein, a medicament can be dispersed into a subject's tissue more efficiently. Additionally, because jet injectors deliver medicaments via high pressure and speed, the delivered medicaments have a far lower tendency to leak back out of the injection site around the needle or injection track. Therefore, leak-back from the depth the medicament is delivered back toward the injection site, and/or back to the surface of the subject's skin, can be significantly reduced by use of a jet injector. Therefore, when used to deliver one or more medicaments according to the present disclosure, such as, for example, one or more hazardous agents, jet injectors significantly reduce the risk of exposure to the medicaments outside of the injection site, thereby reducing the risk of exposure to the medicaments to non-users and to the subject himself, in addition to reliably delivering the entire dose to the desired depth. Preventing or reducing leak-back is beneficial in improving compliance by ensuring that the medicament remains at the injection site at the desired depth. This not only improves the effectiveness of the delivery, but also avoids migration of medicaments from the injection site to other tissues, layers of tissue, and/or outside of the injection site. Preventing or reducing leak-back can also be beneficial to keeping medicaments such as hazardous agents contained to a single area, thereby preventing inadvertent exposure to the subject and/or to other individuals in his vicinity from leak-back to the surface of the skin. Such exposure can include, for example, direct contact with the medicament on the subject's skin or from atomized medicament that may reach the subject or nearby individuals through the air, or though another medium. Additionally, in many cases, patients who use the slow injection of a hand-powered hypodermic syringe or autoinjector risk removing the hand-powered injector from the injection site prematurely, before the shot is completed, leading to exposure of the medicament outside the patient's tissue, and in some instances leading to aerosolizing of the harmful medicament. This is often due to the long injection time required for injections via hand-powered hypodermic syringes or autoinjectors, which can be on the order of 5, 10 or 15 seconds or sometimes longer.

In some embodiments, the injector 12 is configured, and the injection conducted, to deliver a medicament such as, for example, a hazardous agent, that is harmful to the patient or other individuals, by jet injection in a manner to prevent or significantly reduce leak-back and the risk and incidence of undue exposure of the medicament to the air or to the outside surface of the patient's skin.

Table 1 shows the results of a trial comparing medicament leak-back that reached the surface of the skin of a subject after injection; data for needle-assisted jet injectors as compared to hand-driven hypodermic syringes is presented. The total number of injections for each group in the trial was 126, and all were administered by a trained health care professional.

TABLE 1

Medicament leak-back to the surface of the skin of a subject post injection. % = percent of the total 126 injections administered.

| Injection site assessment post-injection | Needle-assisted jet injector | Syringe and needle |
|---|---|---|
| Site completely dry | 89 (71%) | 76 (60%) |
| Slight wetness on site | 36 (29%) | 50 (40%) |
| Measurable wetness, but slight (a drop) | 1 (0%) | 0 (0%) |
| Considerable wetness at injection site | 0 (0%) | 0 (0%) |

Because jet injectors deliver medicaments rapidly, in some embodiments in less than about 2 seconds, the amount of time patients must hold the injector in their tissue is dramatically decreased as compared to an injection delivered by a typical syringe or autoinjector. It is therefore believed that utilizing jet injectors according to the present disclosure will result in increased patient compliance and adherence to instructions and will therefore result in an increase in correctly administered injected doses. Additionally, the speed at which jet injectors deliver medicaments can further enhance patient compliance with regular injections as the amount of pain experienced by a patient self injecting a medicament will be minimized and, in many cases, may not exist.

Figure 10:
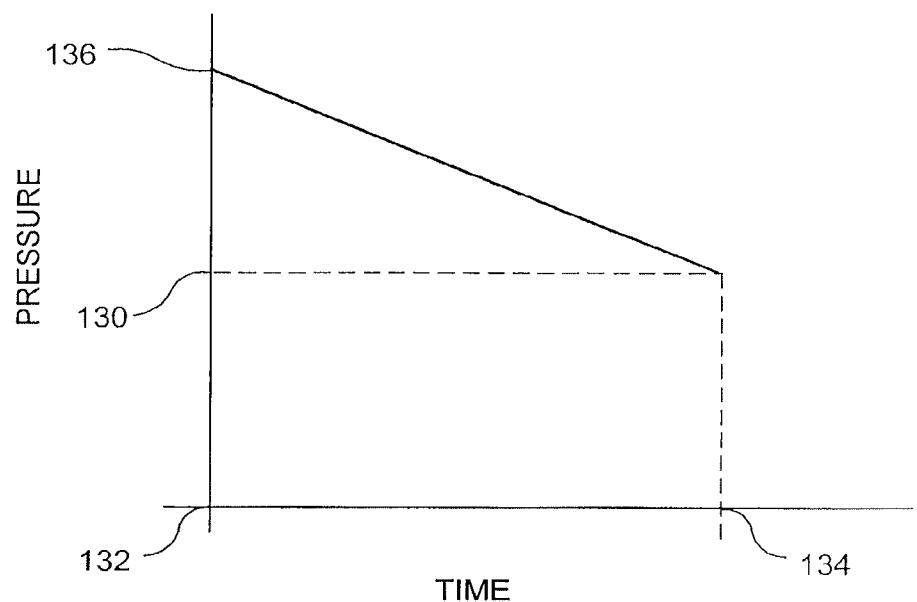
FIG. 10 is a graph showing the pressure within the liquid chamber of an embodiment of an injection device according to the present disclosure, as a function of time.

Referring to the graph shown in FIG. 10, numeral 132 represents the point in time when an embodiment of injector 12 is fired, and numeral 134 represents the point of completion of injection. In some embodiments, injection is completed when the plunger 28 hits the distal wall of the medicament container 20. Numeral 136 represents the initial and peak pressure during the injection, and numeral 130 represents the final pressure during the injection. In some embodiments, the spring 72 has a linear spring constant and an injection-assisting needle 24 is used to puncture the skin before commencing the injection. The pressure of injection therefore drops substantially linearly from the start of the injection 132 until the injection is completed 134. The final pressure 130 at the end 134 of the injection is sufficiently elevated so that even at the end of the firing stroke of ram 60, the medicament is still jet injected, and a very small amount or none of the medicament is deposited in a bolus around the needle tip 26, In some embodiments of needle-assisted jet injectors, the peak pressure 136 during the injection is less than about 1,000 p.s.i., in some embodiments less than 950 p.s.i., in some embodiments less than 900 p.s.i., in some embodiments less than 850 p.s.i., in some embodiments less than 800 p.s.i., in some embodiments less than 750 p.s.i., in some embodiments less than 700 p.s.i., in some embodiments less than 650 p.s.i., in some embodiments less than 600 p.s.i., in some embodiments less than 550 p.s.i., in some embodiments less than 500 p.s.i., in some embodiments less than 450 p.s.i., in some embodiments less than 400 p.s.i., and in some embodiments less than about 350 p.s.i. In some embodiments, at the end 1080 of the injection, the pressure 130 applied to the medicament in the fluid chamber 22 can be at least about 80 p.s.i., in some embodiments at least about 90 p.s.i., in some embodiments at least about 100 p.s.i., in some embodiments at least about 150 p.s.i., in some embodiments at least about 200 p.s.i., in some embodiments at least about 250 p.s.i., in some embodiments at least about 300 p.s.i., in some embodiments at least about 350 p.s.i., in some embodiments at least about 400 p.s.i., in some embodiments at least about 450 p.s.i., and in some embodiments at least about 500 p.s.i. In some embodiments, the initial pressure 136 can be about 330 p.s.i., and the final pressure 130 is about 180 p.s.i. In some embodiments, the initial pressure 136 is about 300 p.s.i., dropping to around 110 p.s.i. at the end 134 of the injection. Other injection rates are used for other embodiments discussed herein. For example, needle-free jet injectors can exert an injection pressure in the range of about 4,000 p.s.i. or greater. Other embodiments of jet injectors utilize lower injection pressures, such as at least about 80 p.s.i. or at least about 60 p.s.i. In contrast, known autoinjectors typically use pressures lower than 60 p.s.i.

The needles used in some embodiments of both autoinjectors and needle-assisted jet injectors are between 26 and 28 gage, and in some embodiments are around 27 gage. Other needle gages can also be used where the other components are cooperatively configured to produce the desired injection including, for example, mini-needles. In some embodiments, the components of the injector 12 can be configured to jet inject one or more medicaments to a subcutaneous injection site.

The amount of medicament contained in and injected from fluid chamber 22 can be between about 0.02 mL and about 4 mL, in some embodiments less than about 3 mL, and in some embodiments is about 1 mL. Larger volumes may also be selected depending on the particular medicament(s) utilized and dosage required. In some embodiments, a pre-filled syringe 18 containing the desired amount of medicament is assembled into the remaining parts of a jet injector 12. In some embodiments, the pre-filled syringe 18 contains from about 0.02 mL to about 4.00 mL of one or more medicaments. In some embodiments, the pre-filled syringe 18 contains about 1 mL of one or more medicaments.

In embodiments of needle-assisted jet injectors, injection rates are below about 0.75 mL/sec., in some embodiments below about 0.6 mL/sec., in some embodiments at least about 0.2 mL/sec., in some embodiments at least about 0.3 mL/sec, and in some embodiments at least about 0.4 mL/sec. In some embodiments, the injection rate is selected from below about 0.75 ml/sec, below about 0.7 ml/sec, below about 0.65 ml/sec, below about 0.6 ml/sec, below about 0.55 ml/sec, below about 0.5 ml/sec, below about 0.45 ml/sec, below about 0.4 ml/sec, below about 0.35 ml/sec, below about 0.3 ml/sec, and below about 0.25 ml/sec. In some embodiments, the injection rate is selected from at least about 0.2 ml/see, at least about 0.25 ml/see, at least about 0.3 ml/sec, at least about 0.35 ml/see, at least about 0.4 nil/see, at least about 0.45 ml/sec, at least about 0.5 ml/sec, at least about 0.55 ml/sec, at least about 0.6 ml/sec, at least about 0.65 ml/sec, and at least about 0.7 ml/sec. In some embodiments, the injection of the entire amount of medicament is completed in less than about 5 seconds, in some embodiments in less than about 4.5 seconds, in some embodiments in less than about 4 seconds, in some embodiments in less than about 3.5 seconds, in some embodiments in less than about 3 seconds, in some embodiments in less than about 2.5 seconds, in some embodiments in less than about 2 seconds, and in some embodiments in less than about 1.5 seconds. In some embodiments, the medicament injection takes at least about 1 second, in some embodiments at least about 1.5 seconds, in some embodiments at least about 1.75 seconds, in some embodiments at least about 2 seconds, in some embodiments at least about 2.5 seconds, in some embodiments at least about 3 seconds, in some embodiments at least about 3.5 seconds, in some embodiments at least about 4 seconds, and in some embodiments at least about 4.5 seconds. In some embodiments, injection of the medicament occurs at about 0.5 mL/sec., completing an injection of 1 mL in about 1 second. In some embodiments, injection of 0.5 ml of medicament occurs in less than about 1 second. In some embodiments, injection of 1.0 ml of medicament occurs in less than about 2 seconds. Other injection rates however, are possible for the alternative embodiments of the injectors 12 disclosed herein. For example, in some embodiments injector 12 can be configured to deliver a typical flow rate for needle-free jet injection, which can be about 1.5 mL per second, and in some embodiments injector 12 can be configured to deliver a typical flow rate for an autoinjector, which can be about 0.5 mL in 0.3 seconds.

Injection rates can be affected by a number of factors such as, for example, the gauge of the needle used to inject the medicament, the viscosity of the medicament itself, the glide force of the plunger 28 in the syringe barrel, and the temperature of the medicament to be injected, as temperature can have a direct effect on viscosity. In various embodiments, tissue resistance does not impact the rate of injection embodiments of the injectors of the present disclosure are capable of achieving. In various aspects, these parameters can be selected and optimized in order to deliver a volume of injection in a desired manner. Such selection and optimization can be readily performed by a person having ordinary skill in the art without undue experimentation.

In some embodiments, a viscous medicament that would otherwise require a longer injection time can still be injected into a subject in the rates set forth above by varying the gauge of the needle. For example, in some embodiments a 26 gauge needle can be utilized with the needle-assisted injectors of the present disclosure to inject a viscous material, in some embodiments a 27 gauge needle can be utilized with the needle-assisted injectors of the present disclosure to inject a viscous material, and in some embodiments a 28 gauge needle can be utilized with the needle-assisted injectors of the present disclosure to inject a viscous material. In each of the foregoing embodiments, the rates of injection are the same as those rates disclosed above. Therefore, by varying the gauge of the needle according to the viscosity of the medicament to be injected, the rates of injection can be maintained. In some embodiments, a 72 gauge needle can be utilized with one or more embodiments of the injectors of the present disclosure to deliver 1.0 ml of an aqueous solution into air in a duration of time from between about 1.0 to about 2.0 seconds, in some embodiments between about 1.5 and about 2.0 seconds, and in some embodiments in about 1.7 seconds. In some embodiments, a 72 gauge needle can be utilized with one or more embodiments of the injectors of the present disclosure to deliver 1.0 ml of an aqueous solution into tissue in a duration of time from between about 1.0 to about 2.0 seconds, in some embodiments between about 1.3 and about 2.0 seconds, in some embodiments in about 1.5 seconds, and in some embodiments in about 1.3 seconds. In some embodiments, a 72 gauge needle can be utilized with one or more embodiments of the injectors of the present disclosure to deliver 1.0 ml of a viscous solution, having a viscosity equivalent to 10% w/w polyethylene glycol 20,000 in water, into air in a duration of time from between about 1.0 to about 5.0 seconds, in some embodiments between about 2.5 and about 5.0 seconds, in some embodiments in about 4.3 seconds, and in some embodiments in about 4.0 seconds. In some embodiments, a 72 gauge needle can be utilized with one or more embodiments of the injectors of the present disclosure to deliver 1.0 ml of a viscous solution, having a viscosity equivalent to 20% w/w polyethylene glycol 20,000 in water, into air in a duration of time from between about 10 to about 15 seconds, in some embodiments between about 12 and about 15 seconds, and in some embodiments in about 14 seconds.

The cgs physical unit for dynamic viscosity is the poise (P), which is more commonly expressed in ASTM standards as centipoise (eP). Typically, aqueous solutions at 20° C. have a viscosity of approximately 1 cP In several embodiments, injectors of the present disclosure can be configured to produce a flow rate, or a rate of injection, of 0.5 ml/second for aqueous solutions having a cP of, or close to, 1.0, through a 27 gauge needle. In several embodiments, injectors of the present disclosure can be configured to produce a flow rate, or a rate of injection, into skin of 0.5 ml/second for aqueous solutions having a eP of, or close to, 1.0, through a 27 gauge needle.

U.S. Pat. No. 6,391,003, discloses the experimental results of pressures that can be successfully applied to a medicament in a glass cartridge, using 26 and 27 gage needles. Table 2 illustrates exemplary injections with different peak pressures that can be used with a needle-assisted jet injector, especially when using a glass, prefilled syringe:

TABLE 2 exemplary injections that may be delivered by a needle-assisted jet injector.
Pressure and Time (sec.) to Inject 1 cc

| Pressure | 26 Gauge needle | 27 Gauge needle |
| --- | --- | --- |
| 150 p.s.i. | 2.1 | 4.2 |
| 200 p.s.i. | 1.9 | 3.9 |
| 240 p.s.i. | 1.7 | 3.3 |
| 375 p.s.i. | 1.4 | 3.1 |

A person having ordinary skill in the art will recognize that higher pressures and flow rates will typically, though not always, be used with shorter needle penetration into a patient's skin, to achieve jet injections with the appropriate dispersion to achieve the desired depth substantially without medicament leak-back. Alternative embodiments can use higher or lower injection pressures. For instance, needle-free injectors may use higher pressures to penetrate the skin without a needle, and autoinjectors will typically use lower pressures to simulate a hand-powered syringe injection.

In some embodiments of needle-assisted jet injectors, short needles can be used to inject medicaments to different parts of the skin, in some embodiments subcutaneously, without any leak-back. Using a needle 24 that extends about 2.5 mm beyond the distal surface of the needle guard 66, a 27 gauge needle 24, and a pressure in the fluid chamber 22 peaking at about 300 and ending at around 100 p.si., resulting in a flow rate of about 0.5 mL/sec., 1 mL of medicament can be successfully be injected without significant leak-back in about 100% of the tested injections as shown, for example, in Table 1 where only slight or measurable, but still slight, wetness at an injection site was observed. Thus, needle-assisted jet injectors of the present disclosure permit jet injection of one or more medicaments using a very short needle reliably, regardless of the thickness of the patient's skin, age, weight or other factors.

In some embodiments, selection of the type of spring as a power source, adjustment of the force delivered by the spring, and/or the manner in which the spring is packaged within the assembled injector can lead to a significant reduction in the amount of time required to deliver a complete injection into a subject, a significant reduction in the spring force required to deliver the injection, and a longer shelf-life. For example, the spring present in many known autoinjectors is configured so that a typical injection, in the volume range of about 0.8-1.5 ml, is completely delivered into a subject in 10-15 seconds. In contrast, embodiments of the injectors of the present disclosure can have their spring configured so as to deliver a complete injection of about 0.8-about 1.0 ml in volume in about 1 to about 5 seconds, in some embodiments in about 2 to about 4 seconds, and in some embodiments in about 3 seconds. It is believed that this decrease in time will increase patient compliance when embodiments of the autoinjectors of the present disclosure are used, as less time is required to deliver a complete injection and, thus, the patient will experience less pain.

Figure 16:
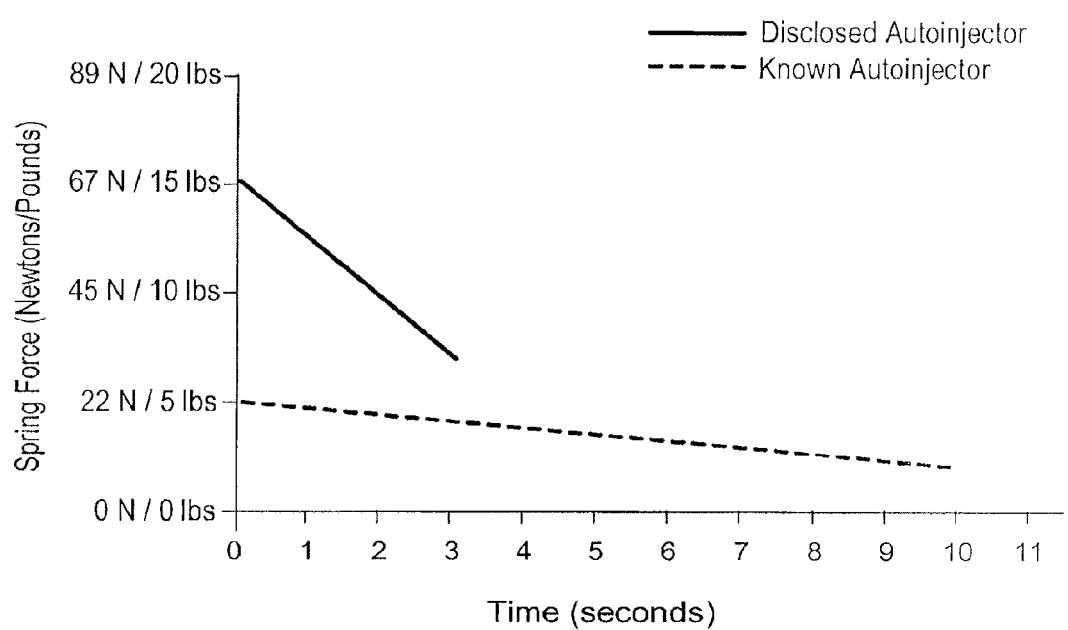
FIG. 16 shows a comparison of spring force during injection between an embodiment of an autoinjector of the present disclosure and a known autoinjector.

Additionally, in some embodiments spring material can be selected so as to only allow a decrease in spring force over the stroke length of the injection as shown, for example, in FIG. 16. Many known autoinjectors show a decrease in spring force over the course of a single injection of less than approximately 20%. In contrast, embodiments of the injectors of the present disclosure can be configured so that their spring force decreases by at least about 25% over the course of a single injection, in some embodiments from about 25% to about 50% over the course of a single injection, in some embodiments from about 30% to about 50% over the course of a single injection, and in some embodiments by about 50% over the course of a single injection.

Spring material can also be selected, and/or the spring can be set in the injector, so as to not have the spring in an overly compressed state during packaging and shipment of the spring to an end user or patient. This is advantageous because springs that are overly compressed for expended periods of time become over-stressed and show a loss of force over time. For example, many known autoinjectors are packaged such that they spend most of their shelf-life with their springs compressed. When packaged in this manner, such known autoinjectors experience a decrease in spring force over time as the autoinjector sits on a shelf awaiting use. In contrast, embodiments of the injectors of the present disclosure can have springs that are made of a material that is sufficiently resilient so as to lose less force over time as it is compressed, and/or can have a spring configured in a fully assembled injector such that it is not in a fully compressed state until the time of injection. In this manner, embodiments of the injectors of the present disclosure lose from about 0% to about 15% of their spring force over a typical shelf life. In some embodiments, the injectors of the present disclosure lose from about 10% to about 12% of their spring force over a three year shelf life.

In some embodiments of single-shot injectors, injector 12 includes a disabling mechanism, such as a locking element, which can be provided as a locking ring 70 associated with the injection mechanism. As shown in FIGS. 6A-6D, locking ring 70 can be disposed between sleeve 16 and needle guard 66, and can interact with sleeve 16 and needle guard 66 such that the locking ring 70 only permits needle guard 66 to move relative to outer housing 14 through a single injection cycle. This includes movement from the protecting position (FIG. 6A) into the injecting position (FIGS. 6B, 6C) and then to return to the protecting position (FIG. 6D) under the force of compression spring 72. When needle guard 16 returns to the protecting position at the end of the injection cycle, locking ring is positioned relative to sleeve 16 and needle guard 66 such that further movement therebetween is restricted, thus disabling the injector from further making injections and retaining the needle 24 safely within the housing 14 of the injector 12.

Figure 6:
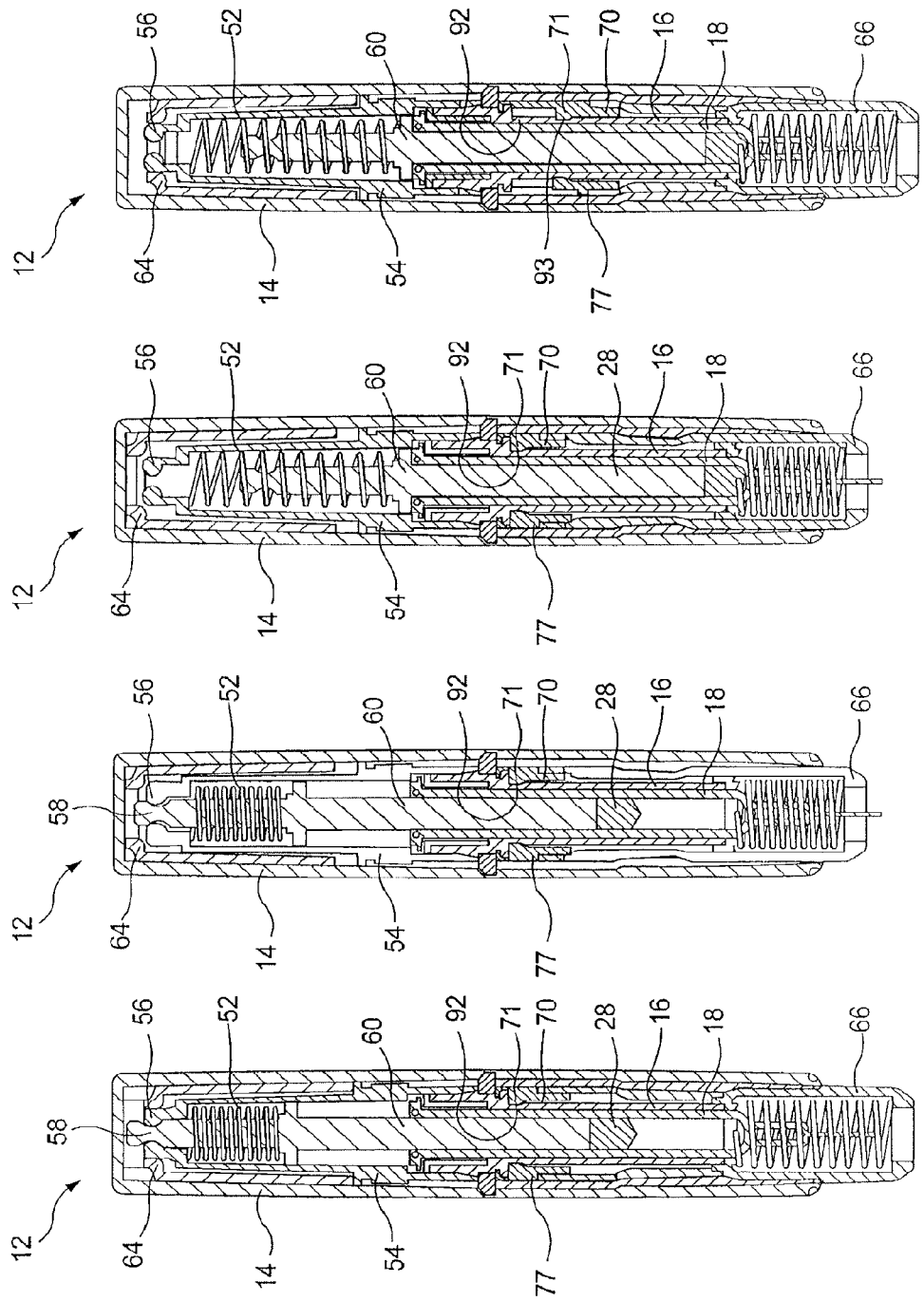
FIG. 6A is a cross-sectional view of the injection device of FIG. 1 in a ready state.
FIG. 6B is a cross-sectional view of the injection device of FIG. 1 at the start of an injection state.
FIG. 6C is a cross-sectional view of the injection device of FIG. 1 at the end of an injection state.
FIG. 6D is a cross-sectional view of the injection device of FIG. 1 in a locked state.
Figure 7:
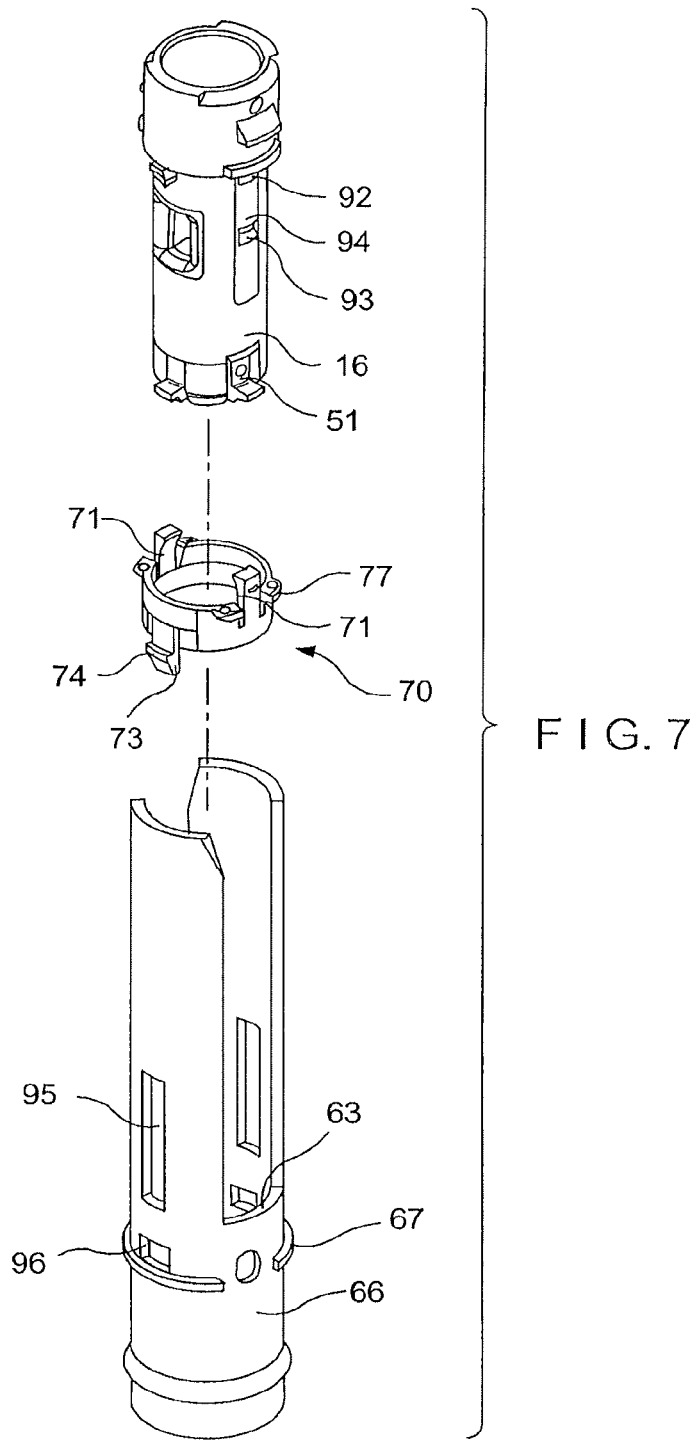
FIG. 7 is an exploded view of a portion of the trigger mechanism associated with the injection device of FIG. 1.

As shown in FIGS. 6A-6D, movement of needle guard 66 through one locking cycle causes locking ring 70 to move relative to sleeve 16 from an injecting position to a locking position. In the injecting position, locking ring 70 is disposed such that the upper arms 71 of locking ring 70 engage a portion of the device that is associated with the medicament chamber 22, such as, for example, proximal notches 92 formed in the outer surface of sleeve 16. The engagement of upper arms 71 within proximal notches 92 releasably maintains locking ring 70 in the injecting position. As shown in FIG. 7, locking ring 70 can be generally annular in shape so as to surround the medicament chamber 22, either directly or indirectly, such as by surrounding sleeve 16. Locking ring 70 further includes a pair of lower arms 73, each having a tab 74 formed on the end thereof. When locking ring 70 is in the injecting position, tabs 74 are received in slot 95 formed in needle guard 66 such that needle guard 66 is slideable through a predetermined distance over locking ring 70. As needle guard 66 is moved into the injecting position with respect to outer housing 14, needle guard 66 slides over locking ring 70 such that tabs 74 reach the end of slot 95 and are depressed inwardly, allowing needle guard 66 to continue to move into the injecting position. When the injecting position is reached, tabs 74 align with holes 96 of needle guard 66, allowing lower arms 73 to return to their natural position, wherein the upper surfaces of tabs 74 engage an edge of the holes 96, thereby coupling locking ring 70 to needle guard 66.

As needle guard 66 returns to the protecting position, needle guard 66 pulls distally on locking ring 70, causing upper arms 71 to release from proximal notches 92. In some embodiments, upper arms 71 and proximal notches 92 are formed with mating inclined surfaces such that the inclined surfaces of upper arms 71 engage another portion of the injector 12 that is associated with the medicament chamber 22, such as by extending into proximal notches 92, but are forced outwardly by distally-directed movement relative thereto. This configuration allows the needle guard 66 to cause locking ring 70 to move therewith and out of the injecting position as needle guard 66 moves distally toward the protecting position over sleeve 16, which remains stationary.

When needle guard 66 reaches the protecting position, upper arms 71 move over distal notches 93 formed in sleeve 16 such that the upper surfaces of upper arms 71 engage the upper surface 94 of distal notches 93. Further, in such a position, flange 77 of locking ring 70 abuts surface 67 of needle guard to block needle guard 66 from distal motion relative to locking ring 70. This engagement prevents locking ring 70 from moving proximally with respect to sleeve 16. Because locking ring 70 is coupled to needle guard 66 in this configuration, and because sleeve 16 is attached to outer housing 14, needle guard 66 is locked relative to outer housing 14, and is prevented from being moved back into the injecting position. This prevents needle 24 from being accidentally exposed after use of injector 12. Alternative embodiments can use other mechanisms to prevent re-use of the injector or portion thereof. Some embodiments do not employ such a mechanism so that the injector can be reused. In some embodiments, after injection of the medicament, subsequent injection can be prevented automatically and exposure to or contact with remnants of the medicament that may remain on portions of the injector after the injection, such as on a needle tip or jet injection nozzle, can also be prevented or avoided by the construction of the injector 12.

Figure 11:
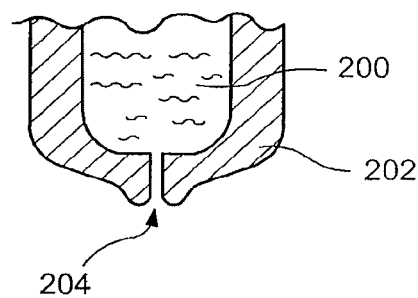
FIG. 11 is a cross-sectional view of a needle-free jet injection nozzle.

Referring to FIG. 11, a distal end of an embodiment of a needle-free jet injector is shown. The depicted injector can use the systems disclosed herein to fire the injection as described above for the needle injector embodiments, but instead of a needle, a jet nozzle 202 is used to inject the medicament into the subject. Nozzle 202 defines a jet outlet 204 having a diameter selected for causing the medicament 200 to exit the nozzle 202 as a fluid jet that is sufficiently strong to pierce the outer skin layers and to continue to the desired depth of injection.

EXAMPLES

The following examples describe in detail the injection and pharmacokinetics of one or more hazardous agents injected into one or more subjects using embodiments of the injectors disclosed herein. It will be apparent to those skilled in the art that many modifications, both to materials and methods, may be practiced without departing from the scope of the disclosure.

Example 1

A pharmacokinetic (PK) analysis was undertaken to describe and compare the systemic exposure of the hazardous agent methotrexate achieved in male and female Gottingen minipigs after subcutaneous administration, either with an autoinjector of the present disclosure or with a known hypodermic needle/syringe combination.

Both methotrexate and a control article were administered. Administration of the test and control articles, blood collection and processing for this study were performed at Charles River Preclinical Services (Spencerville, Ohio) under non-FDA compliant GLP (Good Laboratory Practice) conditions. The plasma concentration data presented were produced a Research Grade Level 3 liquid chromatography tandem mass spectroscopy (LC-MS/MS) method.

Methotrexate was administered via subcutaneous injection to minipigs, alternatively to the same set of animals with an autoinjector or needle/syringe. Injections were performed on Day 1 and Day 8. Table 3 illustrates the experimental design of the PK portion of the study.

TABLE 3

| Injection Device | Number of animals | Sex | Day[a] | Dose Material | Dose Level (mg/day) | Dose Volume (mL) | Dose Concentration (mg/mL) |
|---|---|---|---|---|---|---|---|
| Autoinjector | 3 | Males | 1 | Methotrexate | 12.5 | 0.5 | 25 |
|  | 3 | Females | 8 | Injection USP |  |  |  |
| Needle/Syringe | 3 | Males | 8 | Methotrexate | 12.5 | 0.5 | 25 |
|  | 3 | Females | 1 | Injection USP |  |  |  |

[a]The same 3 animals/sex were used on Day 1 and Day 8

Blood samples (approximately 1 mL) were collected from all animals, into $K_2$EDTA-containing tubes, according to the schedule in Table 4. All samples were processed to plasma prior to being analyzed for Methotrexate and the 7-OH metabolite concentrations. Plasma concentration results for the 7-OH metabolite were not subjected to PK analysis.

TABLE 4

| Number of Animals | | Pharmacokinetic Time Points (Hours Post Dose) - Day 1 and Day 8 | | | | | | | | | | |
|---|---|---|---|---|---|---|---|---|---|---|---|---|
| Males | Females | 0[a] | 0.25 | 0.5 | 0.75 | 1 | 1.5 | 2 | 4 | 6 | 8 | 12 | 24 |
| 3 | 3 | X | X | X | X | X | X | X | X | X | X | X | X |

[a] Sample collected prior to dosing.
X Sample collected.

The PK profile of each animal was characterized by non-compartmental analysis of Methotrexate plasma concentration data with targeted sampling time points using validated computer software (WinNonlin, Version 5.2.1, Pharsight Corp., Mountain View, Calif., U.S.A.). A model was selected based on the extravascular route of administration and the plasma matrix. Predose concentrations were assumed to be zero for the purpose of PK parameter estimation.

The area under the Methotrexate plasma concentration vs. time curves (AUC) was calculated using the linear trapezoidal method (linear interpolation). When practical, the terminal elimination phase of the PK profiles was identified based on the line of best fit using at least the final three observed concentration values. The slope of the terminal elimination phase was calculated using log-linear regression using the unweighted concentration data. PK parameters describing the systemic exposure of the test article in the test system were estimated from observed (rather than predicted) plasma concentration values, the dosing regimen, the AUC, and the terminal elimination phase rate constant ($K_{el}$) for each animal. Parameters relying on the determination of $K_{el}$ were not reported if the coefficient of determination of the line of best fit ($R_{sq}$) was less than 0.800, or the extrapolation of the AUC to infinity represented more than 20% of the total area.

Where appropriate, numerical data obtained during the conduct of the study were subjected to calculation of descriptive statistics (mean and standard deviation) in Microsoft Excel, 2000/2003.

As shown in Tables 5 and 6, Methotrexate was above the lower limit of quantitation (LLOQ=0.2 ng/mL) in a few samples collected prior to dosing on Day 1 and Day 8: Male No. S5196559 (needle/syringe, Day 8, 0.558 ng/mL); Male No. S5196206 (needle/syringe, Day 8, 0.222 ng/mL); and Female No. S5195684 (autoinjector, Day 8, 3.19 ng/mL). These results were attributed to carryover of the instrument, from a previous sample containing a high concentration of Methotrexate. Methotrexate was quantifiable in all post dose samples, with the exception of the 24 h sample from Male Nos. S5196273 and S5196206, after administration with autoinjector (Day 1).

TABLE 5

Concentrations of Methotrexate in Gottingen Minipig Plasma Following Subcutaneous Injection of Methotrexate with Autoinjector or Syringe
Dose Level: (12.5 mg/day)-Concentration (ng/mL)

| Injection Device | Nominal Time (h) | Males | | | |
|---|---|---|---|---|---|
| | | Animal S5196273 | Animal S5196559 | Animal S5196206 | Mean = SD |
| Auto-injector | Predose | BQL | BQL | BQL | BQL = n a |
| | 0.25 | 1230 | 1560 | 1660 | 1483 = 225 |
| | 0.5 | 828 | 1070 | 1120 | 1006 = 156 |
| | 0.75 | 585 | 762 | 668 | 672 = 88.6 |
| | 1 | 402 | 664 | 457 | 508 = 138 |
| | 1.5 | 232 | 461 | 228 | 307 = 133 |
| | 2 | 121 | 288 | 146 | 185 = 90.1 |
| | 4 | 26.7 | 66.1 | 25.6 | 39.5 = 23.1 |
| | 6 | 7.67 | 19.4 | 7.12 | 11.4 = 6.94 |
| | 8 | 4.30 | 7.83 | 2.73 | 4.95 = 2.61 |
| | 12 | 0.937 | 1.80 | 0.692 | 1.14 = 0.582 |
| | 24 | BQL | 0.696 | BQL | 0.232 = 0.402 |
| Syringe | Predose | BQL | 0.558 | 0.222 | 0.260 = 0.281 |
| | 0.25 | 1260 | 1920 | 1390 | 1523 = 350 |
| | 0.5 | 999 | 1510 | 1470 | 1326 = 284 |
| | 0.75 | 705 | 1110 | 1240 | 1018 = 279 |
| | 1 | 539 | 887 | 860 | 762 = 194 |
| | 1.5 | 245 | 637 | 490 | 457 = 198 |
| | 2 | 148 | 367 | 243 | 253 = 110 |
| | 4 | 25.0 | 67.9 | 36.0 | 43.0 = 22.3 |
| | 6 | 6.09 | 25.5 | 14.1 | 15.2 = 9.75 |
| | 8 | 1.91 | 5.82 | 2.54 | 3.42 = 2.10 |
| | 12 | 0.501 | 1.30 | 0.764 | 0.855 = 0.407 |
| | 24 | 0.269 | 0.780 | 0.894 | 0.648 = 0.333 |

BQL = Below the quantitation limit (BQL = 0.200 ng/mL) The BQL concentrations were assigned a value of zero for mean calculation.
n a = Not applicable

TABLE 6

Concentrations of Methotrexate in Gottingen Minipig Plasma Following Subcutaneous Injection of Methotrexate with Autoinjector or Syringe
Dose Level: (12.5 mg/day)-Concentration (ng/mL)

| Injection Device | Nominal Time (h) | Females | | | |
|---|---|---|---|---|---|
| | | Animal S5196028 | Animal S5195684 | Animal S5195757 | Mean = SD |
| Autoinjection | Predose | BQL | 3.19 | BQL | 1.06 = 1.84 |
| | 0.25 | 1530 | 2240 | 1720 | 1830 = 368 |
| | 0.5 | 1580 | 1640 | 1500 | 1440 = 178 |
| | 0.75 | 1180 | 1290 | 863 | 1111 = 222 |
| | 1 | 966 | 1040 | 627 | 878 = 220 |

TABLE 6-continued

Concentrations of Methotrexate in Gottingen Minipig Plasma Following
Subcutaneous Injection of Methotrexate with Autoinjector or Syringe
Dose Level: (12.5 mg/day)-Concentration (ng/mL)

| Injection Device | Nominal Time (h) | Females Animal S5196028 | Animal S5195684 | Animal S5195757 | Mean = SD |
|---|---|---|---|---|---|
| | 1.5 | 635 | 885 | 593 | 638 = 246 |
| | 2 | 410 | 549 | 217 | 392 = 167 |
| | 4 | 75.1 | 123 | 49.8 | 82.6 = 37.2 |
| | 6 | 25.1 | 29.3 | 20.4 | 24.9 = 4.45 |
| | 8 | 9.79 | 10.1 | 8.35 | 9.41 = 0.934 |
| | 12 | 6.20 | 2.43 | 1.77 | 3.47 = 2.39 |
| | 24 | 0.617 | 0.495 | 0.569 | 0.560 = 0.0615 |
| Syringe | Predose | BQL | BQL | BQL | BQL = n a |
| | 0.25 | 1550 | 1890 | 1180 | 1473 = 371 |
| | 0.5 | 1280 | 1520 | 1250 | 1350 = 148 |
| | 0.75 | 1010 | 1200 | 891 | 1034 = 156 |
| | 1 | 842 | 940 | 726 | 836 = 107 |
| | 1.5 | 667 | 681 | 398 | 582 = 160 |
| | 2 | 449 | 434 | 208 | 364 = 135 |
| | 4 | 66.0 | 84.3 | 62.3 | 70.9 = 11.8 |
| | 6 | 20.3 | 24.6 | 19.8 | 21.6 = 2.64 |
| | 8 | 14.0 | 10.0 | 18.7 | 14.2 = 4.35 |
| | 12 | 5.12 | 3.47 | 6.03 | 4.87 = 1.30 |
| | 24 | 0.244 | 0.905 | 0.230 | 0.460 = 0.386 |

Figure 12:
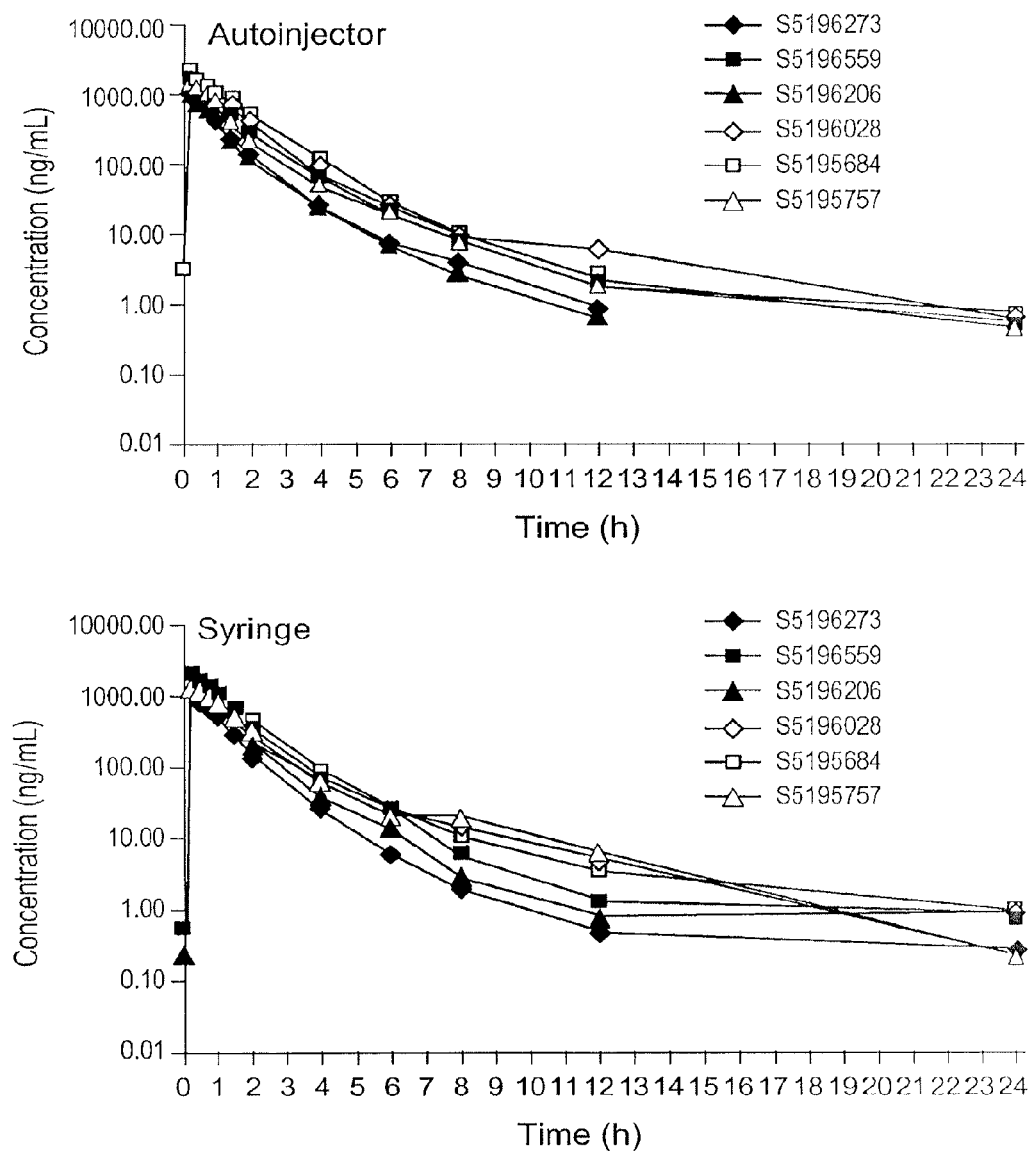
FIG. 12 shows the pharmacokinetic profiles of methotrexate in Gottingen minipig plasma following subcutaneous injection of methotrexate with an embodiment of an autoinjector of the present disclosure as compared to a known hypodermic syringe.

BQL = Below the quantitation limit (BQL = 0.200 ng/mL) The BQL concentrations were assigned a value of zero for mean calculation.
n a = Not applicable As shown in Table 7, FIG. 12, FIG. 13 and FIG. 14, maximal plasma concentrations of Methotrexate were generally observed at the first collection time point (0.25 1h) with both devices, indicating rapid absorption from the injection site. After $T_{max}$, Methotrexate concentrations declined in an apparently bi-exponential fashion. Where it could be estimated, the terminal elimination half-life of Methotrexate ranged from 1.81 to 4.90 hours.

TABLE 7

Pharmacokinetic Parameters of Methotrexate in Gottingen Minipig Plasma Following
Subcutaneous Injection of Methotrexate with Autoinjector or Syringe

| Injection Device | Dose Level (mg day) | Sex | Animal No. | Cmax (ng mL) | Tmax (h) | AUC(0-t) (ng · h mL) | AUC(0-inf) (ng · h mL) | T1 2 (h) | Cmax Dose | AUC(0-t) Dose |
|---|---|---|---|---|---|---|---|---|---|---|
| Autoinjector | 12.5 | Female | S5196028 | 1530 | 0.25 | 2498 | 2501 | 3.91 | 122 | 200 |
| | | | S5195684 | 2240 | 0.25 | 3169 | 3172 | 3.95 | 179 | 254 |
| | | | S5195757 | 1720 | 0.25 | 1857 | 1859 | 3.26 | 138 | 149 |
| | | | Mean [a] | 1830 | 0.25 | 2508 | 2511 | 3.71 | 146 | 201 |
| | | | SD | 368 | | 656 | 656 | 0.387 | 29.4 | 52.5 |
| | | Male | S5196273 | 1230 | 0.25 | 1162 | 1165 | 1.95 | 98.4 | 93.0 |
| | | | S5196559 | 1560 | 0.25 | 1901 | 1903 | 2.00 | 124.8 | 152 |
| | | | S5196206 | 1660 | 0.25 | 1405 | 1407 | 1.81 | 132.8 | 112 |
| | | | Mean [a] | 1483 | 0.25 | 1489 | 1491 | 1.92 | 119 | 119 |
| | | | SD | 225 | | 376 | 376 | 0.098 | 18.0 | 30.1 |
| Syringe | 12.5 | Female | S5196028 | 1350 | 0.25 | 2378 | 2378 | 2.74 | 108 | 190 |
| | | | S5195684 | 1890 | 0.25 | 2669 | 2675 | 4.90 | 151 | 214 |
| | | | S5195757 | 1250 | 0.50 | 1831 | 1832 | 2.53 | 100 | 147 |
| | | | Mean [a] | 1497 | 0.25 | 2293 | 2295 | 3.39 | 120 | 183 |
| | | | SD | 344 | | 425 | 428 | 1.316 | 27.5 | 34.0 |
| | | Male | S5196273 | 1260 | 0.25 | 1324 | b | b | 101 | 106 |
| | | | S5196559 | 1920 | 0.25 | 2464 | 2466 | 1.91 | 154 | 197 |
| | | | S5196206 | 1470 | 0.50 | 2016 | b | b | 118 | 161 |
| | | | Mean [a] | 1550 | 0.25 | 1935 | — | — | 124 | 155 |
| | | | SD | 337 | | 574 | — | — | 27.0 | 45.9 |

[a] Median value reported for Tmax.
b Values are not reported because the AUC(0-inf) was extrapolated by more than 20% or Rsq was 0.800.
— Not calculated.

Figure 14:
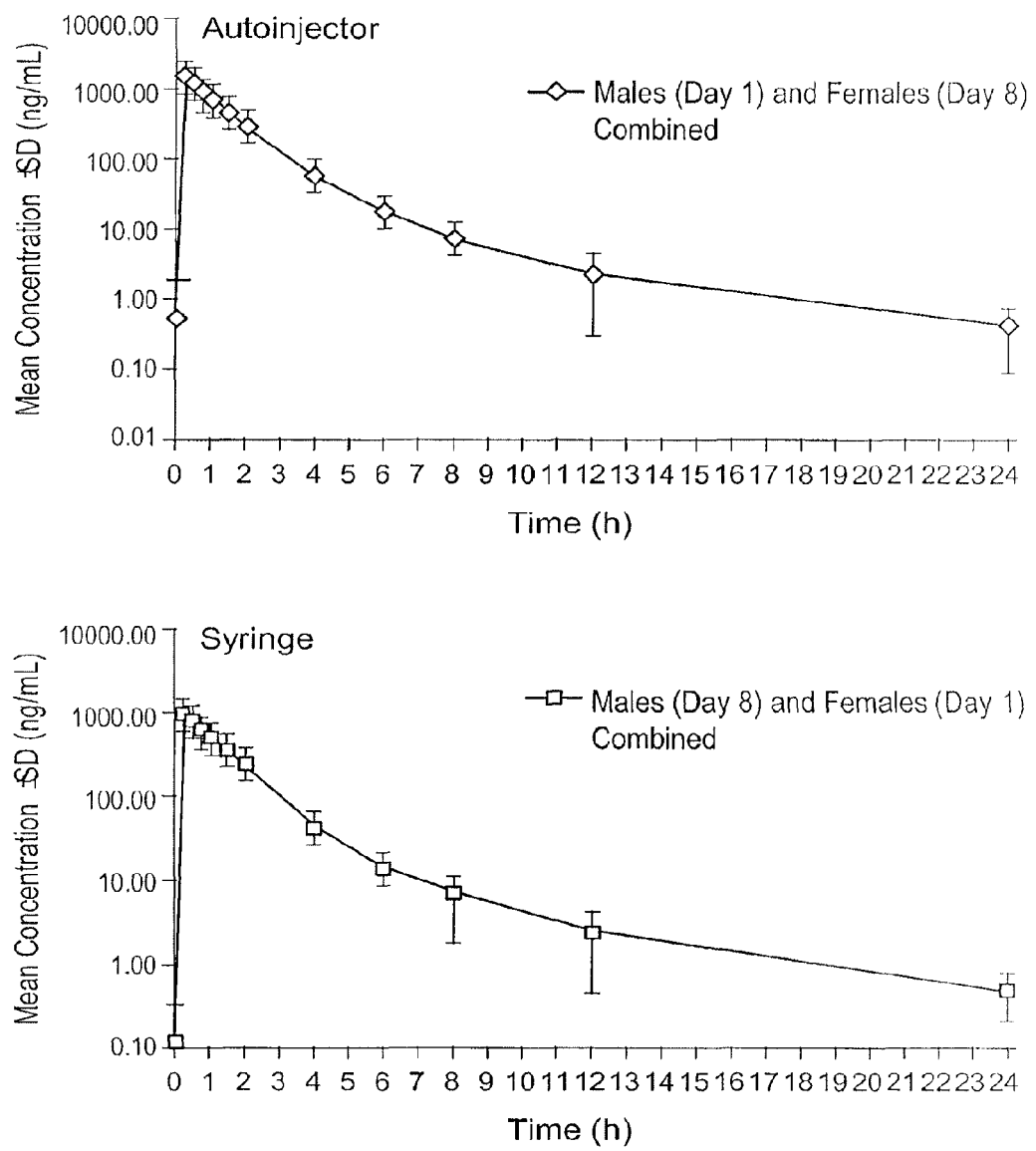
FIG. 14 shows further mean pharmacokinetic profiles of methotrexate in Gottingen minipig plasma following subcutaneous injection of methotrexate with an embodiment of an autoinjector of the present disclosure as compared to a known hypodermic syringe.
Figure 15:
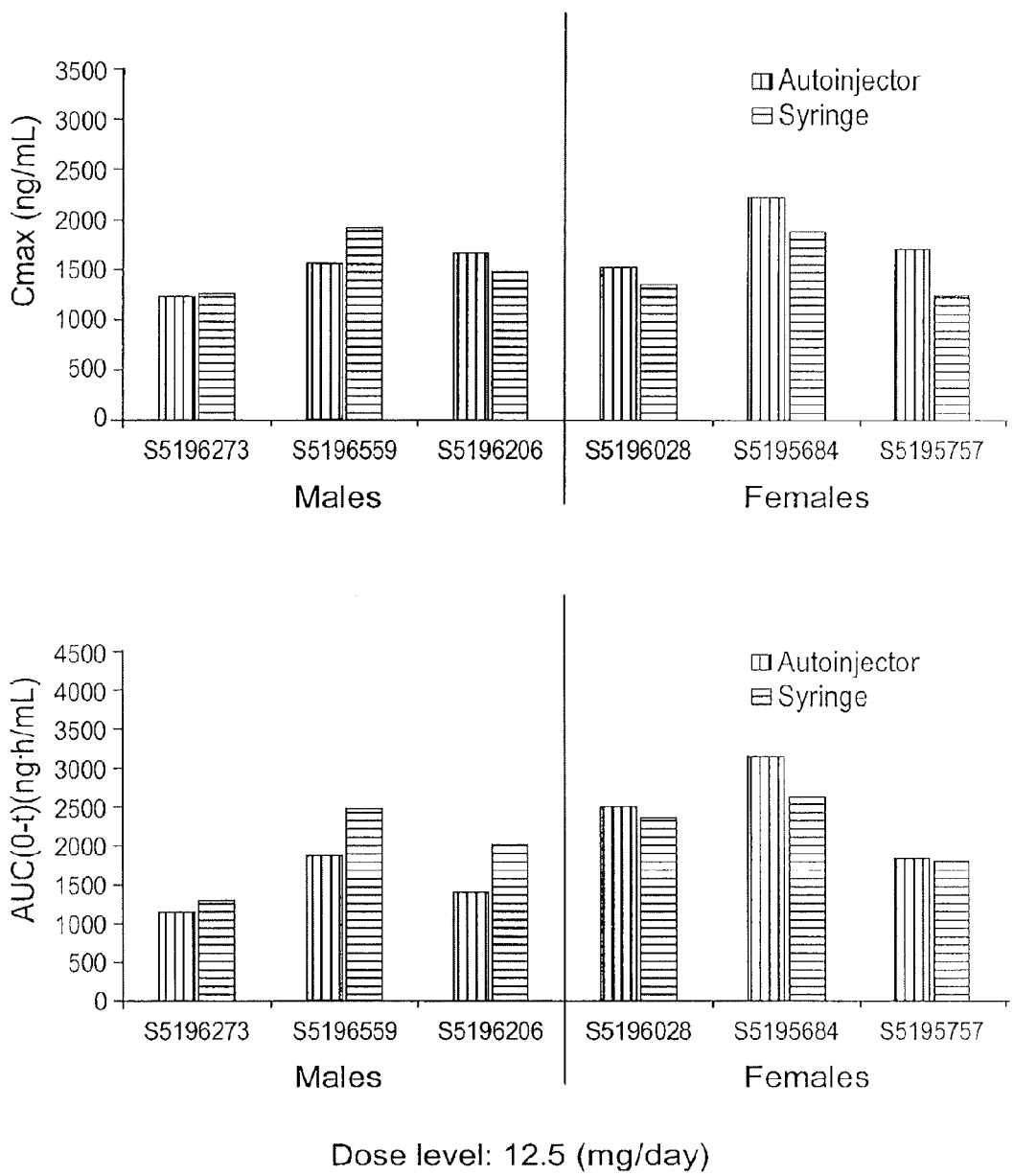
FIG. 15 shows a comparison of methotrexate exposure ($C_{max}$ and AUC(0-t)) in Gottingen minipig plasma following subcutaneous injection of methotrexate with an embodiment of an autoinjector of the present disclosure as compared to a known hypodermic syringe.

As shown in Table 7, Table 8, FIG. 14 and FIG. 15, exposures obtained with either the autoinjector or needle/syringe were very similar.

TABLE 8

| Sex | Animal ID | Methotrexate PK Parameters | Route of Administration | |
|---|---|---|---|---|
| | | | Needle/Syringe | Autoinjector |
| | | | Day 8 | Day 1 |
| Male | S5196273 | Cmax (ng/mL) | 1260 | 1230 |
| | | AUC(0-t) (hr * ng/mL) | 1324 | 1162 |
| Male | S5196559 | Cmax (ng/mL) | 1920 | 1560 |
| | | AUC(0-t) (hr * ng/mL) | 2464 | 1901 |
| Male | S5196206 | Cmax (ng/mL) | 1470 | 1660 |
| | | AUC(0-t) (hr * ng/mL) | 2016 | 1405 |
| | | | Day 1 | Day 8 |
| Female | S5196028 | Cmax (ng/mL) | 1350 | 1530 |
| | | AUC(0-t) (hr * ng/mL) | 2378 | 2498 |
| Female | S5195684 | Cmax (ng/mL) | 1890 | 2240 |
| | | AUC(0-t) (hr * ng/mL) | 2669 | 3169 |
| Female | S5195757 | Cmax (ng/mL) | 1250 | 1720 |
| | | AUC(0-t) (hr * ng/mL) | 1831 | 1857 |

Figure 13:
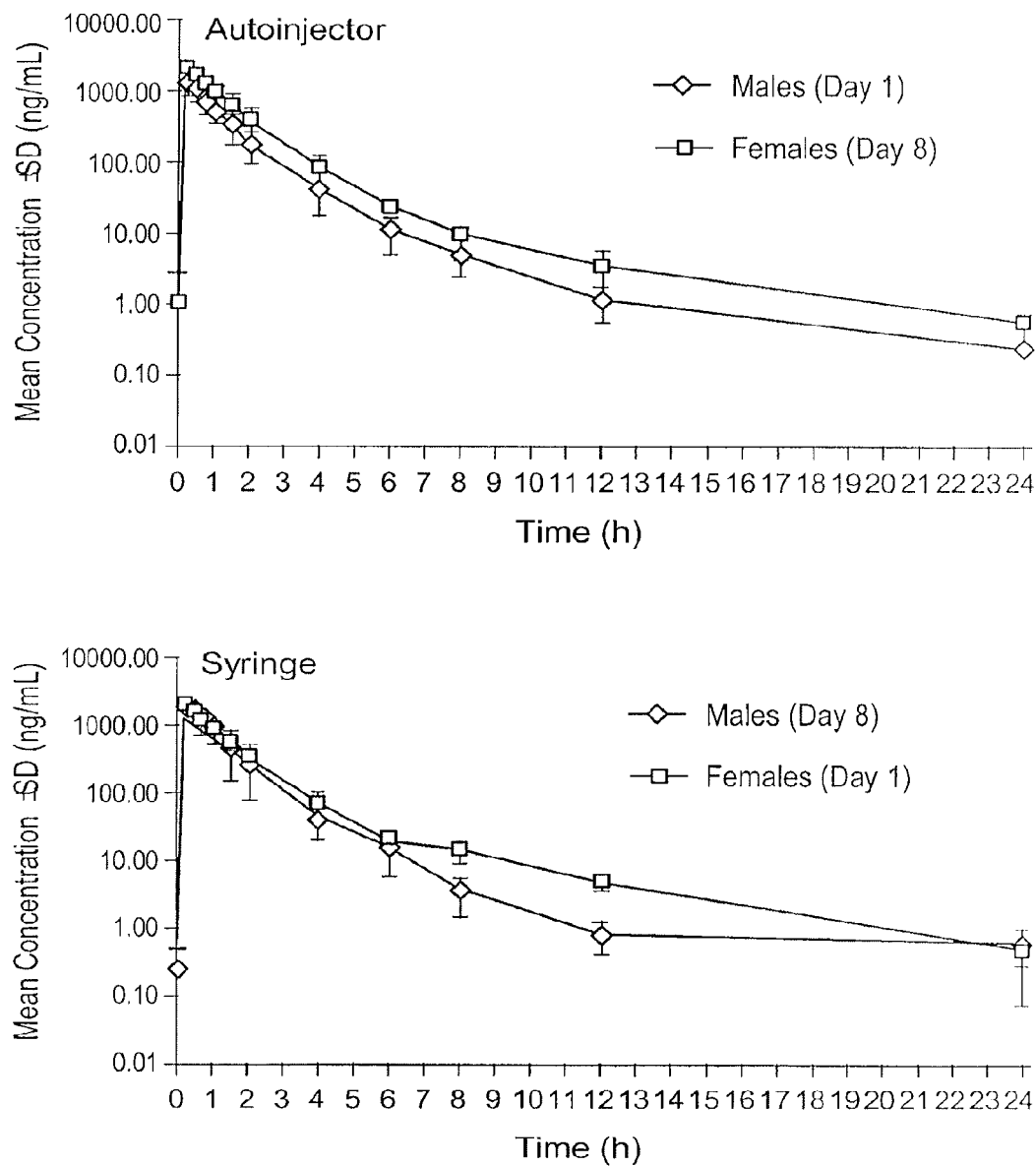
FIG. 13 shows the mean pharmacokinetic profiles of methotrexate in Gottingen minipig plasma following subcutaneous injection of methotrexate with an embodiment of an autoinjector of the present disclosure as compared to a known hypodermic syringe.

As shown in Table 7, FIG. 13 and FIG. 14, there was no marked difference in exposure between males and females, although a very slight trend towards greater exposure in females, especially through needle/syringe administration, was observed.

In summary, the pharmacokinetics of methotrexate in plasma was characterized in male and female Gottingen minipigs after subcutaneous administration of 12.5 mg, either with an autoinjector device or needle/syringe. Maximal concentrations of Methotrexate were generally observed shortly (0.25 h) after dose administration, and declined thereafter, in an apparent bi-exponential manner. The terminal elimination half-life of Methotrexate ranged from 1.81 to 4.90 hours. Exposure achieved with either the autoinjector or needle/syringe was comparable. There were no marked sex-related differences in PK parameters.

Example 2

A comparison of an injection between an autoinjector of the present disclosure and both the Enbrel® SureClick™ Autoinjector (Immunex Corporation, Thousand Oaks, Calif., U.S.A.) and the HUMIRA® pen (Abbott Laboratories, Abbott Park, Ill., U.S.A.), two known traditional autoinjectors, was undertaken to describe and compare both the spring force and the time required to deliver a complete injection of a solution in the range of 0.8-1.0 ml.

A control article was administered for this test. The results for the two known autoinjectors was averaged. The results of the comparison are shown in FIG. 16. As shown in FIG. 6, the time required to deliver a complete injection is 10 seconds for the known autoinjectors, whereas the time required to deliver a complete injection from the autoinjector of the present disclosure is only 3 seconds. Therefore, users of the known autoinjectors must retain those autoinjectors at the site of injection for a full 10 seconds in order to receive the full injection. In contrast, a user of the autoinjector of the present disclosure need only retain the autoinjector at the injection site for 3 seconds.

Additionally, as shown in FIG. 16, the spring force required to deliver a full injection decreases by approximately 50% in 3 seconds for the autoinjector of the present disclo-sure. This is in contrast with a decrease in spring force of less than approximately 20% in 10 seconds seen for the known autoinjectors.

The term "about," as used herein, should generally be understood to refer to both the corresponding number and a range of numbers. Moreover, all numerical ranges herein should be understood to include each whole integer within the range.

While illustrative embodiments of the disclosure are disclosed herein, it will be appreciated that numerous modifications and other embodiments may be devised by those skilled in the art. For example, the features for the various embodiments can be used in other embodiments. Therefore, it will be understood that the appended claims are intended to cover all such modifications and embodiments that come within the spirit and scope of the present disclosure.

What is claimed is:

1. A hazardous agent injection system, the hazardous agent injection system comprising:
   methotrexate in an amount of from about 0.02 ml to about 4.0 ml and at a concentration of from about 7.5 mg/ml to about 150 mg/ml in a pharmaceutically acceptable solvent;
   a powered injector, the powered injector comprising:
   a prefilled syringe, comprising a container including a pharmaceutical solution formulation of the methotrexate and a pharmaceutically acceptable solvent;
   an injection-assisting needle configured to pierce the skin of a patient and deliver methotrexate to the patient subcutaneously;
   a firing mechanism associated with the prefilled syringe and configured to expel the methotrexate from the prefilled syringe through the needle for injecting the methotrexate;
   an energy source associated with the firing mechanism and configured to power the firing mechanism and to inject the methotrexate from the injection outlet member; and
   a trigger mechanism associated with the firing mechanism and configured to activate the firing mechanism,
   wherein the powered injector is configured to subcutaneously inject the methotrexate from the prefilled syringe in less than 5 seconds, such that one or more of confidence intervals of (a) the maximum concentration of methotrexate in blood plasma of a patient following administration of a dose of the methotrexate to the patient ("$C_{max}$") with the hazardous agent injection system, (b) the time to reach the maximum concentration of methotrexate in blood plasma of a patient following administration of a dose of the methotrexate to the patient with the hazardous agent injection system ("$T_{max}$") and (c) area under the curve of the concentration of methotrexate in blood plasma of a patient following administration of a dose of the methotrexate to the patient with the hazardous agent injection system of the injected methotrexate ("AUC") falls between about 80% and about 125% of a measured confidence interval of the same dose of methotrexate delivered by a hand-powered syringe.

2. The hazardous agent injection system of claim 1, wherein the gauge of the injection-assisting needle is selected from 26 gauge and a higher gauge number.

3. The hazardous agent injection system of claim 1, wherein the powered injector is configured to inject the methotrexate such that the methotrexate is injected at a flow rate of at least about 0.5 ml/sec.

4. The hazardous agent injection system of claim 1, wherein the energy source comprises a spring.

5. The hazardous agent injection system of claim 1, wherein the energy source is configured for generating a pressure of at least about 80 p.s.i. in the container.

6. The hazardous agent injection system of claim 1, wherein the powered injector further comprises an outer housing member configured for allowing a user to handle the injector.

7. The hazardous agent injection system of claim 6, the powered injector further comprises a safety member removably affixed to the outer housing.

8. The hazardous agent injection system of claim 6, wherein the powered injector is a jet injector.

9. The hazardous agent injection system of claim 6, wherein the powered injector is not a jet injector.

10. The hazardous agent injection system of claim 7, wherein the safety member is removably affixed to the distal end of the outer housing.

11. The hazardous agent injection system of claim 7, wherein the safety member is removably affixed to the proximal end of the outer housing.

12. The hazardous agent injection system of claim 7, wherein the powered injector is a jet injector.

13. The hazardous agent injection system of claim 7, wherein the powered injector is not a jet injector.

14. The hazardous agent injection system of claim 10, wherein the safety member is a cap.

15. The hazardous agent injection system of claim 11, wherein the safety member is removably affixed to the proximal end of the outer housing by a plurality of tabs that extend through matching openings formed in the outer housing to form a press-fit between the safety member and the outer housing.

16. The hazardous agent injection system of claim 1, wherein the injector further comprises a syringe sleeve, the syringe sleeve having bore portion configured to abut the outside of the prefilled syringe wall so as to minimize syringe movement resulting from of the firing mechanism action.

17. The hazardous agent injection system of claim 1, wherein the injection-assisting needle is associated with the prefilled syringe.

18. The hazardous agent injection system of claim 1, wherein the injection-assisting needle is associated with the powered injector.

19. A method of treating a patient having an autoimmune disease, the method comprising administering methotrexate to the patient using the hazardous agent injection system of claim 1.

20. The method of claim 19, wherein the autoimmune disease is selected from the group consisting of rheumatoid arthritis, juvenile rheumatoid arthritis, psoriatic arthritis, systemic lupus erythematosus, steroid-resistant polymyositis or dermatomyositis, Wegener's granulomatosis, polyarteritis nodosa, and vasculitis.

* * * * *